United States Patent
Saeed et al.

(10) Patent No.: US 7,820,659 B2
(45) Date of Patent: Oct. 26, 2010

(54) CYCLOHEXYLIMIDIAZOLE LACTAM DERIVATIVES AS INHIBITORS OF 11-β-HYDROXYSTEROID DEHYDROGENASE 1

(75) Inventors: Ashraf Saeed, Westfield, IN (US); Owen Brendan Wallace, Westfield, IN (US); Yanping Xu, Noblesville, IN (US); Thomas Edward Mabry, Indianapolis, IN (US); Rebecca Lynn Rezac Guenther, Lonsdale, MN (US); Nancy June Snyder, Lizton, IN (US)

(73) Assignee: Eli Lilly and Company, Indianapolis, IN (US)

( * ) Notice: Subject to any disclaimer, the term of this patent is extended or adjusted under 35 U.S.C. 154(b) by 176 days.

(21) Appl. No.: 12/297,361

(22) PCT Filed: Apr. 19, 2007

(86) PCT No.: PCT/US2007/066907

§ 371 (c)(1),
(2), (4) Date: Oct. 16, 2008

(87) PCT Pub. No.: WO2007/124329

PCT Pub. Date: Nov. 1, 2007

(65) Prior Publication Data

US 2009/0088428 A1 Apr. 2, 2009

Related U.S. Application Data

(60) Provisional application No. 60/745,321, filed on Apr. 21, 2006.

(51) Int. Cl.
*A61K 31/41* (2006.01)
*A61K 31/42* (2006.01)
*A61K 31/44* (2006.01)
*A61K 31/445* (2006.01)
*A61K 31/497* (2006.01)
*A61K 31/505* (2006.01)
*A61K 31/535* (2006.01)
*C07D 211/32* (2006.01)
*C07D 403/02* (2006.01)
*C07D 413/14* (2006.01)

(52) U.S. Cl. .......... 514/234.5; 514/393; 514/338; 514/275; 514/322; 514/378; 514/254.06; 514/364; 548/306.1; 544/131; 544/139; 546/199

(58) Field of Classification Search .......... 548/306.1; 546/199; 544/139, 131; 514/393, 338, 234.5, 514/275, 322, 378, 254.06, 364
See application file for complete search history.

(56) References Cited

U.S. PATENT DOCUMENTS

| | | | |
|---|---|---|---|
| 2008/0207691 | A1 | 8/2008 | Aicher et al. |
| 2008/0214621 | A1 | 9/2008 | Aicher et al. |
| 2008/0275043 | A1 | 11/2008 | Aicher et al. |
| 2009/0069326 | A1 | 3/2009 | Allen et al. |
| 2009/0088430 | A1 | 4/2009 | Wallace et al. |
| 2009/0099180 | A1 | 4/2009 | Mabry et al. |
| 2009/0099182 | A1 | 4/2009 | Li et al. |
| 2009/0111800 | A1 | 4/2009 | Aicher et al. |
| 2009/0111809 | A1 | 4/2009 | Bush et al. |
| 2009/0156571 | A1 | 6/2009 | Aicher et al. |
| 2009/0239911 | A1 | 9/2009 | Wallace et al. |
| 2009/0264650 | A1 | 10/2009 | Yamashita et al. |
| 2009/0275613 | A1 | 11/2009 | Li et al. |

FOREIGN PATENT DOCUMENTS

| | | |
|---|---|---|
| EP | 1864971 | 12/2007 |
| WO | WO 2004/056744 | 7/2004 |
| WO | WO 2005/108360 | 11/2005 |
| WO | WO 2005/108361 | 11/2005 |
| WO | WO 2006/040329 | 4/2006 |
| WO | WO 2006/049952 | 5/2006 |
| WO | WO 2006/053024 | 5/2006 |
| WO | WO 2006/068991 | 6/2006 |
| WO | WO 2006/068992 | 6/2006 |
| WO | WO 2006/104280 | 10/2006 |
| WO | WO 2007/084314 | 7/2007 |
| WO | WO 2007/124254 | 11/2007 |
| WO | WO 2007/124337 | 11/2007 |

(Continued)

OTHER PUBLICATIONS

Yeh et al.: Discovery of orally active butyrolactam 11 β-HSD1 inhibitors, Bioorganic & Medicinal Chemistry Letters, Nov. 1, 2006, 16(21), pp. 5555-5560.

(Continued)

*Primary Examiner*—Rebecca L Anderson
(74) *Attorney, Agent, or Firm*—Dan L. Wood

(57) ABSTRACT

The present invention discloses novel compounds of Formula I: (I) having 11β-HSD type 1 antagonist activity, as well as methods for preparing such compounds. In another embodiment, the invention discloses pharmaceutical compositions comprising compounds of Formula I, as well as methods of using the compounds and compositions to treat diabetes, hyperglycemia, obesity, hypertension, hyperlipidemia, metabolic syndrome, and other conditions associated with 11β-HSD type 1 activity.

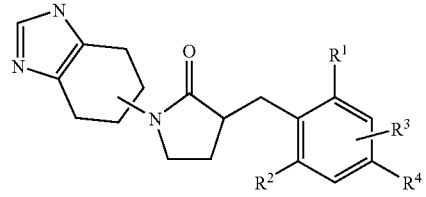

(I)

20 Claims, No Drawings

FOREIGN PATENT DOCUMENTS

| | | |
|---|---|---|
| WO | WO 2007/127688 | 11/2007 |
| WO | WO 2007/127693 | 11/2007 |
| WO | WO 2007/127704 | 11/2007 |
| WO | WO 2007/127726 | 11/2007 |
| WO | WO 2007/127763 | 11/2007 |
| WO | WO 2007/127765 | 11/2007 |
| WO | WO 2007/127901 | 11/2007 |
| WO | WO 2008/157752 | 12/2008 |

OTHER PUBLICATIONS

Schuster, Daniela et al.: The Discovery of New 11β-Hydroxysteroid Dehydrogenase Type 1 Inhibitors by Common Feature Pharmacophore Modeling and Virtual Screening, J. Medicinal Chemistry, 2006, 49, pp. 3454-3466.

Konno et al.: Electrolytic Partial Fluorination of Organic Compounds. 6. Highly Regioselective Eletrochemical Monofluorination of Aliphatic Nitrogen-Containing Heterocycles, Tetrahedron Letters, 1992, vol. 33, No. 46, pp. 7017-7020.

CYCLOHEXYLIMIDIAZOLE LACTAM DERIVATIVES AS INHIBITORS OF 11-β-HYDROXYSTEROID DEHYDROGENASE 1

This application is a 371 of PCT/US07/66907 filed Apr. 19, 2007 which claims the benefit of U.S. Provisional Application No. 60/745,321 filed Apr. 21, 2006.

This invention relates to compounds that are inhibitors of 11-β-hydroxysteroid dehydrogenase type 1 ("11-β-HSD1"), and to pharmaceutical compositions thereof, and the uses of these compounds and compositions in the treatment of the human or animal body, and to novel intermediates useful in preparation of the inhibitors. The present compounds show potent and selective inhibition of 11-β-HSD1, and as such are useful in the treatment of disorders responsive to the modulation of 11-β-HSD1, such as diabetes, metabolic syndrome, cognitive disorders, and the like.

Glucocorticoids acting in the liver, adipose tissue, and muscle, are important regulators of glucose, lipid, and protein metabolism. Chronic glucocorticoid excess is associated with insulin resistance, visceral obesity, hypertension, and dyslipidemia, which also represent the classical hallmarks of metabolic syndrome. 11-β-HSD1 catalyses the conversion of inactive cortisone to active cortisol, and has been implicated in the development of metabolic syndrome. Evidence in rodents and humans links 11-β-HSD1 to metabolic syndrome. Evidence suggests that a drug which specifically inhibits 11-β-HSD1 in type 2 diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secretion from the beta cells of the islet may also be increased. Evidence from animal and human studies also indicates that an excess of glucocorticoids impair cognitive function. Recent results indicate that inactivation of 11-β-HSD1 enhances memory function in both men and mice. The 11-β-HSD inhibitor carbenoxolone was shown to improve cognitive function in healthy elderly men and type 2 diabetics, and inactivation of the 11-β-HSD1 gene prevented aging-induced impairment in mice. Selective inhibition of 11-β-HSD1 with a pharmaceutical agent has recently been shown to improve memory retention in mice.

A number of publications have appeared in recent years reporting agents that inhibit 11-β-HSD1. See International Application WO2004/056744 which discloses adamantyl acetamides as inhibitors of 11-β-HSD, International Application WO2005/108360 which discloses pyrrolidin-2-one and piperidin-2-one derivatives as inhibitors of 11-β-HSD, and International Application WO2005/108361 which discloses adamantyl pyrrolidin-2-one derivatives as inhibitors of 11-β-HSD. In spite of the number of treatments for diseases that involve 11-β-HSD1, the current therapies suffer from one or more inadequacies, including poor or incomplete efficacy, unacceptable side effects, and contraindications for certain patient populations. Thus, there remains a need for an improved treatment using alternative or improved pharmaceutical agents that inhibit 11-β-HSD1 and treat the diseases that could benefit from 11-β-HSD1 inhibition. The present invention provides such a contribution to the art based on the finding that a novel class of compounds has a potent and selective inhibitory activity on 11-β-HSD1. The present invention is distinct in the particular structures and their activities. There is a continuing need for new methods of treating diabetes, metabolic syndrome, and cognitive disorders, and it is an object of this invention to meet these and other needs.

The present invention provides a compound structurally represented by formula I:

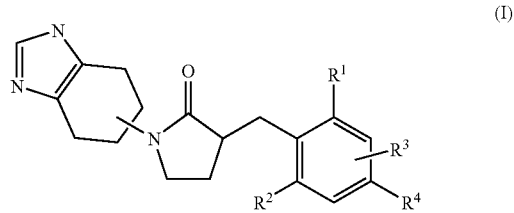

(I)

or a pharmaceutically acceptable salt thereof, wherein $R^1$ is —H, -halogen, —O—$CH_3$ (optionally substituted with one to three halogens), or —$CH_3$ (optionally substituted with one to three halogens);

$R^2$ is —H, -halogen, —O—$CH_3$ (optionally substituted with one to three halogens), or —$CH_3$ (optionally substituted with one to three halogens);

$R^3$ is —H or -halogen;

$R^4$ is

—OH, halogen, cyano, —($C_1$-$C_4$)alkyl(optionally substituted with one to three halogens), —($C_1$-$C_6$)alkoxy(optionally substituted with one to three halogens), —$SCF_3$, —C(O)O($C_1$-$C_4$)alkyl, —($C_3$-$C_8$)cycloalkyl, —O-phenyl-C(O)O—($C_1$-$C_4$)alkyl, —$CH_2$-phenyl, —$NHSO_2$—($C_1$-$C_4$)alkyl, —$NHSO_2$-phenyl($R^{21}$)($R^{21}$), —($C_1$-$C_4$)alkyl-C(O)N($R^{10}$)($R^{11}$),

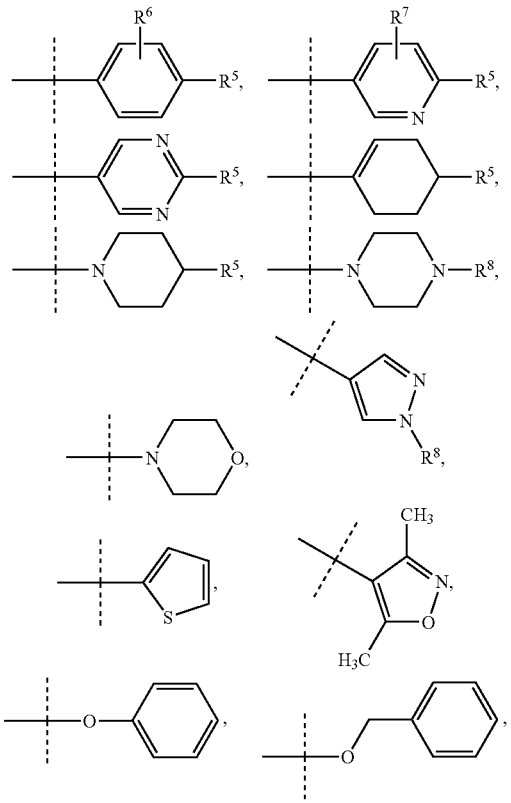

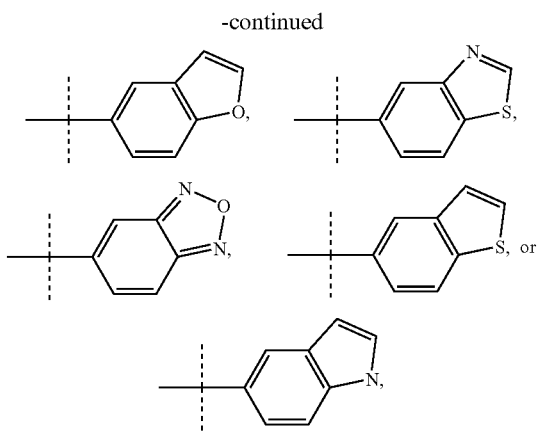

wherein the dashed line represents the point of attachment to the R⁴ position in formula I;

R⁵ is
—H, -halogen, —(C₁-C₄)alkyl(optionally substituted with 1 to 3 halogens),
—C(O)OH, —C(O)O—(C₁-C₄)alkyl, —C(O)—(C₁-C₄)alkyl, —O—(C₁-C₄)alkyl(optionally substituted with 1 to 3 halogens), —SO₂—(C₁-C₄)alkyl, —N(R⁸)(R⁸),

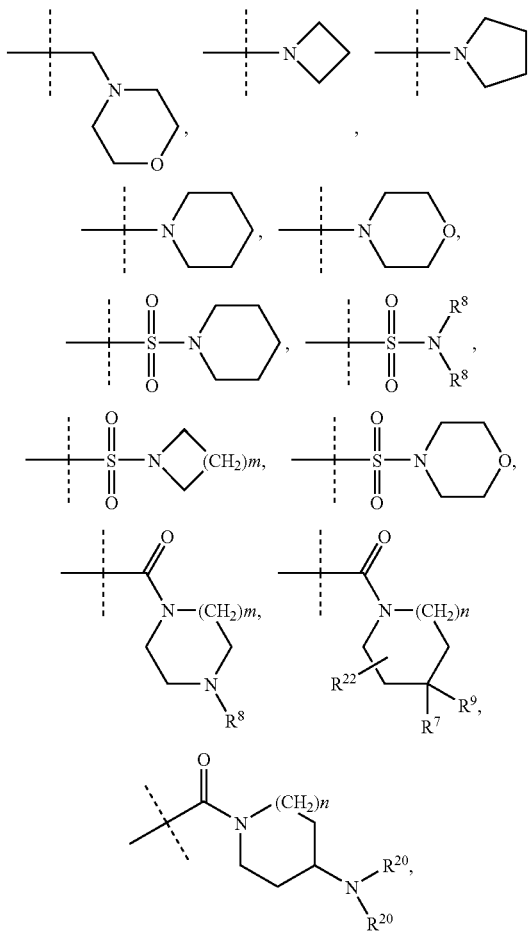

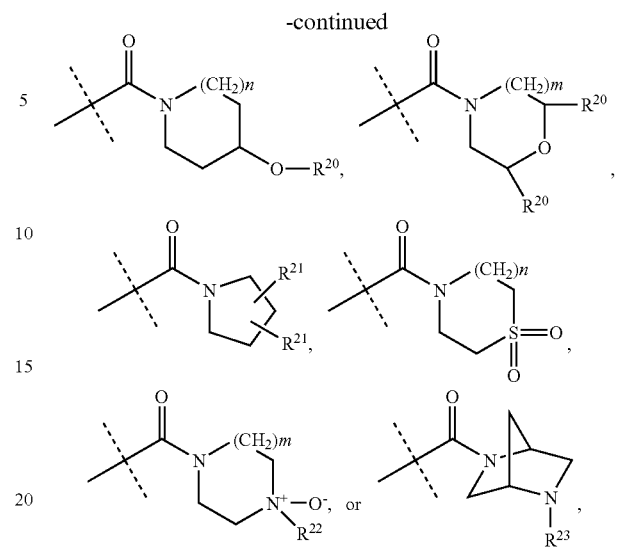

wherein the dashed line represents the point of attachment to the position indicated by R⁵;
wherein m is 1, 2, or 3;
wherein n is 0, 1, or 2, and wherein when n is 0, then "(CH₂)n" is a bond;

R⁶ is
—H, -halogen, —CN, or —(C₁-C₄)alkyl(optionally substituted with 1 to 3 halogens);

R⁷ is
—H, -halogen, or —(C₁-C₄)alkyl(optionally substituted with 1 to 3 halogens);

R⁸ is independently at each occurrence
—H, —(C₁-C₆)alkyl(optionally substituted with 1 to 3 halogens),
—C(O)—(C₁-C₆)alkyl(optionally substituted with 1 to 3 halogens),
—C(O)—(C₃-C₈)cycloalkyl, —S(O₂)—(C₃-C₈)cycloalkyl or
—S(O₂)—(C₁-C₃)alkyl(optionally substituted with 1 to 3 halogens);

R⁹ is —H or -halogen;

R¹⁰ and R¹¹ are each independently
—H or —(C₁-C₄)alkyl, or R¹⁰ and R¹¹ taken together with the nitrogen to which they are attached form piperidinyl, piperazinyl, or pyrrolidinyl;

R²⁰ is independently at each occurrence —H, or —(C₁-C₃)alkyl(optionally substituted with 1 to 3 halogens);

R²¹ is independently at each occurrence —H, -halogen, or —(C₁-C₃)alkyl(optionally substituted with 1 to 3 halogens);

R²² is independently at each occurrence —H or —(C₁-C₆)alkyl(optionally substituted with 1 to 3 halogens); and R²³ is independently at each occurrence —H, —(C₁-C₄)alkyl, or —C(O)O—(C₁-C₄)alkyl.

The present invention provides compounds of formula I that are useful as potent and selective inhibition of 11-β-HSD1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

In one embodiment, the present invention provides compounds of Formula I or a pharmaceutically acceptable salt thereof as described in detail above. While all of the compounds of the present invention are useful, certain of the compounds are particularly interesting and are preferred. The following listings set out several groups of preferred compounds.

In another embodiment the invention provides a compound structurally represented by formula Ia;

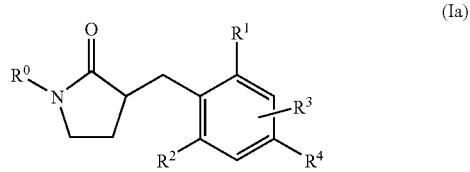

(Ia)

or a pharmaceutically acceptable salt thereof, wherein R⁰ is

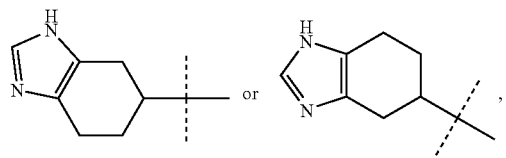

wherein the dashed line represents the point of attachment to the $R^0$ position in formula Ia;
$R^1$ is -halogen; $R^2$ is -halogen; $R^3$ is —H or -halogen; $R^4$ is

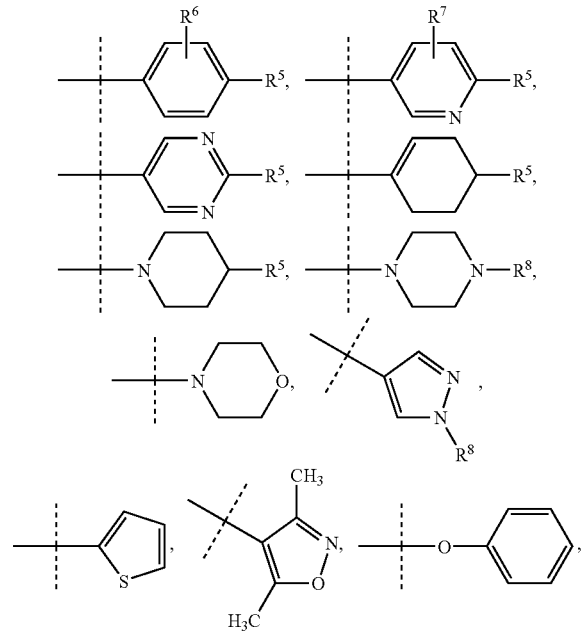

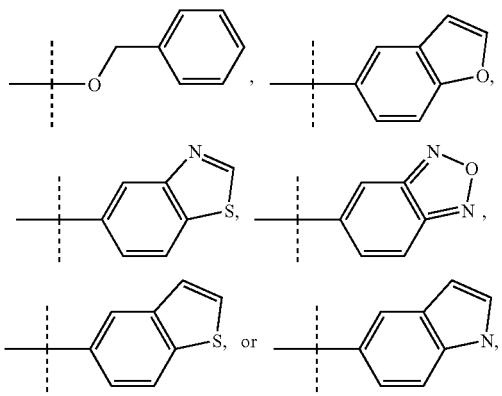

wherein the dashed line represents the point of attachment to the $R^4$ position in formula Ia;
$R^5$ is
—H, -halogen, —($C_1$-$C_4$)alkyl(optionally substituted with 1 to 3 halogens),
—C(O)OH, —C(O)O—($C_1$-$C_4$)alkyl, —C(O)—($C_1$-$C_4$)alkyl, —O—($C_1$-$C_4$)alkyl(optionally substituted with 1 to 3 halogens), —$SO_2$—($C_1$-$C_4$)alkyl, —N($R^8$)($R^8$),

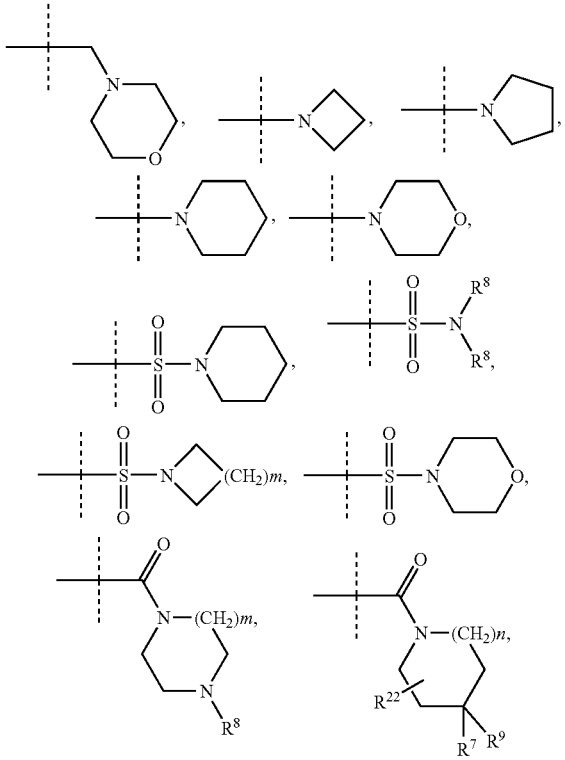

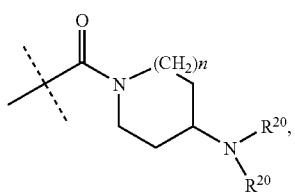

-continued

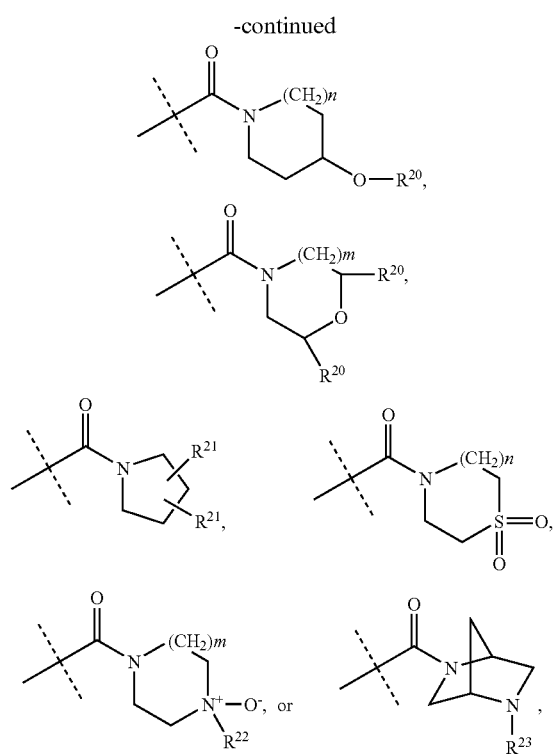

wherein the dashed line represents the point of attachment to the position indicated by $R^5$;

wherein m is 1, 2, or 3;

wherein n is 0, 1, or 2, and wherein when n is 0, then "(CH$_2$)n" is a bond;

$R^6$ is
—H, -halogen, —CN, or —(C$_1$-C$_4$)alkyl(optionally substituted with 1 to 3 halogens);

$R^7$ is
—H, -halogen, or —(C$_1$-C$_4$)alkyl(optionally substituted with 1 to 3 halogens);

$R^8$ is independently at each occurrence
—H, —(C$_1$-C$_6$)alkyl(optionally substituted with 1 to 3 halogens),
—C(O)—(C$_1$-C$_6$)alkyl(optionally substituted with 1 to 3 halogens),
—C(O)—(C$_3$-C$_8$)cycloalkyl, —S(O$_2$)—(C$_3$-C$_8$)cycloalkyl or
—S(O$_2$)—(C$_1$-C$_3$)alkyl(optionally substituted with 1 to 3 halogens);

$R^9$ is —H or -halogen;

$R^{20}$ is independently at each occurrence —H, or —(C$_1$-C$_3$)alkyl(optionally substituted with 1 to 3 halogens);

$R^{21}$ is independently at each occurrence —H, -halogen, or —(C$_1$-C$_3$)alkyl(optionally substituted with 1 to 3 halogens);

$R^{22}$ is independently at each occurrence —H or —(C$_1$-C$_6$)alkyl(optionally substituted with 1 to 3 halogens); and $R^{23}$ is independently at each occurrence —H, —(C$_1$-C$_4$)alkyl, or —C(O)O—(C$_1$-C$_4$)alkyl.

In another embodiment the invention provides a compound structurally represented by formula Ia;

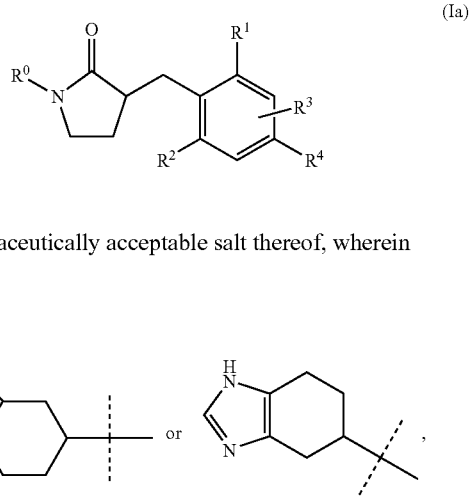

(Ia)

or a pharmaceutically acceptable salt thereof, wherein
$R^0$ is

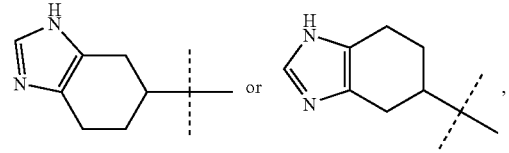

wherein the dashed line represents the point of attachment to the $R^0$ position in formula Ia;

$R^1$ is -chlorine, -fluorine, or -bromine; $R^2$ is -chlorine, -fluorine, or -bromine; $R^3$ is —H or -halogen;

$R^4$ is

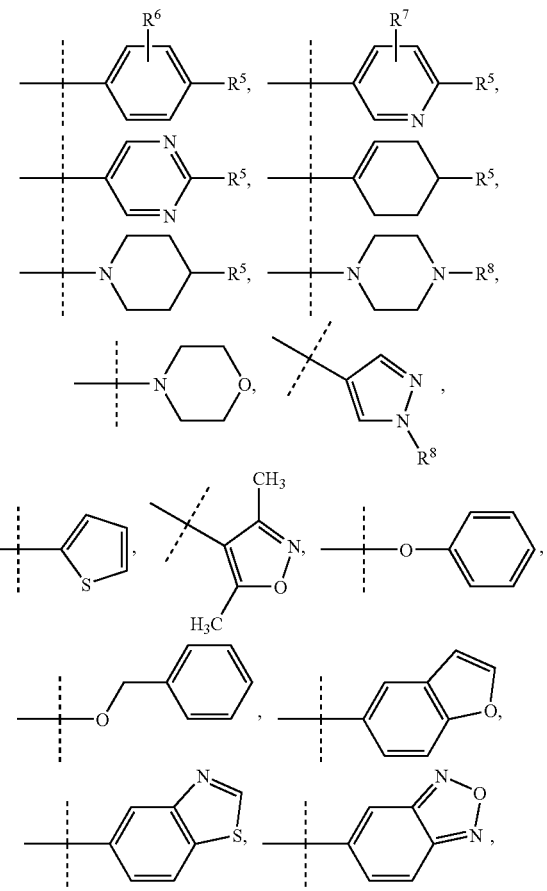

wherein the dashed line represents the point of attachment to the $R^4$ position in formula Ia;

$R^5$ is
—H, -halogen, —($C_1$-$C_4$)alkyl(optionally substituted with 1 to 3 halogens),
—C(O)OH, —C(O)O—($C_1$-$C_4$)alkyl, —C(O)—($C_1$-$C_4$)alkyl, —O—($C_1$-$C_4$)alkyl(optionally substituted with 1 to 3 halogens), —$SO_2$—($C_1$-$C_4$)alkyl, —N($R^8$)($R^8$), wherein the dashed line represents the point of attachment to the position indicated by $R^5$; wherein m is 1, 2, or 3;

$R^6$ is
—H, -halogen, —CN, or —($C_1$-$C_4$)alkyl(optionally substituted with 1 to 3 halogens);

$R^7$ is
—H, -halogen, or —($C_1$-$C_4$)alkyl(optionally substituted with 1 to 3 halogens);

$R^8$ is independently at each occurrence
—H, —($C_1$-$C_6$)alkyl(optionally substituted with 1 to 3 halogens), —C(O)—($C_1$-$C_6$)alkyl(optionally substituted with 1 to 3 halogens), —C(O)—($C_3$-$C_8$)cycloalkyl, —S($O_2$)—($C_3$-$C_8$)cycloalkyl or —S($O_2$)—($C_1$-$C_3$)alkyl(optionally substituted with 1 to 3 halogens);

$R^9$ is —H or -halogen;

$R^{20}$ is independently at each occurrence —H, or —($C_1$-$C_3$)alkyl(optionally substituted with 1 to 3 halogens);

$R^{21}$ is independently at each occurrence —H, -halogen, or —($C_1$-$C_3$)alkyl(optionally substituted with 1 to 3 halogens);

$R^{22}$ is independently at each occurrence —H or —($C_1$-$C_6$)alkyl(optionally substituted with 1 to 3 halogens); and $R^{23}$ is independently at each occurrence —H, —($C_1$-$C_4$)alkyl, or —C(O)O—($C_1$-$C_4$)alkyl.

In another embodiment the invention provides a compound structurally represented by formula Ia;

(Ia)

or a pharmaceutically acceptable salt thereof, wherein $R^0$ is wherein the dashed line represents the point of attachment to the $R^0$ position in formula Ia;

$R^1$ is -chlorine, -fluorine, or -bromine; $R^2$ is -chlorine, -fluorine, or -bromine; $R^3$ is —H or -halogen;

$R^4$ is

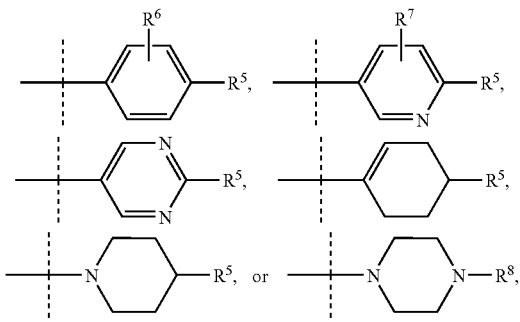

wherein the dashed line represents the point of attachment to the $R^4$ position in formula Ia;

$R^5$ is

—H, -halogen, —$(C_1$-$C_4)$alkyl(optionally substituted with 1 to 3 halogens),

—C(O)OH, —C(O)O—$(C_1$-$C_4)$alkyl, —C(O)—$(C_1$-$C_4)$alkyl, —O—$(C_1$-$C_4)$alkyl(optionally substituted with 1 to 3 halogens), —$SO_2$—$(C_1$-$C_4)$alkyl, —$N(R^8)(R^8)$,

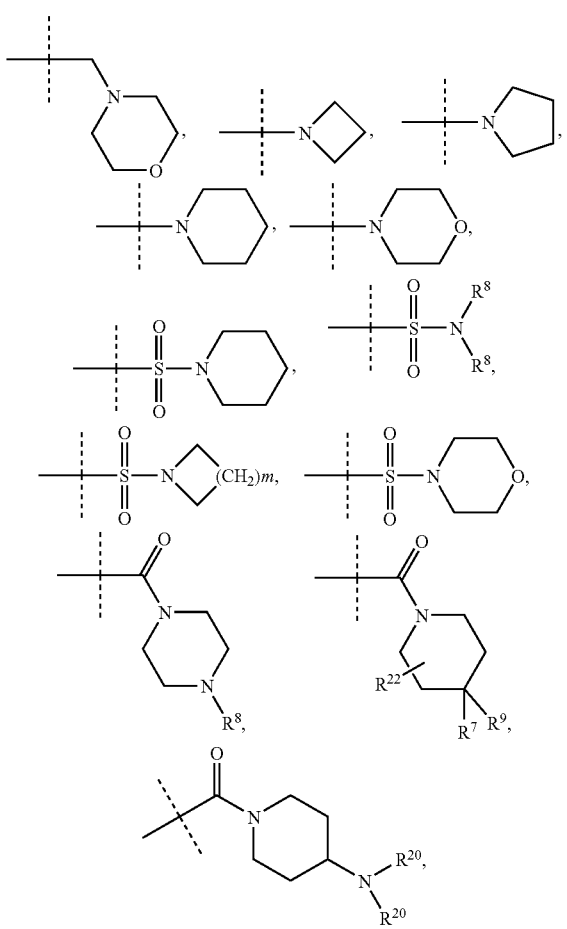

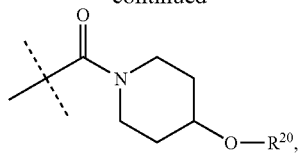

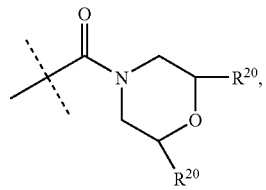

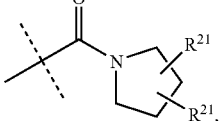

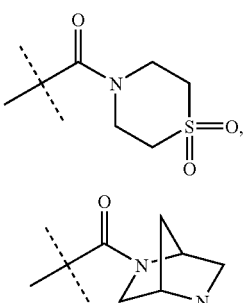

wherein the dashed line represents the point of attachment to the position indicated by $R^5$; wherein m is 1, 2, or 3;

$R^6$ is

—H, -halogen, —CN, or —$(C_1$-$C_4)$alkyl(optionally substituted with 1 to 3 halogens);

$R^7$ is

—H, -halogen, or —$(C_1$-$C_4)$alkyl(optionally substituted with 1 to 3 halogens);

$R^8$ is independently at each occurrence

—H, —$(C_1$-$C_6)$alkyl(optionally substituted with 1 to 3 halogens),

—C(O)—$(C_1$-$C_6)$alkyl(optionally substituted with 1 to 3 halogens),

—C(O)—$(C_3$-$C_8)$cycloalkyl, —$S(O_2)$—$(C_3$-$C_8)$cycloalkyl or

—$S(O_2)$—$(C_1$-$C_3)$alkyl(optionally substituted with 1 to 3 halogens);

$R^9$ is —H or -halogen;

$R^{20}$ is independently at each occurrence —H, or —$(C_1$-$C_3)$alkyl(optionally substituted with 1 to 3 halogens);

$R^{21}$ is independently at each occurrence —H, -halogen, or —$(C_1$-$C_3)$alkyl(optionally substituted with 1 to 3 halogens);

$R^{22}$ is independently at each occurrence —H or —$(C_1$-$C_6)$alkyl(optionally substituted with 1 to 3 halogens); and $R^{23}$ is independently at each occurrence —H, —$(C_1$-$C_4)$alkyl, or —C(O)O—$(C_1$-$C_4)$alkyl.

In another embodiment the invention provides a compound structurally represented by formula Ia;

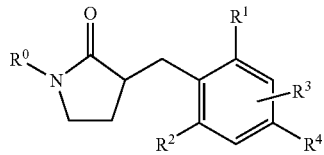
(Ia)

or a pharmaceutically acceptable salt thereof, wherein
$R^0$ is

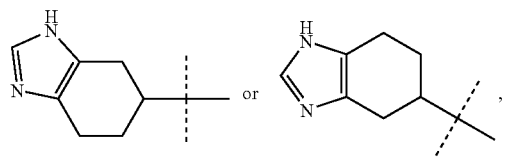

wherein the dashed line represents the point of attachment to the $R^0$ position in formula Ia;

$R^1$ is -chlorine, -fluorine, or -bromine; $R^2$ is -chlorine, -fluorine, or -bromine; $R^3$ is —H or -halogen;

$R^4$ is

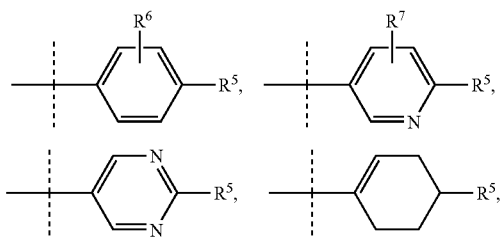

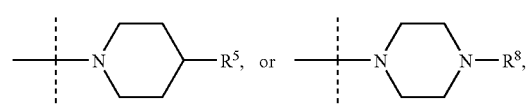

wherein the dashed line represents the point of attachment to the $R^4$ position in formula Ia;

$R^5$ is

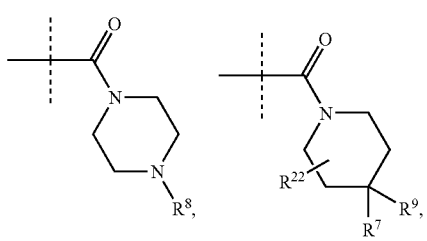

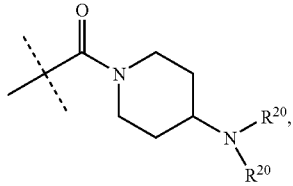

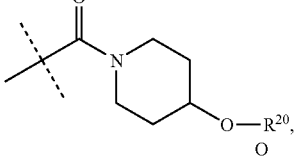

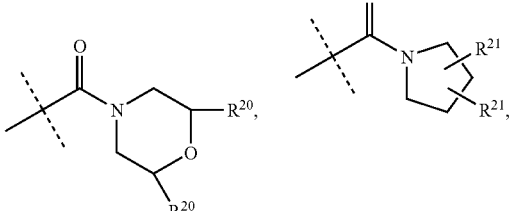

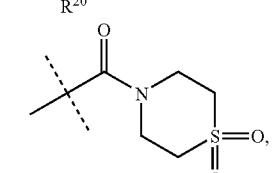

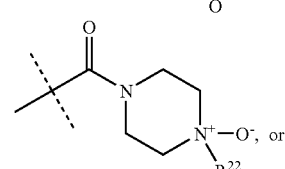

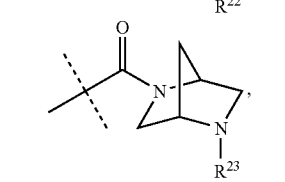

wherein the dashed line represents the point of attachment to the position indicated by $R^5$;

$R^6$ is
—H, -halogen, —CN, or —$(C_1-C_4)$alkyl(optionally substituted with 1 to 3 halogens);

$R^7$ is
—H, -halogen, or —$(C_1-C_4)$alkyl(optionally substituted with 1 to 3 halogens);

$R^8$ is independently at each occurrence
—H, —$(C_1-C_6)$alkyl(optionally substituted with 1 to 3 halogens), —C(O)—$(C_1-C_6)$alkyl(optionally substituted with 1 to 3 halogens), —C(O)—$(C_3-C_8)$cycloalkyl, —S($O_2$)—$(C_3-C_8)$cycloalkyl or —S($O_2$)—$(C_1-C_3)$alkyl(optionally substituted with 1 to 3 halogens);

$R^9$ is —H or -halogen;

$R^{20}$ is independently at each occurrence —H, or —$(C_1-C_3)$alkyl(optionally substituted with 1 to 3 halogens);

$R^{21}$ is independently at each occurrence —H, -halogen, or —$(C_1-C_3)$alkyl(optionally substituted with 1 to 3 halogens);

$R^{22}$ is independently at each occurrence —H or —($C_1$-$C_6$) alkyl(optionally substituted with 1 to 3 halogens); and $R^{23}$ is independently at each occurrence —H, —($C_1$-$C_4$) alkyl, or —C(O)O—($C_1$-$C_4$)alkyl.

In another embodiment the invention provides a compound structurally represented by formula Ia;

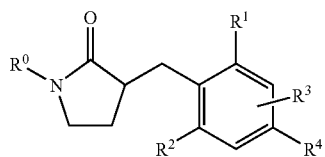

(Ia)

or a pharmaceutically acceptable salt thereof, wherein
$R^0$ is

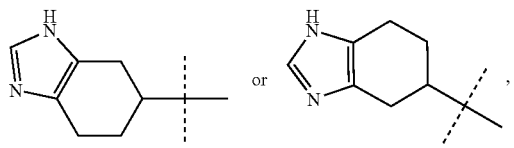

wherein the dashed line represents the point of attachment to the $R^0$ position in formula Ia;

$R^1$ is -chlorine, -fluorine, or -bromine; $R^2$ is -chlorine, -fluorine, or -bromine; $R^3$ is —H or -halogen;

$R^4$ is

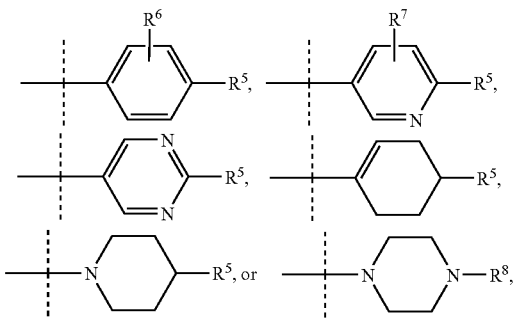

wherein the dashed line represents the point of attachment to the $R^4$ position in formula Ia;

$R^5$ is
—$SO_2$—($C_1$-$C_4$)alkyl,

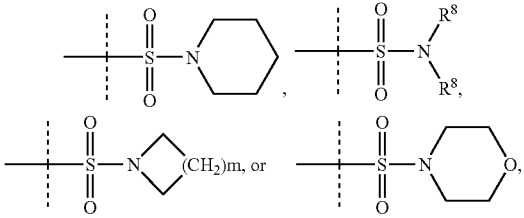

wherein the dashed line represents the point of attachment to the position indicated by $R^5$; wherein m is 1, 2, or 3;

$R^6$ is
—H, -halogen, —CN, or —($C_1$-$C_4$)alkyl(optionally substituted with 1 to 3 halogens);

$R^7$ is
—H, -halogen, or —($C_1$-$C_4$)alkyl(optionally substituted with 1 to 3 halogens); and $R^8$ is independently at each occurrence
—H, —($C_1$-$C_6$)alkyl(optionally substituted with 1 to 3 halogens),
—C(O)—($C_1$-$C_6$)alkyl(optionally substituted with 1 to 3 halogens),
—C(O)—($C_3$-$C_8$)cycloalkyl, —$S(O_2)$—($C_3$-$C_8$)cycloalkyl or
—$S(O_2)$—($C_1$-$C_3$)alkyl(optionally substituted with 1 to 3 halogens).

In another embodiment the invention provides a compound structurally represented by formula Ia;

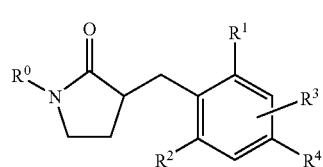

(Ia)

or a pharmaceutically acceptable salt thereof, wherein
$R^0$ is

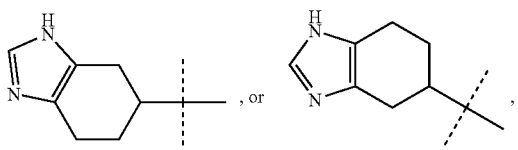

wherein the dashed line represents the point of attachment to the $R^0$ position in formula Ia;

$R^1$ is -chlorine, -fluorine, or -bromine; $R^2$ is -chlorine, -fluorine, or -bromine; $R^3$ is —H or -halogen;

$R^4$ is

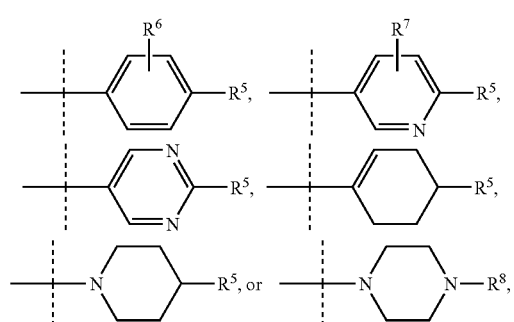

wherein the dashed line represents the point of attachment to the $R^4$ position in formula Ia;

$R^5$ is
—N($R^8$)($R^8$),

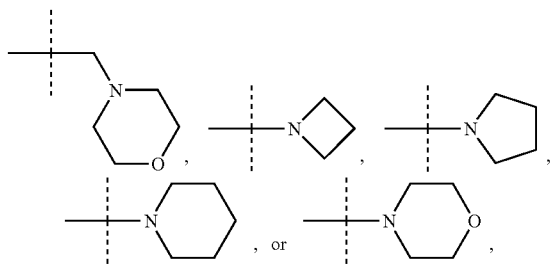

wherein the dashed line represents the point of attachment to the position indicated by $R^5$;

$R^6$ is
- —H, -halogen, —CN, or —$(C_1-C_4)$alkyl(optionally substituted with 1 to 3 halogens);

$R^7$ is
- —H, -halogen, or —$(C_1-C_4)$alkyl(optionally substituted with 1 to 3 halogens); and $R^8$ is independently at each occurrence
- —H, —$(C_1-C_6)$alkyl(optionally substituted with 1 to 3 halogens),
- —C(O)—$(C_1-C_6)$alkyl(optionally substituted with 1 to 3 halogens),
- —C(O)—$(C_3-C_8)$cycloalkyl, —S(O_2)—$(C_3-C_8)$cycloalkyl or
- —S(O_2)—$(C_1-C_3)$alkyl(optionally substituted with 1 to 3 halogens).

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably embodiments of the invention are structurally represented by the formula:

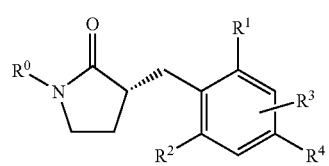

wherein $R^0$ is

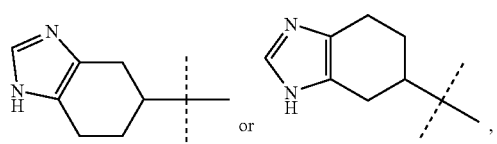

or a stereoisomer thereof, or a pharmaceutically acceptable salt thereof.

Preferably $R^0$ is

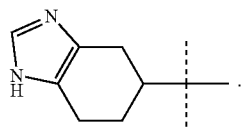

Preferably $R^0$ is

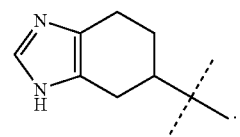

Preferably $R^1$ is -halogen. Preferably $R^1$ is —$CH_3$. Preferably $R^1$ is -chlorine, -fluorine, or -bromine. Preferably $R^1$ is -chlorine. Preferably $R^1$ is -fluorine. Preferably $R^1$ is -bromine. Preferably $R^2$ is -halogen. Preferably $R^2$ is —$CH_3$ Preferably $R^2$ is -chlorine, -fluorine, or -bromine. Preferably $R^2$ is -chlorine. Preferably $R^2$ is -fluorine. Preferably $R^2$ is -bromine. Preferably $R^1$ is -chlorine and $R^2$ is -chlorine. Preferably $R^3$ is —H. Preferably $R^3$ is -halogen.

Preferably $R^4$ is

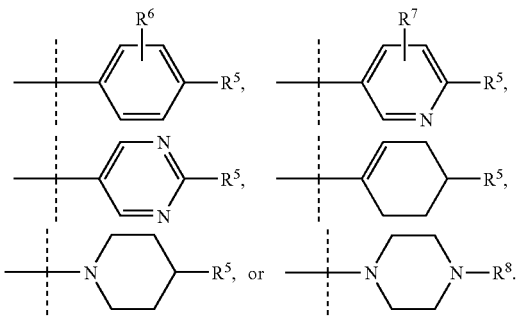

Preferably $R^4$ is

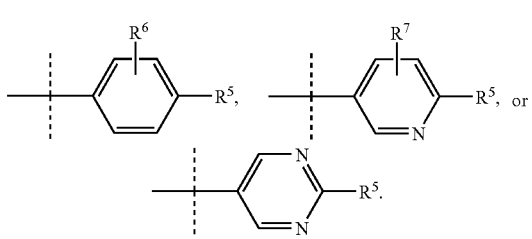

Preferably $R^4$ is

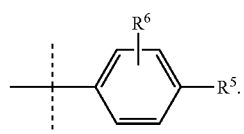

Preferably $R^4$ is
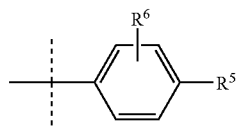
and $R^6$ is hydrogen. Preferably $R^4$ is
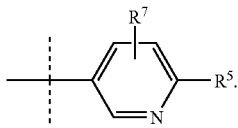
Preferably $R^4$ is
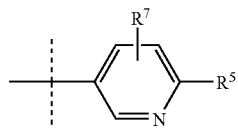
and $R^7$ is hydrogen. Preferably $R^4$ is
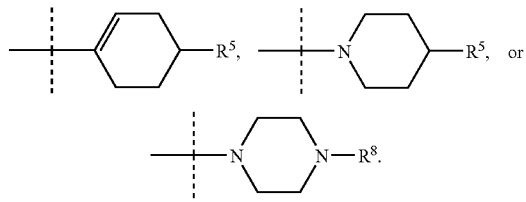
Preferably $R^4$ is
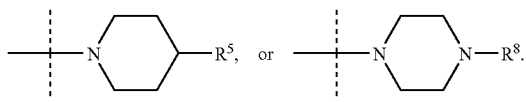
Preferably $R^4$ is
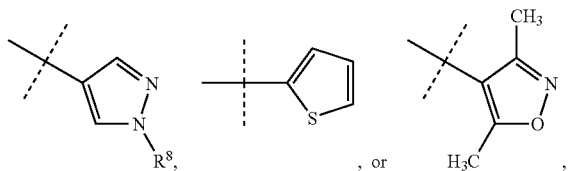
Preferably $R^4$ is
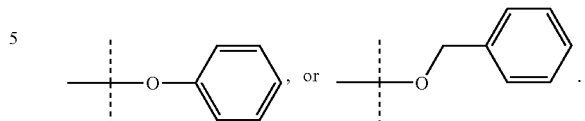
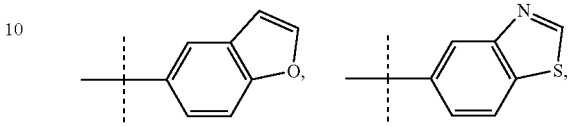
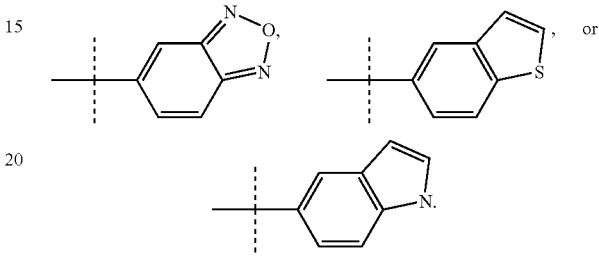
Preferably $R^4$ is
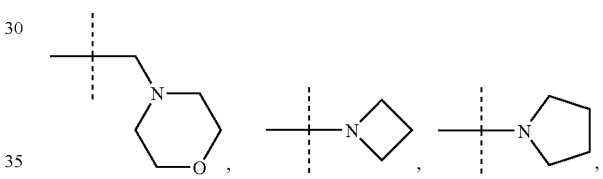
Preferably $R^5$ is —N($R^8$)($R^8$),
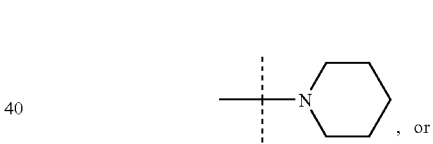
Preferably $R^5$ is —SO$_2$—(C$_1$-C$_4$)alkyl,
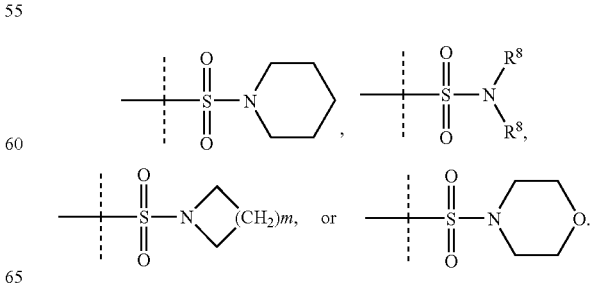

Preferably $R^5$ is

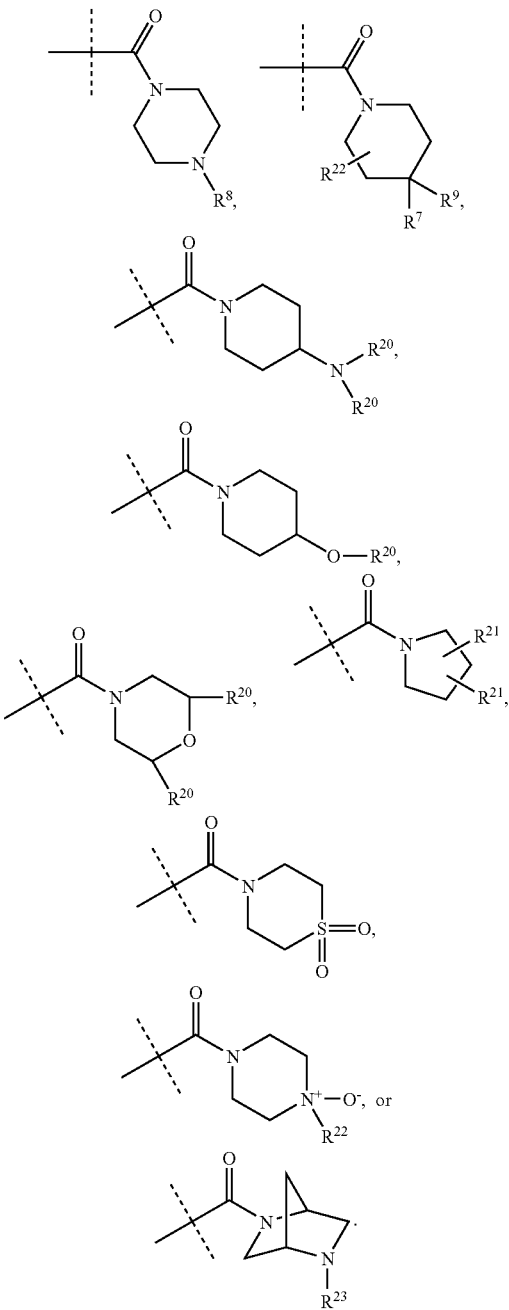

Preferably $R^5$ is

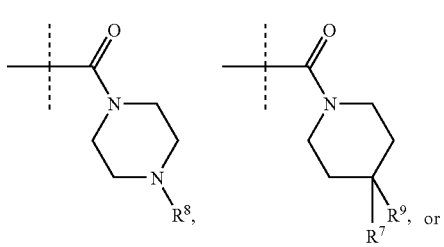

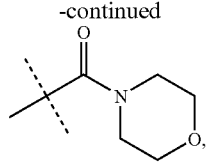

and $R^8$ is —$(C_1$-$C_3)$alkyl(optionally substituted with 1 to 3 halogens). Preferably $R^5$ is halogen. Preferably $R^5$ is chlorine. Preferably $R^5$ is fluorine.

Preferably $R^6$ is —H. Preferably $R^6$ is -halogen. Preferably $R^6$ is —$(C_1$-$C_4)$alkyl(optionally substituted with 1 to 3 halogens). Preferably $R^7$ is —H. Preferably $R^7$ is -halogen, or —$(C_1$-$C_4)$alkyl(optionally substituted with 1 to 3 halogens). Preferably $R^7$ is -halogen. Preferably $R^7$ is —$(C_1$-$C_4)$alkyl (optionally substituted with 1 to 3 halogens). Preferably $R^8$ is independently at each occurrence —H. Preferably $R^8$ is independently at each occurrence —$(C_1$-$C_3)$alkyl. Preferably $R^8$ is independently at each occurrence —$CH_3$. Preferably $R^9$ is —H. Preferably $R^9$ is -halogen. Preferably $R^7$ is -fluorine and $R^9$ is -fluorine.

In another embodiment the invention provides a compound structurally represented by formula Ia, or a pharmaceutically acceptable salt thereof, wherein $R^0$ is

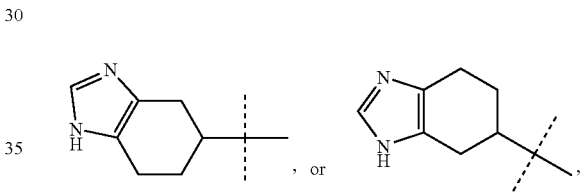

wherein the dashed line represents the point of attachment to the $R^0$ position in formula Ia; $R^1$ is -chlorine; $R^2$ is -chlorine; $R^3$ is —H;

$R^4$ is

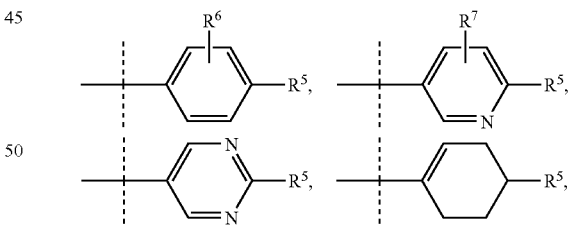

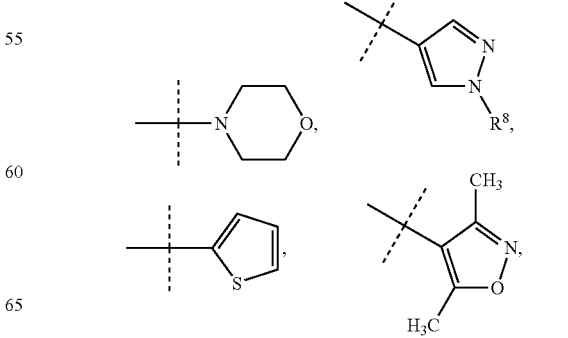

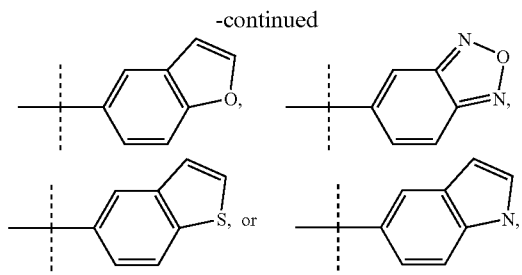

wherein the dashed line represents the point of attachment to the $R^4$ position in formula Ia;

$R^5$ is

—H, -chlorine, -fluorine, —$CH_3$, —$CF_3$, —$C(CH_3)_3$, —$CH(CH_3)_2$, —O—$C(CH_3)_2$—$C(O)O$—$CH_3$, —N(—$CH_3$)(—$CH_3$),

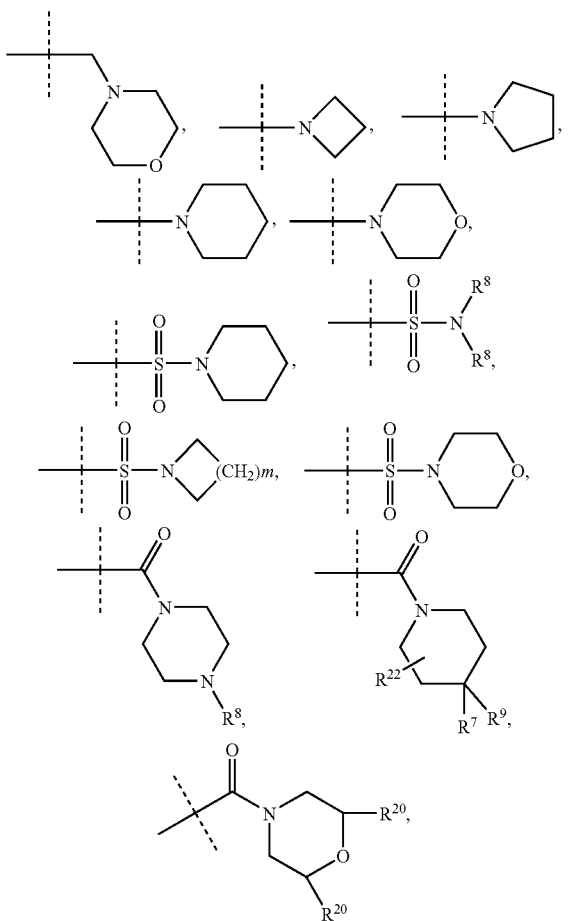

wherein the dashed line represents the point of attachment to the position indicated by $R^5$; wherein m is 1, 2, or 3;

$R^6$ is —H, -chlorine, -fluorine, -bromine, —$CH_3$, $CF_3$;

$R^7$ is —H, -chlorine, -fluorine, -bromine ;

$R^8$ is independently at each occurrence —H or —$CH_3$, —$CH_2$—$CH_3$, —$C(CH_3)_3$, —$CH(CH_3)_2$;

$R^9$ is —H or -chlorine, -fluorine, -bromine;

$R^{20}$ is independently at each occurrence —H, —$CH_3$; and $R^{22}$ is independently at each occurrence —H.

Preferred embodiments of the invention are compounds of the formula (R)-3-(3,5-Dichloro-4'-morpholin-4-yl-biphenyl-4-ylmethyl)-1-(4,5,6,7-tetrahydro-1H-benzoimidazol-5-yl)-pyrrolidin-2-one, (R)-3-[2,6-Dichloro-4-(2-fluoro-6-morpholin-4-yl-pyridin-3-yl)-benzyl]-1-(4,5,6,7-tetrahydro-1H-benzoimidazol-5-yl)-pyrrolidin-2-one, and 3-[R]-[3,5-Dichloro-4'-(4-trifluoromethyl-piperidine-1-carbonyl)-biphenyl-4-ylmethyl]-1-(4,5,6,7-tetrahydro-3H-benzoimidazol-5-yl)-pyrrolidin-2-one, or 3-(3,5-Dichloro-4'-fluoro-biphenyl-4-ylmethyl)-1-(4,5,6,7-tetrahydro-1H-benzoimidazol-5-yl)-pyrrolidin-2-one; or stereoisomers thereof, or a pharmaceutically acceptable salts thereof. A further embodiment of the invention are the novel intermediate preparations described herein which are useful for preparing the 11-β-HSD1 inhibitors according to formula I and the embodiments described herein.

Patients with type 2 diabetes often develop "insulin resistance" which results in abnormal glucose homeostasis and hyperglycemia leading to increased morbidity and premature mortality. Abnormal glucose homeostasis is associated with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are important in the management and treatment of diabetes mellitus. Many patients who have insulin resistance but have not developed type 2 diabetes are also at risk of developing "Syndrome X" or "Metabolic syndrome". Metabolic syndrome is characterized by insulin resistance along with abdominal obesity, hyperinsulinemia, high blood pressure, low HDL, high VLDL, hypertension, atherosclerosis, coronary heart disease, and chronic renal failure. These patients are at increased risk of developing the cardiovascular complications listed above whether or not they develop overt diabetes mellitus.

Due to their inhibition of 11-β-HSD1, the present compounds are useful in the treatment of a wide range of conditions and disorders in which inhibition of 11-β-HSD1 is beneficial. These disorders and conditions are defined herein as "diabetic disorders" and "metabolic syndrome disorders". One of skill in the art is able to identify "diabetic disorders" and "metabolic syndrome disorders" by the involvement of 11-β-HSD1 activity either in the pathophysiology of the disorder, or in the homeostatic response to the disorder. Thus, the compounds may find use for example to prevent, treat, or alleviate, diseases or conditions or associated symptoms or sequelae, of "Diabetic disorders" and "metabolic syndrome disorders".

"Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, metabolic syndrome, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus the present invention also provides a method of treatment of "Diabetic disorders" and "metabolic syndrome disorders" while reducing and or eliminating one or more of the unwanted side effects associated with the current treatments.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting 11-β-HSD1 activity; for use in inhibiting a 11-β-HSD1 activity mediated cellular response in a mammal; for use in reducing the glycemic level in a mammal; for use in treating a disease arising from excessive 11-β-HSD1 activity; for use in treating diabetic and other metabolic syndrome disorders in a mammal; and for use in treating diabetes, metabolic syndrome, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting 11-β-HSD1 activity; for the manufacture of a medicament for inhibiting 11-β-HSD1 activity mediated cellular response in a mammal; for the manufacture of a medicament for reducing the glycemic level in a mammal; for the manufacture of a medicament for treating a disease arising from excessive 11-β-HSD1 activity; for the manufacture of a medicament for treating diabetic and other metabolic syndrome disorders in a mammal; and for the manufacture of a medicament for preventing or treating diabetes, metabolic syndrome, obesity, hyperglycemia, atherosclerosis, ischemic heart disease, stroke, neuropathy, and improper wound healing.

The present invention further provides a method of treating conditions resulting from excessive 11-β-HSD1 activity in a mammal; a method of inhibiting 11-β-HSD1 activity in a mammal; a method of inhibiting a 11-β-HSD1 activity mediated cellular response in a mammal; a method of reducing the glycemic level in a mammal; a method of treating diabetic and other metabolic syndrome disorders in a mammal; a method of preventing or treating diabetes, metabolic syndrome, obesity, hyperglycemia, atherosclerosis, ischemic heart disease, stroke, neuropathy, and improper wound healing; said methods comprising administering to a mammal in need of such treatment a 11-β-HSD1 activity inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting 11-β-HSD1 activity; adapted for use in inhibiting 11-β-HSD1 activity mediated cellular responses; adapted for use in reducing the glycemic level in a mammal; adapted for use in treating diabetic and other metabolic syndrome disorders in a mammal; and adapted for use in preventing or treating diabetes, metabolic syndrome, obesity, hyperglycemia, atherosclerosis, ischemic heart disease, stroke, neuropathy, and wound healing.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $ASP^{B28}$ human insulin, U.S. Pat. No. 5,504,188 (Eli Lilly), for example $Lys^{B28}$ $Pro^{B29}$ human insulin, EP 368 187 (Aventis), for example Lantus®, GLP-1 and GLP-1 derivatives such as those disclosed in WO 98/08871 (Novo Nordisk A/S), as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S), or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), GSK-3 (glycogen synthase kinase-3) inhibitors, compounds modifying the lipid metabolism such as antilipidemics agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation).

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S).

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

General terms used in the description of compounds herein described bear their usual meanings.

As used herein, the terms "$(C_1$-$C_3)$alkyl", "$(C_1$-$C_4)$alkyl" or "$(C_1$-$C_6)$alkyl" refer to straight-chain or branched-chain saturated aliphatic groups of the indicated number of carbon atoms, such as methyl, ethyl, n-propyl, isopropyl, n-butyl, isobutyl, sec-butyl, t-butyl, and the like. The term "$(C_1$-$C_6)$ alkoxy" represents a $C_1$-$C_6$ alkyl group attached through an oxygen and include moieties such as, for example, methoxy, ethoxy, n-propoxy, isopropoxy, and the like. The term "halogen" refers to fluoro, chloro, bromo, and iodo. The term "$(C_3$-$C_8)$ cycloalkyl" refers to a saturated or partially saturated carbocycle ring of from 3 to 8 carbon atoms, typically 3 to 7 carbon atoms. Examples of $(C_3$-$C_8)$ cycloalkyl include but are not limited to cyclopropyl, cyclobutyl, cyclopentyl, cyclohexyl, cycloheptyl, and the like.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

It is understood that guinea pigs, dogs, cats, rats, mice, hamsters, and primates, including humans, are examples of patients within the scope of the meaning of the term "patient". Preferred patients include humans. The term "patient" includes livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "substantially pure" refers to pure crystalline form of a compound comprising greater than about 90% of the desired crystalline form, and preferably, greater than about 95% of the desired crystal form.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may have one or more chiral centers and may exist in a variety of stereoisomeric configurations. As a consequence of these chiral centers the compounds of the present invention can occur as racemates, as individual enantiomers or mixtures of enantiomers, as well as diastereomers and mixtures of diastereomers. All such racemates, enantiomers, diastereomers and mixtures are within the scope of the present invention, whether pure, partially purified, or unpurified mixtures. For the examples provided herein, when a molecule which contains a chiral center or centers of known configuration is presented, its stereochemistry is designated in the name and in the structural representation of the molecule. If the stereochemistry is unknown or undefined its stereochemistry is not designated in the name or in the structural representation of the molecule. Embodiments of the invention include the Examples provided herein, and although the Example provided may be of one chiral or conformational form, or a salt thereof, further embodiments of the invention include all other steroisomeric and or conformational forms of the examples described, as well as pharmaceutically acceptable salts thereof. These embodiments include any isolated enantiomers, diastereomers, and or conformers of these structures, as well as any mixtures containing more than one form.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms which the compounds are able to form are included within the scope of the present invention.

The term "enantiomeric enrichment" as used herein refers to the increase in the amount of one enantiomer as compared to the other. A convenient method of expressing the enantiomeric enrichment achieved is the concept of enantiomeric excess, or ee which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative lability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "psi" refers to pounds per square inch; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates [M+H] unless indicated otherwise. "MS (APCi) refers to atmospheric pressure chemical ionization mass spectrometry, "UV" refers to ultraviolet spectrometry, "$^1$H NMR" refers to proton nuclear magnetic resonance spectrometry. "LCMS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylforamide, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N'-(3-dimethylaminopropyl)carbodiimide hydrochloride, "HOBT" refers to 1-Hydroxy benzotriazole, "Bn-9-BBN" refers to Benzyl-9-borabicyclo [3.3.1]nonane, "Pd(dppf)Cl$_2$" refers to [1,1'-Bis(diphenylphosphino)-ferrocene)dichloropalladium(II), "EDCI" refers to N-Ethyl-N'-(3-dimethylaminopropyl)carbodiimide hydrochloride, "DBU" refers to 1,8-Diazabicyclo[5.4.0]undecene-7, "TBSCl" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$" refers to Bis(dibenzylideneacetone)palladium, "BINAP" refers to 2,2'-Bis (diphenylphospino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi-Pr)$_3$ refers to methyltitanium triisopropoxide, "BBr$_3$" refers to boron tribromide, "PBr$_3$" refers to phosphorous tribromide, "Pd (PPh$_3$)$_4$" refers to tetrakis(triphenylphoshine)palladium (0), "OAc" refers to acetate, "DME" refers to dimethylethane, "Et$_2$O" refers to diethyl ether, "(Ph$_3$P)$_4$Pd" refers to tetrakis (triphenylphoshine)palladium (0), "DMFDMA" refers to N,N-dimethylformamide dimethyl acetal, "Et$_3$N" refers to triethylamine, "tBu" refers to t-butyl, "DIPEA" refers to diisopropylethyl amine, "EDC" refers to -(3-Dimethylaminopropyl)-3-ethylcarbodiimide hydrochloride, "HOAc" refers to acetic acid, "boc" refers to t-butoxycarbonyl. In a structure, "Ph" refers to phenyl, "Me" refers to methyl, "Et" refers to ethyl, "Bn" refers to benzyl, "MeOH" refers to methanol, "OTf" refers to trifluoromethanesulfonate, "TIPSO" refers to triisopropylsilanyloxy, "TBSO" refers to tert-butyl-dimethyl-silanyloxy.

The Examples provided herein are illustrative of the invention claimed herein and are not intended to limit the scope of the claimed invention in any way. The preparations and examples are named using AutoNom 2.2 in ChemDraw Ultra, or AutoNom 2000 in MDL ISIS/Draw version 2.5 SP1 from MDL Information Systems, Inc., or are provided by Chemical Abstracts Services.

A Varian INOVA 400 MHz spectrometer is used to obtain $^1$H NMR Specta the in the solvent indicated. An Agilent HP 1100 instrument equipped with a Mass Spectrometer (Agilent MSD SL) is used to obtain LCMS. A Waters Xterra C18 (2.1×50 mm, 3.5 micron) is used as stationary phase and a standard method is a gradient of 5-100% acetonitrile/methanol (50:50) with 0.2% ammonium formate over 3.5 minutes then held at 100% B for 0.5 minutes at a column temperature of 50° C. and a flow rate of 1.0 mL/min. Another standard method is a gradient of 5-100% acetonitrile/methanol (50:50) with 0.2% ammonium formate over 7.0 minutes then held at 100% B for 1.0 minutes at a column temperature of 50° C. and a flow rate of 1.0 mL/min. Additional MS analysis via Agilent MSD (loop machine) is standard Flow injection Analysis (FIA), no column is present and flow is 0.5 ml/min of 80% MeOH with 6.5 mM Ammonium Acetate for 30 secs run time.

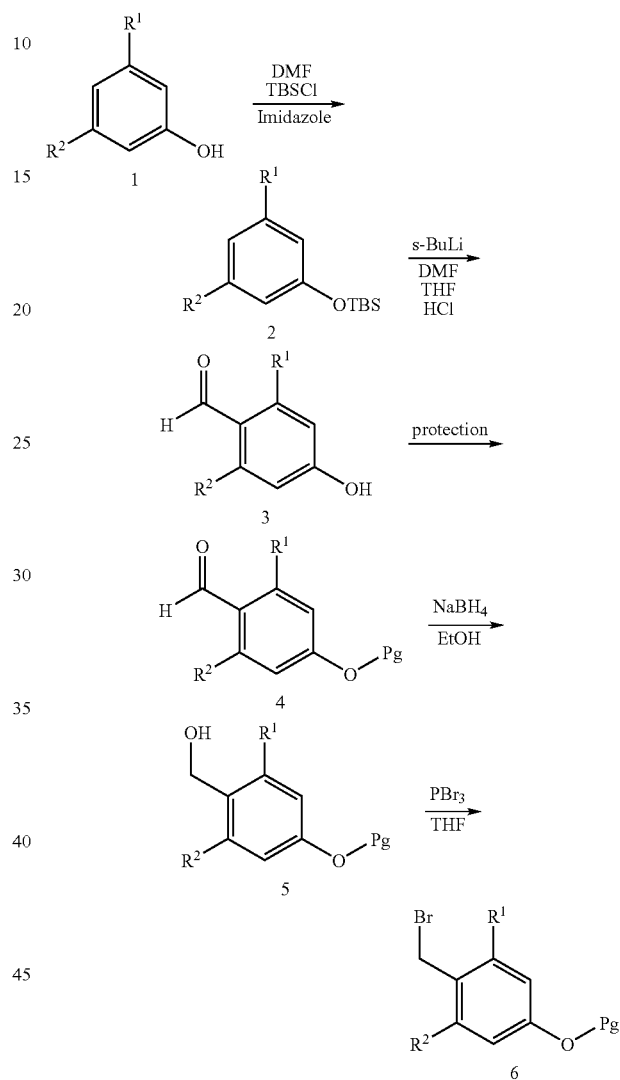

Scheme A

In Scheme A, an optionally substituted phenol (1) is protected (e.g, with TBSCl) to form compound 2, and then compound 2 is converted to the aldehyde (3). Compound 3 is reacted with a compound containing a protecting group (Pg) and leaving group (Lg) to give the ether compound 4. Pg can be —CH$_3$ or —CH$_2$-phenyl and Lg can be mesylate or halo. Preferably, the Lg-Pg compound is I—CH$_3$ or Br—CH$_2$-phenyl. The aldehyde is reduced to form the alcohol (5) and then converted to compound 6. Preferably, compound 5 is halogenated with PBr$_3$ to give the 2-bromo-methyl compound.

Protection and deprotection of the compounds to form compounds of formula I and others are well known to the skilled artisan and are described in the literature. (For example, see: Greene and Wuts, *Protective Groups in Organic Synthesis*, Third Edition, John Wiley and Sons Inc., 1999).

Scheme B
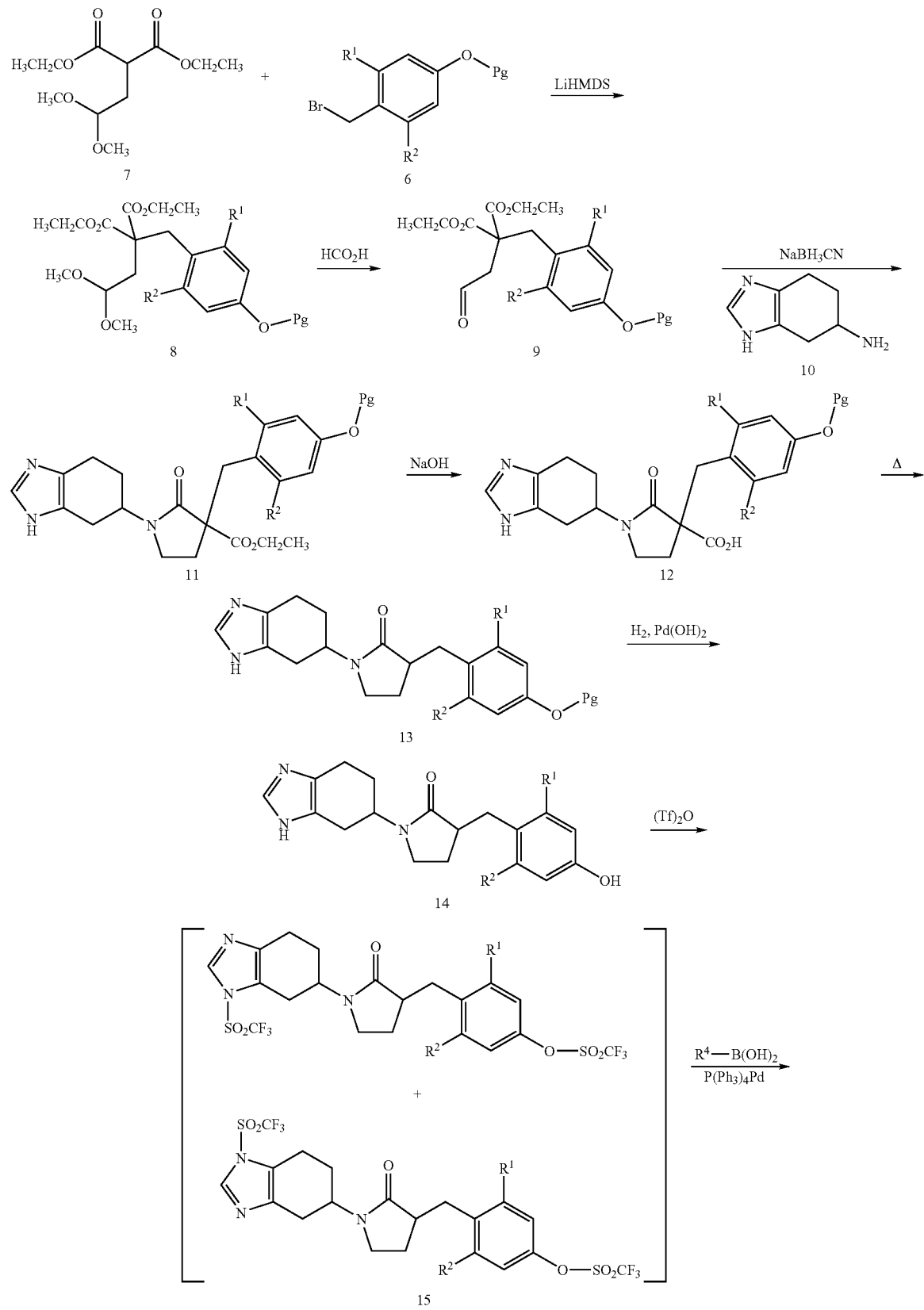

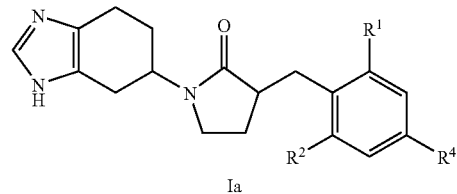

Ia

In Scheme B, a compound of formula Ia is formed by first reacting compound 7 with compound 6 (Scheme A) to form compound 8. Then, the dimethoxy compound 8 is converted to the aldehyde (9). Compound 9 is reacted with the tetrahydro-benzoimidazol-5-ylamine (10) to form the racemic lactam (11) which is then converted to the compound 13. Compound 13 is deprotected to form the phenol (14). Compound 14 is converted into the pair of isomers (15) by reacting with trifluoromethanesulfonic anhydride. A coupling reaction is performed on 15 using a boronic acid reagent ($R^4$—$B(OH)_2$) and a catalyst, such as tetrakis(triphenylphosphene)palladium(0).

Scheme C

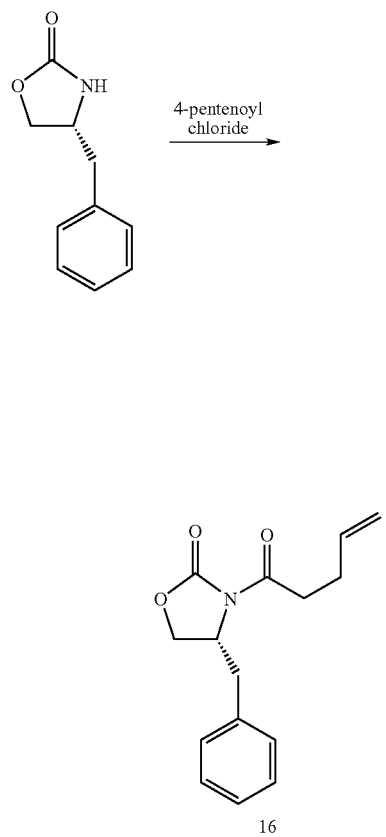

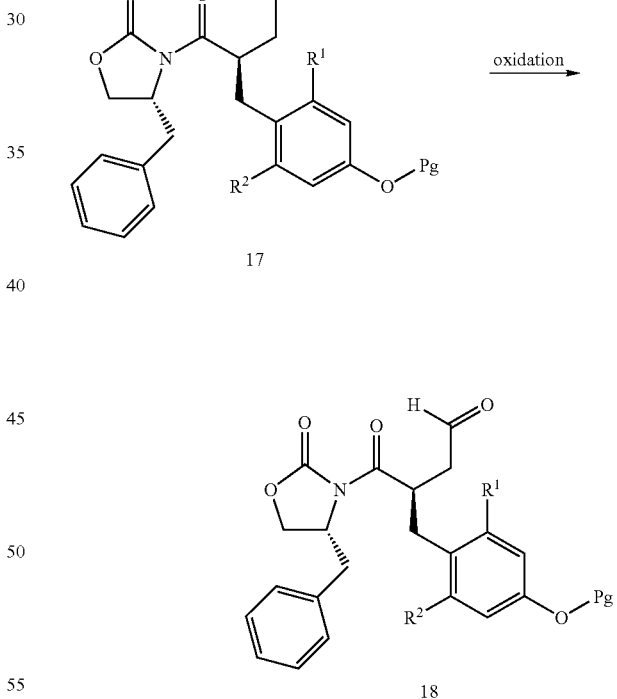

Scheme C shows the stereo selective synthesis to form the intermediate compound 18. Compound 16 is formed by acylating commercially available (R)-4-benzyl-oxazolidin-2-one with 4-pentenoyl chloride. It is then alkylated with an optionally substituted compound 6 (see Scheme A) to give compound of 17. Compound 17 is oxidized to form the aldehyde intermediate compound 18 using ozone and triphenylphosphine or osmium tetroxide and an oxidant such as sodium metaperiodate.

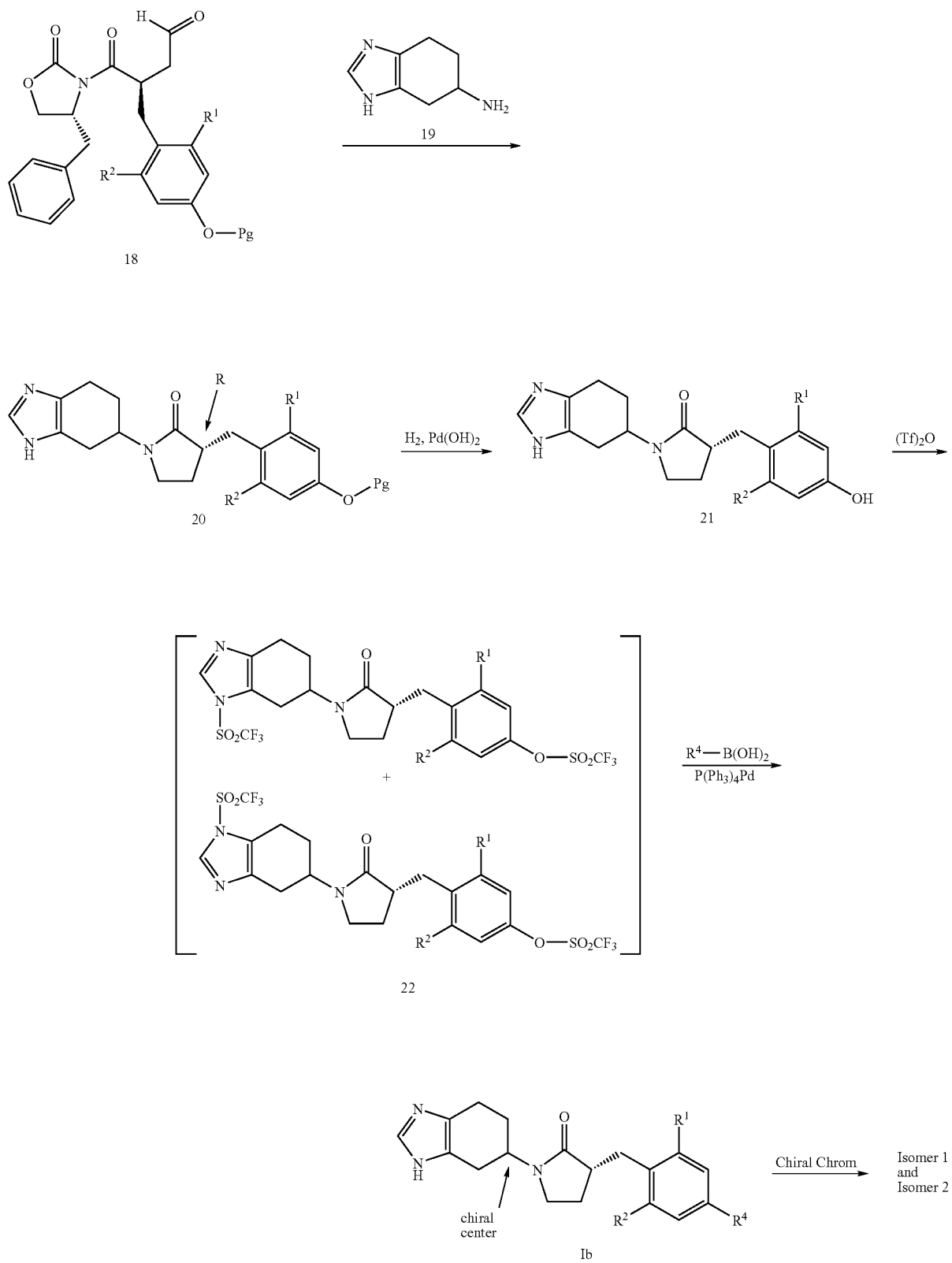

In Scheme D, the intermediate (18) is converted to the lactam compound 20 which is in the "R" configuration. A deprotection is performed to give compound 21 which is then trfliated (trifluoromethanesulfonic anhydride) to form the isomer pair (22). A coupling reaction is performed on 22 using a boronic acid reagent ($R^4$—$B(OH)_2$) and a catalyst, such as tetrakis(triphenylphosphene)palladium(0).

Scheme E

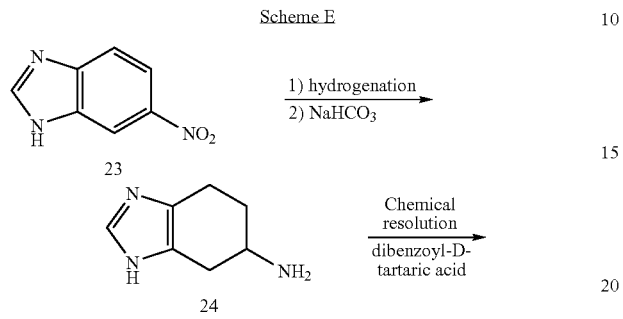

-continued

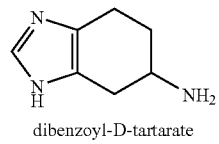

dibenzoyl-D-tartarate
25

In Scheme E, nitrobenzimidazol (23) is hydrogenated to form racemic 4,5,6,7-tetrahydro-3H-benzoimidazol-5-ylamine (24). Then, compound 25 is resolved by fractional crystallization using dibenzoyl-D-tartarate. (Siegfried Schwarz and Walter Schunack; Arch. Pharm. vol 312, pp 933-939, year 1979).

Scheme F

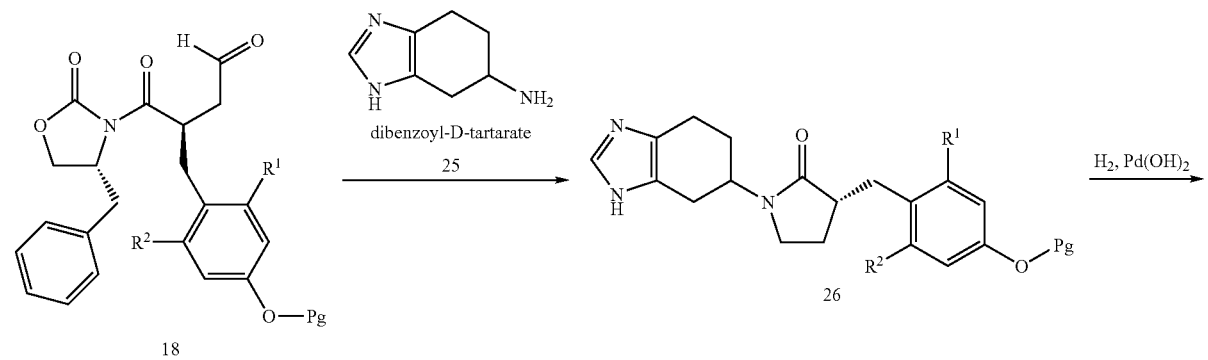

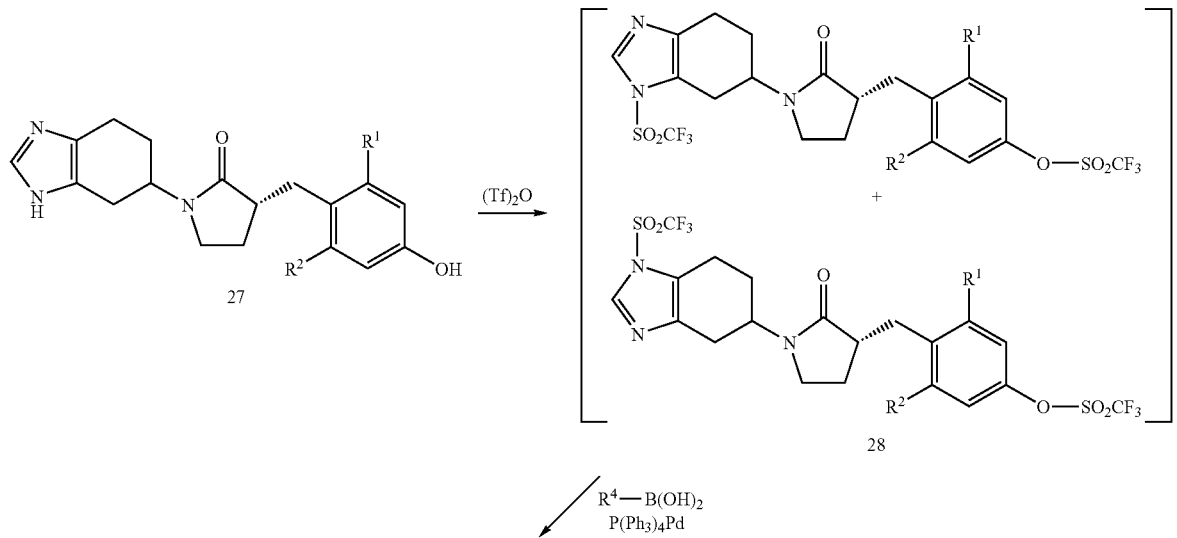

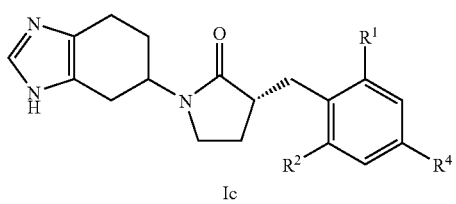

Ic

In Scheme F, the intermediate (18) is reacted with resolved compound 25 (Scheme E) to form the lactam compound 26 which is in the "R" configuration. A deprotection is performed to give compound 27 which is then trfliated (trifluoromethanesulfonic anhydride) to form the isomer pair (28). A coupling reaction is performed on 28 using a boronic acid reagent ($R^4$—B(OH)$_2$) and a catalyst, such as tetrakis(triphenylphosphene)palladium(0).

Preparation 1

2,6-dichloro-4-hydroxy-benzaldehyde

Dissolve 3,5 dichlorophenol (1 kg, 6.13 mol) in 3 L dimethylformamide (DMF) and cool to 0° C. Add imidazole (918.74 g, 6.75 mol), followed by tertbutyldimethylsilyl chloride (1017.13 g, 6.75 mol). Warm the mixture to room temperature and stir for 15 minutes. Pour into water (6 L) and extract with ether (4 L). Wash the organic layer with water 2 times, 10% aqueous lithium chloride solution then brine before drying over sodium sulfate. Filter and concentrate under vacuum to obtain tert-butyl-(3,5-dichloro-phenoxy)-dimethyl-silane (1700 g) as an oil.

Dissolve tert-butyl-(3,5-dichloro-phenoxy)-dimethyl-silane (425 g, 1.5 mol) in 4 L dry tetrahydrofuran and cool to −68° C. Slowly add 1.1 equivalents of sec-butyl lithium (103.1 g, 1.61 mol) at −68° C. (~1.75 hr). After addition is complete stir the reaction at −70° C. for 30 min. Add dimethylformamide (168.5 g, 2.3 mol) and stir the reaction at −70° C. for 1 hr. Add 1 M hydrochloric acid in water (3.5 L) and allow the reaction to warm to room temperature.

Pour the reaction mixture into ether (5 L), wash with water then brine. Dry over sodium sulfate and concentrate under vacuum to an orange solid. Triturate with cold dichloromethane and filter to recover 250 g (80%) pale yellow solid.

Preparation 2

2,6-dichloro-4-methoxy-benzaldehyde

Combine 2,6-dichloro-4-hydroxy-benzaldehyde (120 g, 628.24 mmol) and potassium carbonate (173.65 g, 1256.5 mmol) in 900 mL dimethylformamide and treat with iodomethane (107 g, 753.9 mmol). Stir the reaction at room temperature for 3 hours. Filter off solids and pour into 6 L of water. Filter solids, wash several times with water, air dry and dissolve in ethyl acetate. Wash with water, followed by brine and then dry over sodium sulfate. Filter and concentrate under vacuum to 100 mL volume, at which point, solids start to crash out. Filter then concentrate down the filtrate to yield a second crop. Wash with hexane, combine all solids and vacuum dry to yield 112.3 g of off-white, solid: $^1$H NMR (400 MHz, CDCl$_3$) δ 10.41 (s, 1H), 6.90 (s, 2H), 3.87 (s, 3H).

Preparation 3

2,6-dichloro-4-benzyloxy-benzaldehyde

Treat a mixture of 2,6-dichloro-4-hydroxy-benzaldehyde (250 g, 1.3 mol) and potassium carbonate (361.8 g, 2.62 mol) in 2 L dimethylformamide with benzyl bromide (268.64 g, 1.57 mol). Stir the reaction at room temperature for 1 hour. Filter off solids and pour into 12 L of water. Filter off solid, wash several times with water, air dry and dissolve in ethyl acetate. Dry over magnesium sulfate, filter and concentrate under vacuum to ~1.5 L. Allow to sit overnight then filter. Wash solid with minimal amount of hexane and vacuum dry. Concentrate the filtrate under vacuum and triturate with hexane to yield a second crop of product which when combined with the first crop equals 245 g white crystals. Repeat to obtain a 3rd crop of 80 g as a light-tan powder (88% overall yield): $^1$H NMR (400 MHz, DMSO-d6) δ 10.26 (s, 1H), 7.43 (m, 5H), 7.28 (s, 2H), 5.25 (s, 2H).

Preparation 4

(2,6-dichloro-4-methoxy-phenyl)-methanol

Suspend 2,6-dichloro-4-methoxy-benzaldehyde (112 g, 546 mmol) in 1500 mL ethanol and cool in an ice bath to 7° C. Add sodium borohydride (20.67, 546 mmol) portionwise to obtain a solution. Remove the ice bath and stir for 2 hours. Carefully add reaction mixture to saturated ammonium chloride solution (~4 L) and stir until fully quenched. Extract with dichloromethane (3×1 L) and dry the combined organic extracts over sodium sulfate. Filter and concentrate under vacuum to yield 113 g of a light-tan solid: $^1$H NMR (400 MHz, CDCl$_3$) δ 6.86 (s, 2H), 4.86 (s, 2H), 3.78 (s, 3H), 2.07 (s, 1H).

Preparation 5

(2,6-dichloro-4-benzyloxy-phenyl)-methanol

Prepare the title compound essentially as prepared by the method of Preparation 4. NMR (DMSO-d$_6$) δ 7.38 (m, 4H), 7.33 (m, 1H), 7.12 (s, 2H), 5.14 (s, 2H), 5.05 (t, 1H), 4.59 (d, 2H).

Preparation 6

2-bromomethyl-1,3-dichloro-5-methoxy-benzene

Dissolve (2,6-dichloro-4-methoxy-phenyl)-methanol (113 g, 545.76 mmol) in 1200 mL dry THF and cool to 0 deg under nitrogen. Add PBr$_3$ (59.1 g, 218.3 mmol) under nitrogen and stir at 0° C. for 30 minutes. Pour into saturated aqueous NaHCO₃ and extract with EtOAc. Dry and concentrate under vacuum to obtain 129.4 g product as an off-white solid. NMR (CDCl₃) δ 6.88 (s, 2H), 4.73 (s, 2H), 3.79 (s, 3H).

Preparation 7

2-bromomethyl-1,3-dichloro-5-benzyloxy-benzene

Prepare the title compound essentially as prepared by the method of Preparation 6 in an 89% yield. ES MS (m/z): 347 (M+1).

Preparation 8

4,5,6,7-tetrahydro-3H-benzoimidazol-5-ylamine dihydrochloride

Add 5% Rh/C (5.215 g) to a 500 ml glass Parr bottle. Purge the bottle with nitrogen and wet the 5% Rh/C with 3 N HCl (50 ml). Then add 6-nitro-1H-benzoimidazole (10.354 g, 0.0635 mol) and 3N HCl (100 ml) to the purged bottle. Seal the Parr bottle and purge the reaction vessel with nitrogen (3×) and with hydrogen (3×). Then pressurize the reaction mixture with hydrogen (60 psig), seal the vessel but add hydrogen as needed to maintain 60 psig, agitate the reaction and heat to 80° C. Continue the reaction for 24 hours then turn off the heat and allow the reaction mixture to cool to ambient temperature. Vent the excess hydrogen from the vessel, purge the vessel with nitrogen (3×) and filter the reaction mixture to remove the 5% Rh/C catalyst. The filtrate is concentrated to dryness on a rotary evaporator and then under high vacuum. Dissolve the solid residue in 20 mL of methanol, heat to approximately 60° C. and add additional methanol (approximately up to 10 mL or as needed) to dissolve the residue completely. Cool the solution to room temperature and add ether (40 mL). A white solid separates, filter and dry under high vacuum to give the product (8.gm).
¹H NMR (D₂O): δ 1.80-2.11 (1H), 2.09-2.22 (1H), 2.60-2.79 (4H), 3.01-3.15 (1H), 3.61-3.75 (1H), 8.41 (1H).

Preparation 9

2-(4-benzyloxy-2,6-dichloro-benzyl)-2-(2,2-dimethoxy-ethyl)-malonic acid diethyl ester Cool 2-(2,2-Dimethoxy-ethyl)-malonic acid diethyl ester (4.5 g, 16.3 mmol) in 50 mL THF to −78° C. and add lithium hexamethylsilane amide (1M, 17 mL) drop wise. After 15 min, add 5-benzyloxy-2-bromomethyl-1,3-dichloro-benzene (17.9 mmol 6.2 g) in 10 mL THF. Warm this mixture to ambient temperature, acidify with 1N HCl, and extract with ethyl acetate. Concentrate the organics and purify by normal phase column chromatography to afford the title compound as a white solid (7.0 g, 80%).

Preparation 10

2-(4-benzyloxy-2,6-dichloro-benzyl)-2-(2-oxo-ethyl)-malonic acid diethyl ester

To a solution of 2-(4-benzyloxy-2,6-dichloro-benzyl)-2-(2,2-dimethoxy-ethyl)-malonic acid diethyl ester (10.0 g, 18.5 mmol) (Preparation 9) in 95 mL of acetone, add 10 ml of formic acid. After 24 h, concentrate the reaction to 2-(4-benzyloxy-2,6-dichloro-benzyl)-2-(2-oxo-ethyl)-malonic acid diethyl ester as yellow oil product (6.7 g, 80%).

Preparation 11

3-(4-benzyloxy-2,6-dichloro-benzyl)-2-oxo-1-(4,5,6,7-tetrahydro-3H-benzoimidazol-5-yl)-pyrrolidine-3-carboxylic acid ethyl ester Add sodium cyanoborohydride (3.6 g, 57.4 mmol) portion wise to a solution of 2-(4-benzyloxy-2,6-dichloro-benzyl)-2-(2-oxo-ethyl)-malonic acid diethyl ester (6.7 g, 14.4 mmol) (Preparation 10) and 4,5,6,7-tetrahydro-3H-benzoimidazol-5-ylamine dihydrochloride salt (6.0 g, 28.7 mmol) (Preparation 1) in 70 ml of Methanol. After 3 h, add 4 ml of acetic acid and warm to 60° C. for 16 h. Most of the Methanol is removed via rotovap. Quench the resulting mixture with saturated bicarbonate and extract with ethyl acetate. Dry extracts over sodium sulfate, concentrate, and purify by normal phase column chromatography (0-10% methanol in ethyl acetate) to afford 3-(4-Benzyloxy-2,6-dichloro-benzyl)-2-oxo-1-(4,5,6,7-tetrahydro-3H-benzoimidazol-5-yl)-pyrrolidine-3-carboxylic acid ethyl ester as a white solid (3 g).

Preparation 12

3-(4-Benzyloxy-2,6-dichloro-benzyl)-1-(4,5,6,7-tetrahydro-3H-benzoimidazol-5-yl)-pyrrolidin-2-one Dissolve 3-(4-Benzyloxy-2,6-dichloro-benzyl)-2-oxo-1-(4,5,6,7-tetrahydro-3H-benzoimidazol-5-yl)-pyrrolidine-3-carboxylic acid ethyl ester (3 g, 5.5 mmol) (Preparation 11) in 10 ml of Methanol and then add 10 ml of 2N NaOH. Stir this mixture for 16 h, concentrate, and then add dioxane and acetic acid to obtain 3-(4-Benzyloxy-2,6-dichloro-benzyl)-2-oxo-1-(4,5,6,7-tetrahydro-3H-benzoimidazol-5-yl)-pyrrolidine-3-carboxylic acid which is not isolated. Reflux the mixture overnight, quench with water and extract with ethyl acetate. Wash the extracts with saturated bicarbonate and concentrate to 3-(4-Benzyloxy-2,6-dichloro-benzyl)-1-(4,5,6,7-tetrahydro-3H-benzoimidazol-5-yl)-pyrrolidin-2-one product (2.6 g). MS: m/z (M+1)=470.

Preparation 13

3-(2,6-Dichloro-4-hydroxy-benzyl)-1-(4,5,6,7-tetrahydro-1H-benzoimidazol-5-yl)-pyrrolidin-2-one Add palladium hydroxide to a nitrogen purged solution of 3-(4-Benzyloxy-2,6-dichloro-benzyl)-1-(4,5,6,7-tetrahydro-1H-benzoimidazol-5-yl)-pyrrolidin-2-one (4.3 g, 9.2 mmol) (Preparation 12) in 50 ml of ethyl acetate and 15 ml of methanol. Add about 22 psi of pressurized nitrogen and stir for 16 h. Filter this mixture and concentrate to afford 3-(2,6-Dichloro-4-hydroxy-benzyl)-1-(4,5,6,7-tetrahydro-1H-benzoimidazol-5-yl)-pyrrolidin-2-one as solid product (2 g). MS: m/z (M+1)=380.

Preparation 14

Trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-ylmethyl]-phenyl and trifluoro-methanesulfonic acid 3,5-dichloro-4-[2-oxo-1-(1-trifluoromethanesulfonyl-4,5,6,7-tetrahydro-3H-benzimidazol-5-yl)-pyrrolidin-3-ylmethyl]-phenyl esters

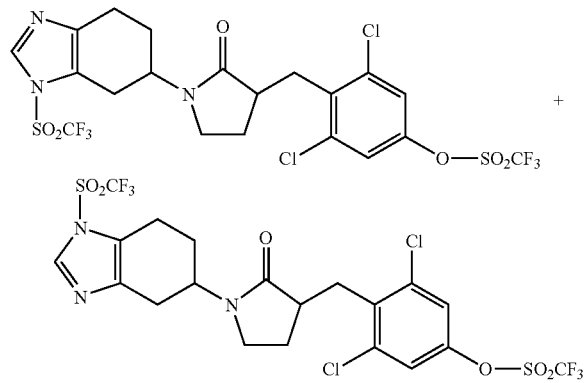

Take up 3-(2,6-dichloro-4-hydroxy-benzyl)-1-(4,5,6,7-tetrahydro-3H-benzimidazol-5-yl)-pyrrolidin-2-one (0.5 g) (Preparation 13) in DCM (2 mL) and pyridine (2 mL). Cool the solution to 0° C. in ice bath and add trifluoromethanesulfonic anhydride (0.5 mL) dropwise with stirring. The reaction mixture is then left standing −30° C. for overnight in a freezer. Dilute the reaction mixture with ethyl acetate (50 mL). Wash with 1M aqueous HCl (2×50 mL), brine (50 mL). Dry the ethyl acetate layer over sodium sulfate and concentrate on a rotary evaporator. Drying the residue under high vacuum gives mixtures of trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-ylmethyl]-phenyl and trifluoro-methanesulfonic acid 3,5-dichloro-4-[2-oxo-1-(1-trifluoromethanesulfonyl-4,5,6,7-tetrahydro-3H-benzimidazol-5-yl)-pyrrolidin-3-ylmethyl]-phenyl esters as a yellow foamy solid (650 mg). Proceed to the next step without purification. MS: m/z (M+1)=643.

Preparation 15

(R)-4-benzyl-3-pent-4-enoyl-oxazolidin-2-one

Flush with nitrogen a 12 L 3-neck round bottom flask equipped with a mechanical stirrer, internal temperature probe/$N_2$ inlet, and 1 L addition funnel for 20 min and then add (R)-4-benzyl-2-oxazolidinone (250 g, 1.41 mol). Dilute with tetrahydrofuran (THF) (1.8 L) and cool in a dry ice/acetone bath until the internal temperature is −74° C. Transfer a 1.6M hexanes solution of n-butyllithium (970 mL, 1.552 mol) to the addition funnel via cannula, and add to the oxazolidinone solution at a rate such that the internal temperature does not reach above −65° C. After the addition is complete, allow the reaction to stir in the cooling bath 30 min. Transfer 4-pentenoyl chloride (175 mL, 1.585 mol) to the addition funnel and add dropwise to the anion solution over a 25 min period. Stir the reaction for 45 min in the cooling bath. Remove the cooling bath and stir the reaction 18 hr as it slowly reaches room temperature. Dilute the mixture with 1N aqueous hydrochloric acid (1.5 L) and diethyl ether (1 L). Separate the layers and wash the organic phase with water (2×1 L) then brine (1 L). Extract the combined aqueous washes with ether (1 L). Dry the combined organic phases over anhydrous magnesium sulfate, filter, and concentrate to 390 g of a light tan oil. Purify this material by silica gel chromatography using hexanes:ethyl acetate to obtain 345 g (94.5%) of a clear, yellow oil.

Preparation 16

(R)-4-Benzyl-3-[(S)-2-(4-benzyloxy-2,6-dichloro-benzyl)-pent-4-enoyl]-oxazolidin-2-one Stir a mixture of (R)-4-benzyl-3-pent-4-enoyl-oxazolidin-2-one (345 g, 1.33 mol) and THF (1.8 L) in a 12 L 3-neck round bottom flask, with internal temperature probe/nitrogen inlet and addition funnel, under a nitrogen atmosphere and cool to −75° C. Transfer 1 M LiHMDS (1.6 L) to the addition funnel and add at a rate such that the internal temperature does not reach above −60° C. After the addition is complete, allow the reaction to stir at −25° C. for 30 min then cool to about −60° C. At this point add solid 2-bromomethyl-1,3-dichloro-5-benzyloxy-benzene portionwise over 5 min. After the addition is complete, transfer the reaction vessel to a −10° C. acetone bath and maintain the internal reaction temperature below 10° C. for 1 hr. Cool the mixture to 0° C. then quench with 2 L aqueous 1N hydrochloric acid. Transfer the mixture to a 22 L separatory funnel and dilute with 2.5 L water and 2 L ether. Separate the layers and extract the aqueous layer with ether. Dry the combined organic phase over anhydrous magnesium sulfate, filter and concentrate to 800 g of a thick oil. Purify by silica gel chromatography using hexanes:ethyl acetate to obtain 597 g, (86%) of a colorless oil.

Preparation 17

(R)-4-((R)-4-Benzyl-2-oxo-oxazolidin-3-yl)-3-(4-benzyloxy-2,6-dichloro-benzyl)-4-oxo-butyraldehyde Cool a mixture of (R)-4-Benzyl-3-[(S)-2-(4-benzyloxy-2,6-dichloro-benzyl)-pent-4-enoyl]-oxazolidin-2-one (100 g, 190.68 mmol) and dichloromethane (800 mL) to −74° C. Bubble ozone, produced via the A-113 ozone generator at a rate of 75%, through the reaction via carrier air at a rate of 5 CFM until the solution takes on a blue color (approx 3 hr). Add triphenylphosphine (60 g, 228.8 mmol) as a solution in 200 mL dichloromethane and allow the reaction to stir while reaching room temperature over night. Concentrate the solution under vacuum and purify by silica gel chromatography using a gradient of 20-50% ethyl acetate in hexanes to obtain 82.1 g (82%) of the product as a white foam: MS (m/z): 526 (M+).

Alternate procedure for making (R)-4-((R)-4-Benzyl-2-oxo-oxazolidin-3-yl)-3-(4-benzyloxy-2,6-dichloro-benzyl)-4-oxo-butyraldehyde:

Treat a mixture of (R)-4-Benzyl-3-[(S)-2-(4-benzyloxy-2,6-dichloro-benzyl)-pent-4-enoyl]-oxazolidin-2-one (0.96 g, 1.8 mmol), THF (21 mL) and water (7 mL) with 2.5% osmium tetroxide in t-butanol (46 mg, 0.18 mmol). Add sodium periodate (1.17 g, 5.5 mmol) and stir the reaction 4 hr at room temperature. Quench the reaction with water and extract with ethyl acetate. Wash the organic phase with aqueous 1N sodium thiosulfate then brine. Dry the organic layer over magnesium sulfate, filter, and concentrate under vacuum. Purify the crude material by silica gel chromatography using hexanes:ethyl acetate to elute the pure product. Concentrate the fractions containing product under vacuum to afford 0.46 g (48%) of desired product. MS (m/z): 526 (M+).

Preparation 18

3-[R]-(4-benzyloxy-2,6-dichloro-benzyl)-1-(4,5,6,7-tetrahydro-3H-benzimidazole-3-yl)-pyrrolidin-2-one Add Preparation 10 (5.25 g) to a suspension of imidazolocyclohexy-3-amine hydrochloride (2 gm) (Preparation 8) in methanol (30 mL). Stir the mixture at room temperature for 30 min. Add sodium cyanoborohydride (1 g) and stir the mixture for 2 h. Heat the reaction mixture at 50° C. for 2 h. Dilute the reaction mixture with ethyl acetate (50 mL) and wash the mixture with water (50 mL). Dry ethyl acetate layer over sodium sulfate and concentrate on rotary evaporator to give a crude. Purify the crude by silica flash chromatography eluting with a gradient of 0-5% methanol in DCM to give the product as a mixture of diastereomers, 3-(4-benzyloxy-2,6-dichloro-benzyl)-1-(4,5,6,7-tetrahydro-3H-benzimidazole-3-yl)-pyrrolidin-2-one (4.5 gm). MS: m/z=470 (M+1).

Preparation 19

3-[R]-(2,6-dichloro-4-hydroxy-benzyl)-1-(4,5,6,7-tetrahydro-3H-benzimidazol-5-yl)-pyrrolidin-2-one Take up 3-(4-benzyloxy-2,6-dichloro-benzyl)-1-(4,5,6,7-tetrahydro-3H-benzimidazole-3-yl)-pyrrolidin-2-one (2.5 g) (Preparation 18) in methanol (50 mL) and ethylacetate (30 mL) in a pressure bottle. Add palladium hydroxide catalyst (500 mg) and stir the reaction mixture under hydrogen atmosphere (30 psi) at 40° C. for over night. Filter the reaction mixture over celite. Concentrate filtrate to give the product, 3-[R]-(2,6-dichloro-4-hydroxy-benzyl)-1-[R/S]-(4,5,6,7-tetrahydro-3H-benzimidazol-5-yl)-pyrrolidin-2-one a white solid (1.6 gm) as mixture. MS: m/z=379 (M+1).

Preparation 20

Trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-[R]-ylmethyl]-phenyl and trifluoro-methanesulfonic acid 3,5-dichloro-4-[2-oxo-1-(1-trifluoromethanesulfonyl-4,5,6,7-tetrahydro-3H-benzimidazol-5-yl)-pyrrolidin-3-[R]-ylmethyl]-phenyl esters (13).

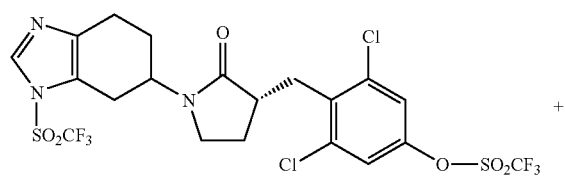

-continued

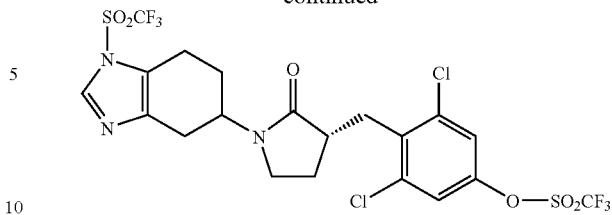

Take up 3-[R]-(2,6-dichloro-4-hydroxy-benzyl)-1-(4,5,6,7-tetrahydro-3H-benzimidazol-5-yl)-pyrrolidin-2-one (1.6 g) (Preparation 19) in DCM (20 mL) and pyridine (5 mL). Cool the solution to −78° C. and add trifluorosulfonic anhydride (3 mL) drop wise with stirring. The reaction mixture is then left standing for 48 h in a freezer. Dilute the reaction mixture with ethyl acetate (150 mL). Wash with 1M aqueous HCl (2×50 mL), brine (50 mL). Dry the ethyl acetate layer over sodium sulfate and concentrate on a rotary evaporator. Drying the residue under high vacuum to gives mixtures of trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-ylmethyl]-phenyl and trifluoro-methanesulfonic acid 3,5-dichloro-4-[2-oxo-1-(1-trifluoromethanesulfonyl-4,5,6,7-tetrahydro solid (2.01 g). The mixture is carried on to next step without purification. MS: m/z (M+1)=643.

Preparations 21 and 22

Chiral purification of 3-[R]-(4-benzyloxy-2,6-dichloro-benzyl)-1-(4,5,6,7-tetrahydro-3H-benzimidazole-3-yl)-pyrrolidin-2-one Purify diastereoisomeric mixture of 3-(4-benzyloxy-2,6-dichloro-benzyl)-1-(4,5,6,7-tetrahydro-3H-benzimidazole-3-yl)-pyrrolidin-2-one (2 gm) (Preparation 18) on a Chiralpak AD-H (0.46×15 cm) column eluting with 60:40:0.2 3A ethanol/heptane/DMEA (Flow=0.6 mL/min.) to give:
Isomer 1 (Preparation 21), Ret time 5.4 min, 922 mg) and
Isomer 2 (Preparation 22), Ret time 7.1 min, 866 mg.

Use Isomer 2 for Preparation 23.

Preparation 23

4,5,6,7-Tetrahydro-3H-benzoimidazol-5-ylamine dibenzoyl-D-tartric acid (Siegfried Schwarz and Walter Schunack; Arch. Pharm. vol 312, pp 933-939, year 1979). Dissolve 4,5,6,7-Tetrahydro-1H-benzoimidazol-5-ylamine dihydrochloride salt (42 g, 200 mmol) (Preparation 8) into 350 ml H$_2$O. Add to this solution sodium bicarbonate (50 g, 600 mmol) portion wise until bubbling ceases. Heating to 60° C. may be needed for complete quenching of the salt. The final pH is 10. Concentrate this aqueous mixture and dry on a vacuum pump overnight. Add warm ethanol (400 ml) and stir to break up the salt solids and filter. Repeat the extraction again. Mechanical stirring or stirring overnight may be needed to break up all the solids sufficiently. Concentrate the ethanol extractions to 800 ml and add 400 ml H$_2$O and dibenzyl-D-tartaric acid (75 g, 210 mmol). Solids form within 10-15 min. Allow this mixture to stir overnight. Filter solids to give 4,5,6,7-Tetrahydro-3H-benzoimidazol-5-ylamine dibenzoyl-D-tartrate which is re-crystallized by dissolving the material in methanol (350 mL)

by heating at 50-60° C. in a conical flask by continuous stirring. Add additional methanol as need to dissolve all material. Add water (20 mL) while the mixture is hot. Cool the mixture down to room temp with stirring which results in separation of white solid suspension. Filter the solid and dry to give enriched amino cyclohexylimidazole dibenzyl-D-tartaric acid salt. Repeat the re-crystallization procedure an additional three times to give an enriched material. Yield=25.4 g, ee~92%.

Preparation 24

3-[R]-(4-benzyloxy-2,6-dichloro-benzyl)-1-(4,5,6,7-tetrahydro-3H-benzimidazole-3-yl)-pyrrolidin-2-one Add Preparation 17 (4.87 g) to a suspension of 4,5,6,7-Tetrahydro-3H-benzoimidazol-5-ylamine dibenzoyl-D-tartric acid (Preparation 23) in methanol (20 mL). Stir the mixture at room temperature for 30 min. Add sodium cyanoborohydride (0.75 g) and stir the mixture for 2 h. Heat the reaction mixture at 50° C. for 2 h. Dilute the reaction mixture with DCM (200 mL) and wash the mixture with saturated sodium bicarbonate solution (2×100 mL), and then with water (100 mL). Dry DCM layer over sodium sulfate and concentrate on the rotoevaporator to give crude. Purify the crude by silica flash chromatography eluting with a gradient of 0-5% methanol in DCM to give the title compound (3.35 gm). MS: m/z (M+1)=470.

Preparation 25

3-[R]-(2,6-dichloro-4-hydroxy-benzyl)-1-(4,5,6,7-tetrahydro-3H-benzimidazol-5-yl)-pyrrolidin-2-one Take up 3-[R]-(4-Benzyloxy-2,6-dichloro-benzyl)-1-(4,5,6,7-tetrahydro-3H-benzimidazole-3-yl)-pyrrolidin-2-one (3.35 g) (Preparation 24) in methanol (30 mL) and ethyl acetate (20 mL) in a pressure bottle. Add palladium hydroxide catalyst (500 mg) and stir the reaction mixture under hydrogen atmosphere (30 psi) at 40° C. for 4 h and then at room temperature overnight. Filter the reaction mixture over celite. Concentrate filtrate to give the title compound as a white solid (2.69 gm). MS: m/z=379 (M+1).

Preparation 26

Trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-[R]-ylmethyl]-phenyl and trifluoro-methanesulfonic acid 3,5-dichloro-4-[2-oxo-1-(1-trifluoromethanesulfonyl-4,5,6,7-tetrahydro-3H-benzimidazol-5-yl)-pyrrolidin-3-[R]-ylmethyl]-phenyl esters

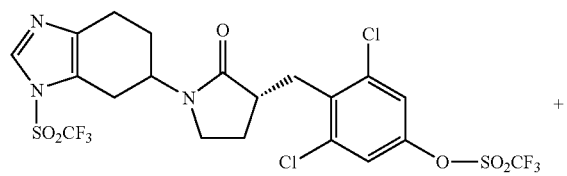

+

-continued

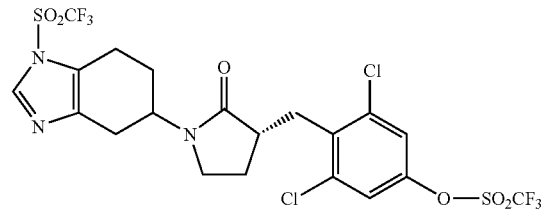

Take up 3-[R]-(2,6-dichloro-4-hydroxy-benzyl)-1-(4,5,6,7-tetrahydro-3H-benzimidazol-5-yl)-pyrrolidin-2-one (Preparation 25) (2.5 g) in DCM (10 mL) and pyridine (10 mL). Cool the solution to −78° C. and add trifluorosulfonic anhydride (4 mL) drop wise with stirring. The reaction mixture is then left standing overnight. Dilute the reaction mixture with ethyl acetate (150 mL). Wash with 1M aqueous HCl (2×100 mL), brine (100 mL). Dry the ethyl acetate layer over sodium sulfate and concentrate on a rotary evaporator. Drying the residue under high vacuum gives the title compound mixture as a yellow foamy solid (3.4 g).

Preparation 27

Ethyl 2-(4-bromo-2-chlorobenzyl)-4-oxobutanoate

Add sodium periodate (41 g, 190 mmol) into a solution of ethyl 2-(4-bromo-2-chlorobenzyl)pent-4-enoate (21 g, 63 mmol), 2.5 wt % OsO₄ (64 g, 6.3 mmol) in THF (400 mL) and water (160 mL) and stir for 2 hours. Extract the reaction mixture with ethyl acetate, wash the organic layer with sodium thiosulfate solution and brine. Dry over sodium sulfate, filter and concentrate. Purify the residue with silica gel column to afford the title compound (15.9 g, 75%) as colorless oil.

Preparation 28

(4R,5S)-(cis)-3-Pent-4-enoyl-4,5-diphenyl-oxazolidin-2-one

Dissolve (4R,5S)-(+)-cis-4,5-diphenyl-2-oxazolidin-one (2.06 g, 8.62 mmol) in THF (100 mL) and cool to −78° C. Add n-BuLi (5.66 mL, 9.05 mmol, 1.6 M in hexane) and stir for 30 minutes. Then add pent-4-enoyl chloride (1.53 g, 12.93 mmol) and continue stir the solution for one hour. Add water (100 mL) and extract the aqueous layer with ethyl acetate (3×200 mL). Combine the organic layers and dry with Na₂SO₄, filter, concentrate and purify by flash column chromatography (silica gel, 20-40% of EtOAc-hexane) to give 1.42 g (51%) of the title compound as a white solid.

Preparation 29

3-Benzyl-1-cyclohexyl-pyrrolidin-2-one

Place 1-cyclohexyl-pyrrolidin-2-one (400 mg, 2.4 mmol) in THF (30 mL) and cool to −78° C. Slowly add LDA (2.0 M, 2.4 mL, 4.8 mmol) and stir for 15 minutes. Add benzyl bromide (1.23 g, 7.2 mmol) and stir for 3 hours. Quench with ammonium chloride and extract with dichloromethane. Dry over sodium sulfate, filter, and concentrate. Purify by silica gel (20-50% ethyl acetate in hexanes) to afford 432 mg (70%) of the title compound. Mass spectrum (apci) m/z=258.2 (M+H).

Preparation 30

(4R,5S)-(cis)-3-[2-(S)-(2-Chloro-6-fluoro-benzyl)-pent-4-enoyl]-4,5-diphenyl-oxazolidin-2-one Using the procedure to synthesize Preparation 29, alkylation of (4R,5S)-(cis)-3-pent-4-enoyl-4,5-diphenyl-oxazolidin-2-one (1.48 g, 6.61 mmol) with 2-bromomethyl-1-chloro-3-fluoro-benzene affords 1.28 g (62%) of the title compound as a white solid.

Preparation 31

(4R,5S)-(cis)-3-(2-(R)-Chloro-6-fluoro-benzyl)-4-oxo-4-(2-oxo-4,5-diphenyl-oxazolidin-3-yl)-butyraldehyde Dissolve (4R,5S)-(cis)-3-[2-(S)-(2-chloro-6-fluoro-benzyl)-pent-4-enoyl]-4,5-diphenyl-oxazolidin-2-one (1.28 g, 2.75 mmol) in dichloromethane (100 mL) and cool to 0° C. Bubble ozone into the solution with stirring until the solution becomes blue. Continue to stir the solution for one hour, then bubble nitrogen through the mixture until the blue color disappears. Add Me$_2$S (0.85 g, 13.75 mmol) and stir the solution for 6 hours. Remove the solvent under reduced pressure and purify the residue with column chromatography (silica gel, 20-40% of EtOAc-Hexane) to give 0.45 g (35%) of the title compound as a colorless oil.

Preparation 32

3-(R)-(2-Chloro-6-fluoro-benzyl)-1-cyclohexyl-pyrrolidin-2-one

Dissolve (4R,5S)-(cis)-3-(2-(R)-chloro-6-fluoro-benzyl)-4-oxo-4-(2-oxo-4,5-diphenyl-oxazolidin-3-yl)-butyraldehyde (0.45 g, 0.97 mmol) in THF (50 mL). Add cyclohexylamine (0.19 g, 1.94 mmol), and acetic acid (0.12 g, 1.94 mmol) at room temperature under nitrogen. Stir the solution for one hour and then add sodium triacetoxyborohydride (0.82 g, 3.88 mmol). Stir the reaction mixture for over night and then add water (50 mL). Extract the aqueous layer with dichloromethane (3×100 mL). Combine the organic layers and dry with Na$_2$SO$_4$, filter, concentrate and purify by flash column chromatography (silica gel, 20-50% of EtOAc-Hexane) to give 0.26 g (88%) of the title compound as a colorless oil. Mass spectrum (ion spray): m/z=310.1, 312.2 (M+1).

EXAMPLE 1

1-(4,5,6,7-Tetrahydro-3H-benzoimidazol-5-yl)-3-(3,5,4'-trichloro-biphenyl-4-ylmethyl)-pyrrolidin-2-one

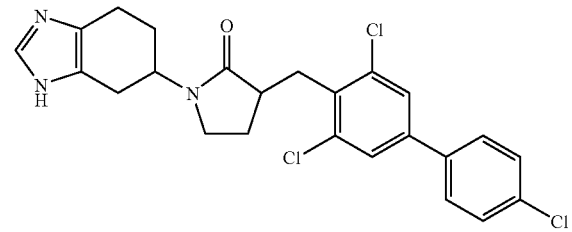

Dissolve trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-ylmethyl]-phenyl and trifluoro-methanesulfonic acid 3,5-dichloro-4-[2-oxo-1-(1-trifluoromethanesulfonyl-4,5,6,7-tetrahydro-3H-benzimidazol-5-yl)-pyrrolidin-3-ylmethyl]-phenyl esters (Preparation 14), 0.15 g, 0.23 mmol) in 2 ml of dioxane, and to this solution, add 4-chlorophenylboronic acid (45 mg, 0.28 mmol) and 0.5 mL of 2 M sodium carbonate. Purge the mixture with nitrogen for 1 min and add tetrakis(triphenylphosphene)palladium(0) (27 mg, 0.02 mmol). Cap the reaction and heat using microwave mediated heating for 45 min at 90° C. Apply the reaction to an SCX column and wash with Methanol (two column volumes). Then, wash with two column volumes of 2N NH$_3$ in Methanol to obtain semi-pure product. Purify further using HPLC or normal phase chromatography to yield 1-(4,5,6,7-Tetrahydro-3H-benzoimidazol-5-yl)-3-(3,5,4'-trichloro-biphenyl-4-ylmethyl)-pyrrolidin-2-one as a white solid (60.0 mg, 44%).

MS: m/z (M+1)=476.

TABLE 1

Prepare the Examples in Table 1 essentially as described in Example 1 except that 4-chlorophenylboronic acid is replaced by the reagent as indicated in column 3. Purification of the compounds using reverse phase HPLC chromatography results in trifluoroacetic acid salts of the compounds.

| Example | Structure and Chemical name | Reagent | Data m/z (M + 1) |
|---|---|---|---|
| 2 | 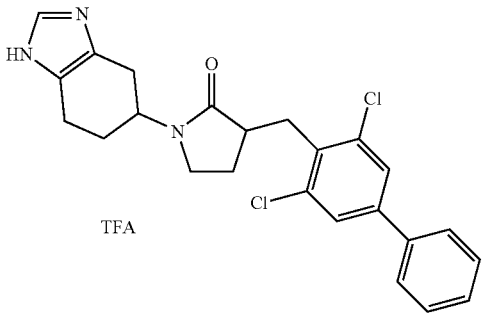<br>3-(3,5-Dichloro-biphenyl-4-ylmethyl)-1-(4,5,6,7-tetrahydro-1H-benzoimidazol-5-yl)-pyrrolidin-2-one | Phenyl boronic acid | 440 |
| 3 | 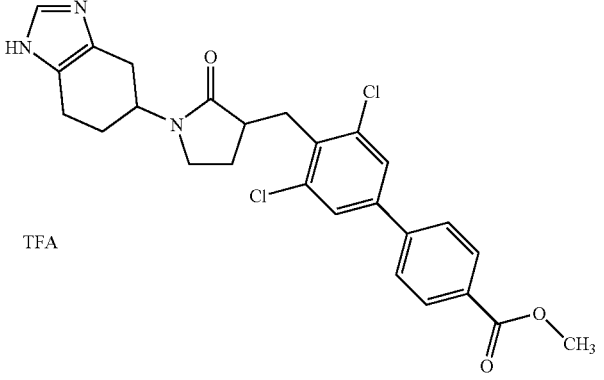<br>3',5'-Dichloro-4'-[2-oxo-1-(4,5,6,7-tetrahydro-1H-benzoimidazol-5-yl)-pyrrolidin-3-ylmethyl]-biphenyl-4-carboxylic acid methyl ester | 4-methoxy-carbonylboronic acid | 498 |
| 4 | 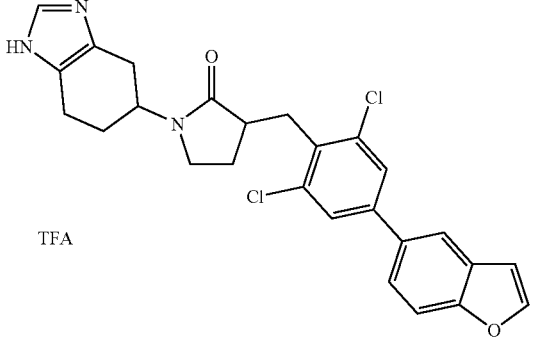<br>3-(4-Benzofuran-5-yl-2,6-dichloro-benzyl)-1-(4,5,6,7-tetrahydro-1H-benzoimidazol-5-yl)-pyrrolidin-2-one | Benzofuran-5-boronic acid | 480 |

TABLE 1-continued

*Prepare the Examples in Table 1 essentially as described in Example 1 except that 4-chlorophenylboronic acid is replaced by the reagent as indicated in column 3. Purification of the compounds using reverse phase HPLC chromatography results in trifluoroacetic acid salts of the compounds.*

| Example | Structure and Chemical name | Reagent | Data m/z (M + 1) |
|---|---|---|---|
| 5 | 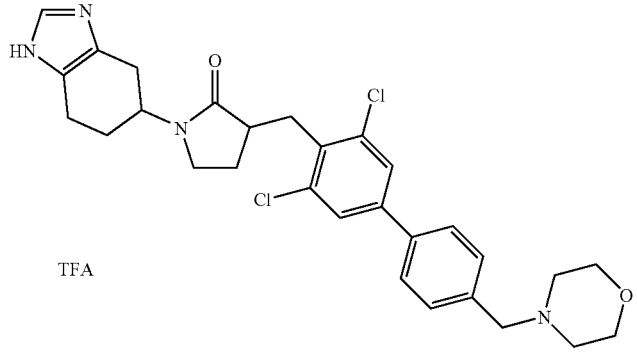<br>TFA<br>3-(3,5-Dichloro-4'-morpholin-4-ylmethyl-biphenyl-4-ylmethyl)-1-(4,5,6,7-tetrahydro-1H-benzoimidazol-5-yl)-pyrrolidin-2-one | 4-(morpholine-4-carbonyl)phenyl-boronic acid | 539 |
| 6 | 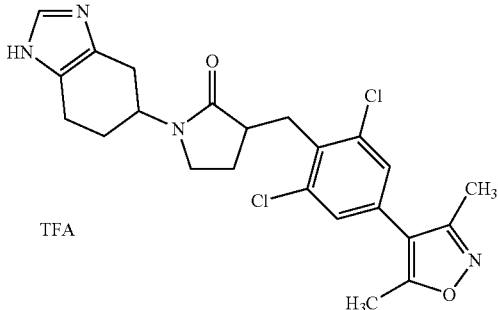<br>TFA<br>3-[2,6-Dichloro-4-(3,5-dimethyl-isoxazol-4-yl)-benzyl]-1-(4,5,6,7-tetrahydro-1H-benzoimidazol-5-yl)-pyrrolidin-2-one | 3,5-dimethyl-isoxazole-4-boronic acid | 459 |
| 7 | 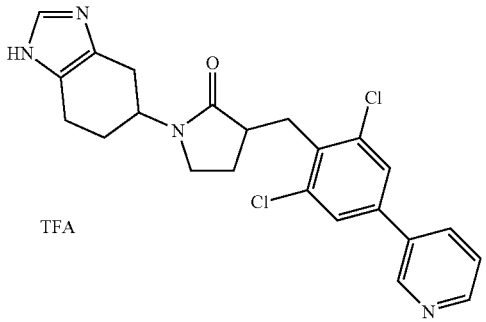<br>TFA<br>3-(2,6-Dichloro-4-pyridin-3-yl-benzyl)-1-(4,5,6,7-tetrahydro-1H-benzoimidazol-5-yl)-pyrrolidin-2-one | Pyridine-3-boronic acid | 441 |

TABLE 1-continued

Prepare the Examples in Table 1 essentially as described in Example 1 except that 4-chlorophenylboronic acid is replaced by the reagent as indicated in column 3. Purification of the compounds using reverse phase HPLC chromatography results in trifluoroacetic acid salts of the compounds.

| Example | Structure and Chemical name | Reagent | Data m/z (M + 1) |
| --- | --- | --- | --- |
| 8 | 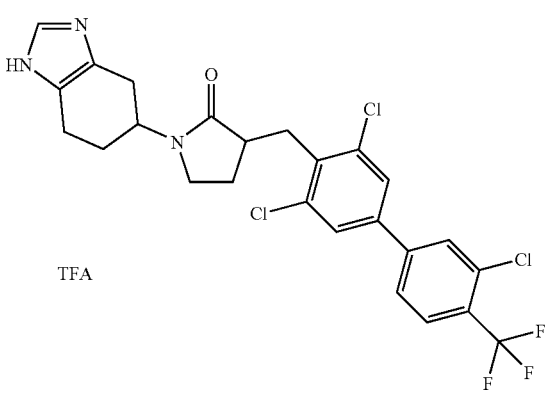<br>TFA<br>1-(4,5,6,7-Tetrahydro-1H-benzoimidazol-5-yl)-3-(3,5,3'-trichloro-4'-trifluoromethyl-biphenyl-4-ylmethyl)-pyrrolidin-2-one | 3-chloro-4-(trifluoromethyl)-phenylboronic acid | 542 |
| 9 | 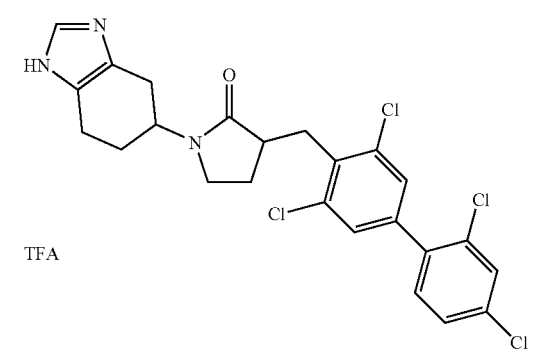<br>TFA<br>3-(3,5,2',4'-Tetrachloro-biphenyl-4-ylmethyl)-1-(4,5,6,7-tetrahydro-1H-benzoimidazol-5-yl)-pyrrolidin-2-one | 2,4-dichlorophenyl boronic acid | 508 |
| 10 | 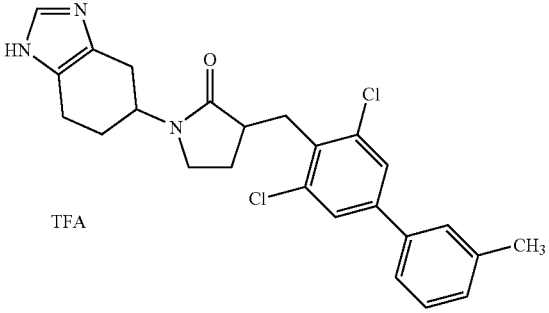<br>TFA<br>3-(3,5-Dichloro-3'-methyl-biphenyl-4-ylmethyl)-1-(4,5,6,7-tetrahydro-1H-benzoimidazol-5-yl)-pyrrolidin-2-one | 3-methylphenyl boronic acid | 454 |

TABLE 1-continued

*Prepare the Examples in Table 1 essentially as described in Example 1 except that 4-chlorophenylboronic acid is replaced by the reagent as indicated in column 3. Purification of the compounds using reverse phase HPLC chromatography results in trifluoroacetic acid salts of the compounds.*

| Example | Structure and Chemical name | Reagent | Data m/z (M + 1) |
|---|---|---|---|
| 11 | 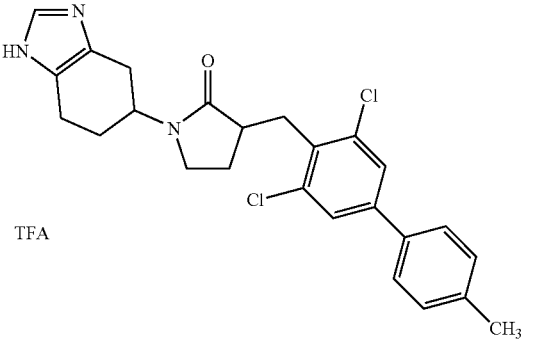<br>3-(3,5-Dichloro-4'-methyl-biphenyl-4-ylmethyl)-1-(4,5,6,7-tetrahydro-1H-benzoimidazol-5-yl)-pyrrolidin-2-one | 4-methylphenyl boronic acid | 454 |
| 12 | 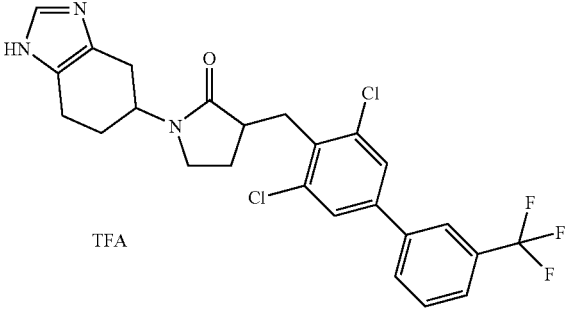<br>3-(3,5-Dichloro-3'-trifluoromethyl-biphenyl-4-ylmethyl)-1-(4,5,6,7-tetrahydro-1H-benzoimidazol-5-yl)-pyrrolidin-2-one | 3-(trifluoromethyl)phenyl boronic acid | 508 |
| 13 | 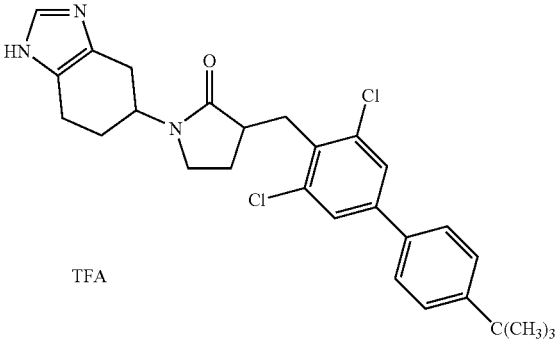<br>3-(4'-tert-Butyl-3,5-dichloro-biphenyl-4-ylmethyl)-1-(4,5,6,7-tetrahydro-1H-benzoimidazol-5-yl)-pyrrolidin-2-one | 4-tert-butylphenyl boronic acid | 496 |

TABLE 1-continued

Prepare the Examples in Table 1 essentially as described in Example 1 except that 4-chlorophenylboronic acid is replaced by the reagent as indicated in column 3. Purification of the compounds using reverse phase HPLC chromatography results in trifluoroacetic acid salts of the compounds.

| Example | Structure and Chemical name | Reagent | Data m/z (M + 1) |
|---|---|---|---|
| 14 | 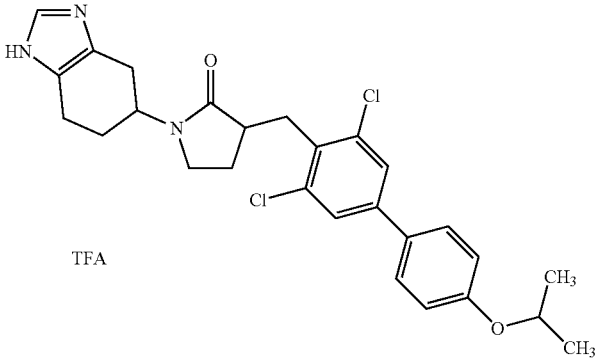 3-(3,5-Dichloro-4'-isopropoxy-biphenyl-4-ylmethyl)-1-(4,5,6,7-tetrahydro-1H-benzoimidazol-5-yl)-pyrrolidin-2-one | 4-isopropoxy-phenyl boronic acid | 498 |
| 15 | 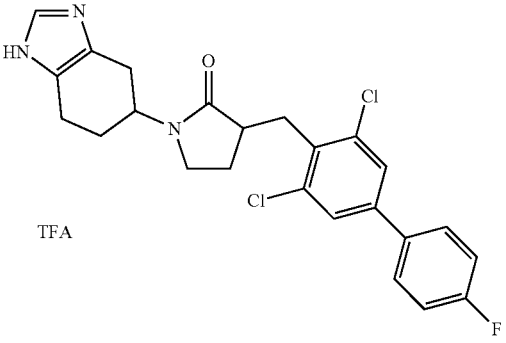 3-(3,5-Dichloro-4'-fluoro-bipheny-4-ylmethyl)-1-(4,5,6,7-tetrahydro-1H-benzoimidazol-5-yl)-pyrrolidin-2-one | 4-fluorophenyl-boronic acid | 458 |
| 16 | 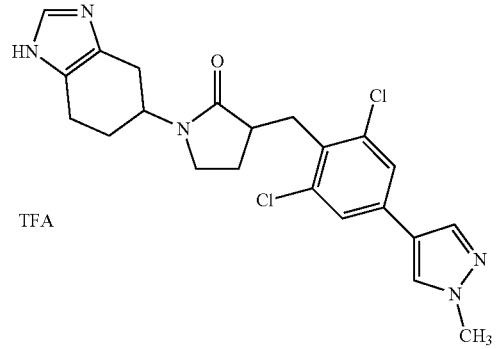 3-[2,6-Dichloro-4-(1-methyl-1H-pyrazol-4-yl)-benzyl]-1-(4,5,6,7-tetrahydro-1H-benzoimidazol-5-yl)-pyrrolidin-2-one | 1-methyl-4-(4,4,5,5-tetramethyl-1,3,2-dioxaborolan-2-yl)-1H-pyrazole | 445 |

TABLE 1-continued

Prepare the Examples in Table 1 essentially as described in Example 1 except that 4-chlorophenylboronic acid is replaced by the reagent as indicated in column 3. Purification of the compounds using reverse phase HPLC chromatography results in trifluoroacetic acid salts of the compounds.

| Example | Structure and Chemical name | Reagent | Data m/z (M + 1) |
|---|---|---|---|
| 17 | 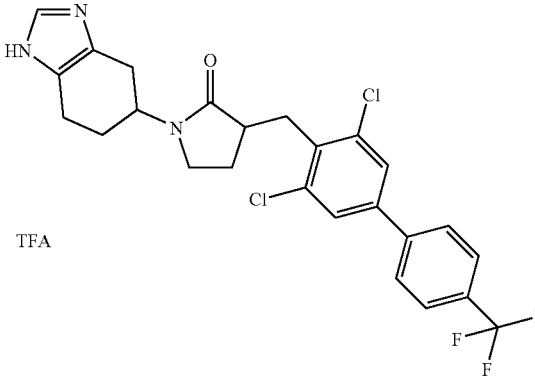<br>3-(3,5-Dichloro-4'-trifluoromethyl-biphenyl-4-ylmethyl)-1-(4,5,6,7-tetrahydro-1H-benzoimidazol-5-yl)-pyrrolidin-2-one | 4-(trifluoro-methyl)phenyl boronic acid | 508 |

EXAMPLE 18

3-[3,5-Dichloro-4'-(4-methyl-piperazine-1-carbonyl)-biphenyl-4-ylmethyl]-1-(4,5,6,7-tetrahydro-1H-benzoimidazol-5-yl)-pyrrolidin-2-one

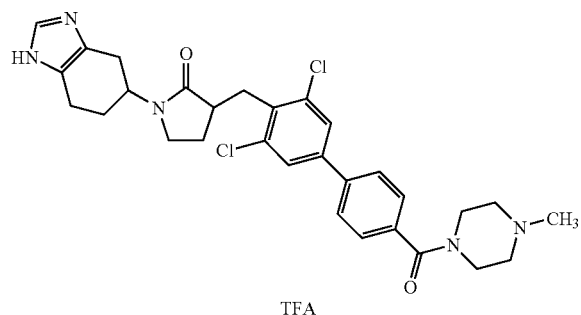

Dissolve the trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-ylmethyl]-phenyl and trifluoro-methanesulfonic acid 3,5-dichloro-4-[2-oxo-1-(1-trifluoromethanesulfonyl-4,5,6,7-tetrahydro-3H-benzimidazol-5-yl)-pyrrolidin-3-ylmethyl]-phenyl esters (Preparation 14), (0.15 g, 0.23 mmol) in 2 ml of dioxane (0.15 g, 0.23 mmol). To this solution, add 4-(4-Methyl-piperazin-1-yl)-phenyl-methanoneboronic acid (69 mg, 0.28 mmol) and 0.5 mL 2M sodium carbonate. Purge the mixture with nitrogen for 1 min and add tetrakis(triphenylphosphine)palladium(0) (27 mg, 0.02 mmol). Cap the reaction and heat using microwave mediated heating for 45 min at 90° C. Apply the reaction to an SCX column and wash with Methanol (two column volumes). Then wash with two column volumes of 2N $NH_3$ in Methanol to obtain semi-pure product. Purify further using HPLC or normal phase chromatography to yield 3-[3,5-Dichloro-4'-(4-methyl-piperazine-1-carbonyl)-biphenyl-4-ylmethyl]-1-(4,5,6,7-tetrahydro-1H-benzoimidazol-5-yl)-pyrrolidin-2-one (110 mg). MS: m/z (M+1)=566.

TABLE 2

Prepare the Examples in Table 2 essentially as described in Example 18 except that 4-(4-Methyl-piperazin-1-yl)-phenyl-methanoneboronic acid is replaced by the reagent as indicated in column 3. Purification of the compounds using reverse phase HPLC chromatography results in trifluoroacetic acid salts of the compounds.

| Example | Structure and Chemical name | Reagent | Data m/z (M + 1) |
|---|---|---|---|
| 19 | 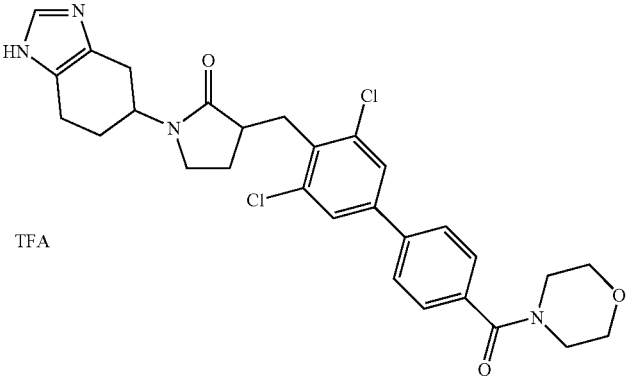<br>3-[3,5-Dichloro-4'-(morpholine-4-carbonyl)-biphenyl-4-ylmethyl]-1-(4,5,6,7-tetrahydro-1H-benzoimidazol-5-yl)-pyrrolidin-2-one | 4-(morpholine-4-carbonyl)phenyl-boronic acid | 553 |
| 20 | 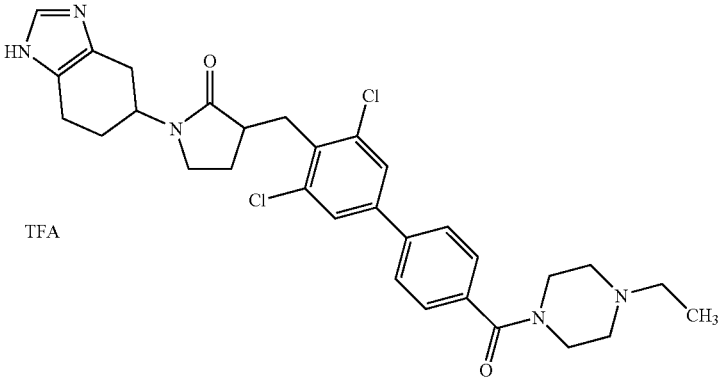<br>3-[3,5-Dichloro-4'-(4-ethyl-piperazine-1-carbonyl)-biphenyl-4-ylmethyl]-1-(4,5,6,7-tetrahydro-1H-benzoimidazol-5-yl)-pyrrolidin-2-one | 4-(4-ethyl-piperazine-1-carbonyl)-phenylboronic acid | 580 |
| 21 | 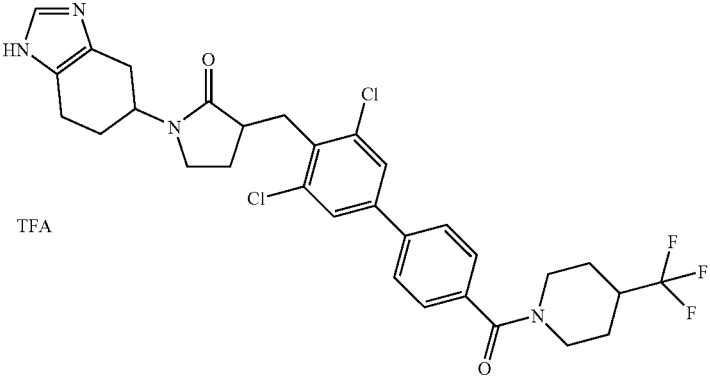<br>3-[3,5-Dichloro-4'-(4-trifluoromethyl-piperidine-1-carbonyl)-biphenyl-4-ylmethyl]-1-(4,5,6,7-tetrahydro-1H-benzoimidazol-5-yl)-pyrrolidin-2-one | 4-(4-trifluoromethyl)piperidine-1-carbonyl)phenyl-boronic acid | 619 |

EXAMPLES 22 AND 23

3-[R]-[4-(4-fluorophenyl-2,6-dichloro-benzyl)-1-(4,5,6,7-tetrahydro-3H-benzimidazole-3-yl)-pyrrolidin-2-one

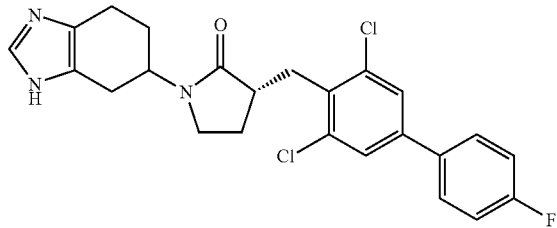

Heat a mixture of trifluoro-methanesulfonic acid 3,5-dichloro-4-[2-oxo-1-(3-trifluoromethanesulfonyl-4,5,6,7-tetrahydro-3H-benzimidazol-5-yl)-pyrrolidin-3-ylmethyl]-phenyl and trifluoro-methanesulfonic acid 3,5-dichloro-4-[2-oxo-1-(1-trifluoromethanesulfonyl-4,5,6,7-tetrahydro-3H-benzimidazol-5-yl)-pyrrolidin-3-ylmethyl]-phenyl esters (850 mg) (Preparation 20), 4-fluorophenylboronic acid (221 mg), tetrakis-triphenylphosphine palladium (16 mg), and saturated sodium bicarbonate (1 mL) in 10 mL of DME at 90° C. in a vial. Filter the reaction through a SCX column (10 gm, Varion) with ethyl acetate (10 mL). Elute the product with 1 M ammonia in methanol and concentrate to dryness on rotary evaporator to give product as crude (400 mg). Purify this material by chiral purification on a Chiralpak AD-H (4.6×150 mm) column eluting with 60:40:0.2 3A ethanol/heptane/DMEA (Flow=0.6 mL/min.) to give:

Example 22 (Isomer 1, MS: m/z (M+1)=458, Rt. 5.8 min, ee>99%, 187 mg).

Example 23 (isomer 2, MS: m/z (M+1)=458, Rt. 9.7 min, ee>99%, 164 mg).

EXAMPLES 24 AND 25

(R)-3-[3,5-Dichloro-4'-(morpholine-4-carbonyl)-biphenyl-4-ylmethyl]-1-(4,5,6,7-tetrahydro-1H-benzoimidazol-5-yl)-pyrrolidin-2-one hydrochloride salt

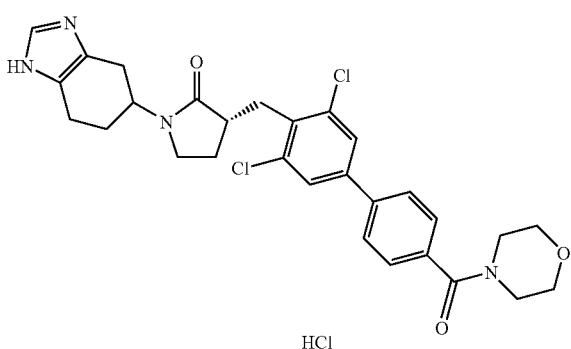

Examples 24 and 25 may be prepared essentially as described in the procedure for Examples 22 and 23 except that 4-fluorophenylboronic acid is replaced by 4-(morpholine-4-carbonyl)phenylboronic acid. Chiral purification gives:

Example 24 (Isomer 1, MS: m/z (M+1)=553, Rt. 7.3 min.
Example 25 (Isomer 2, MS: m/z (M+1)=553, Rt. 16.6 min.

EXAMPLE 26

1-(4,5,6,7-Tetrahydro-3H-benzoimidazol-5-yl)-3-[R]-[2,6-dichloro-4(4-N,N-dimethylsulfonylphenyl)-phenyl-pyrrolidin-2-one

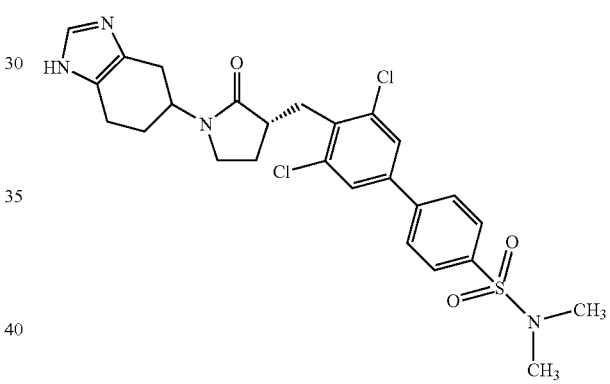

Dissolve Preparation 26 (0.15 g, 0.23 mmol) in 2 ml dioxane. To this solution, add 4-N,N-dimethylsulfonylphenylboronic acid (45 mg, 0.28 mmol) and 0.5 mL 2M sodium carbonate. Purge the mixture with nitrogen for 1 min and add tetrakis (triphenylphosphine) palladium (0) (27 mg, 0.02 mmol). Cap the reaction and heat using microwave mediated heating for 45 min at 90° C. Apply the reaction to an SCX column and wash with Methanol (two column volumes). Then wash with two column volumes of 2N $NH_3$ in Methanol to obtain semi-pure product. Purify further using HPLC or normal phase chromatography to yield 1-(4,5,6,7-tetrahydro-3H-benzoimidazol-5-yl)-3-[R]-[2,6-dichloro-4(4-N,N-dimethylsulfonylphenyl)-phenyl-pyrrolidin-2-one as a white solid (mg, 44%). MS: m/z=547 (M+1).

TABLE 3

Prepare the Examples in Table 3 essentially as described in Example 26 except that 4-N,N-dimethylsulfonylphenylboronic acid is replaced by the reagent as indicated in column 3.

| Example | Structure and Chemical name | Reagent | Data m/z (M + H) |
|---|---|---|---|
| 27 | 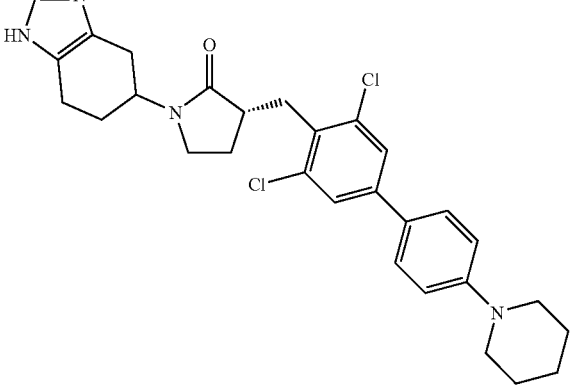<br>TFA<br>(R)-3-(3,5-Dichloro-4′-piperidin-1-yl-biphenyl-4-ylmethyl)-1-(4,5,6,7-tetrahydro-1H-benzoimidazol-5-yl)-pyrrolidin-2-one | 4-(1-piperidinyl)-phenylboronic acid HCl | 523 |
| 28 | 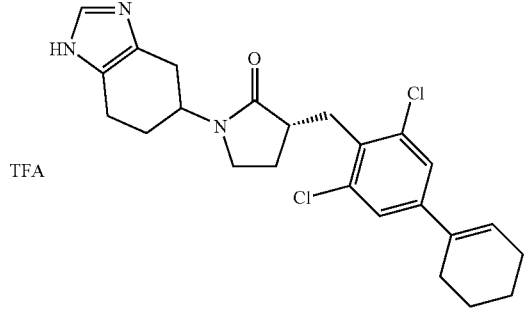<br>TFA<br>(R)-3-(2,6-Dichloro-4-cyclohex-1-enyl-benzyl)-1-(4,5,6,7-tetrahydro-1H-benzoimidazol-5-yl)-pyrrolidin-2-one | Cyclohexen-1-yl-boronic acid | 444 |
| 29 | 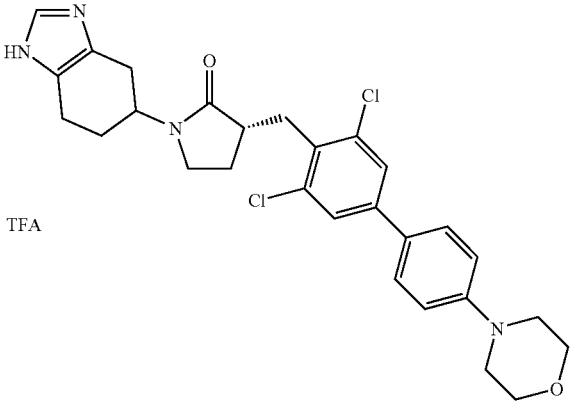<br>TFA<br>(R)-3-(3,5-Dichloro-4′-morpholin-4-yl-biphenyl-4-ylmethyl)-1-(4,5,6,7-tetrahydro-1H-benzoimidazol-5-yl)-pyrrolidin-2-one | 4-morpholinophenyl-boronic acid | 525 |

TABLE 3-continued

*Prepare the Examples in Table 3 essentially as described in Example 26 except that 4-N,N-dimethylsulfonylphenylboronic acid is replaced by the reagent as indicated in column 3.*

| Example | Structure and Chemical name | Reagent | Data m/z (M + H) |
|---|---|---|---|
| 30 | 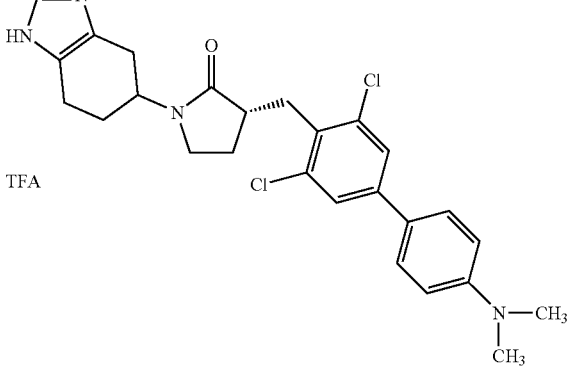<br>(R)-3-(3,5-Dichloro-4'-dimethylamino-biphenyl-4-ylmethyl)-1-(4,5,6,7-tetrahydro-1H-benzoimidazol-5-yl)-pyrrolidin-2-one | 4-(N,N-dimethylamino)phenyl-boronic acid | 483 |
| 31 | 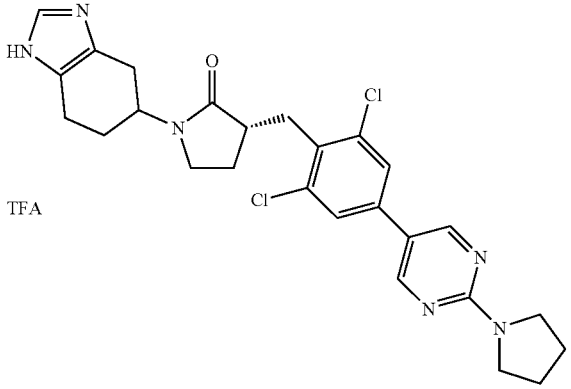<br>(R)-3-[2,6-Dichloro-4-(2-pyrrolidin-1-yl-pyrimidin-5-yl)-benzyl]-1-(4,5,6,7-tetrahydro-1H-benzoimidazol-5-yl)-pyrrolidin-2-one | 2-pyrrolidin-1-yl-1-pyrimidine-5-phenylboronic acid | 511 |
| 32 | 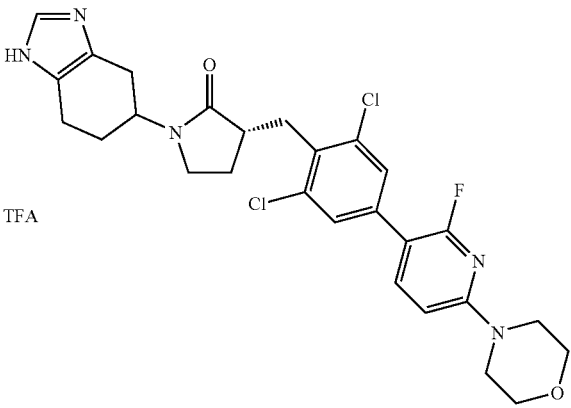<br>(R)-3-[2,6-Dichloro-4-(2-fluoro-6-morpholin-4-yl-pyridin-3-yl)-benzyl]-1-(4,5,6,7-tetrahydro-1H-benzoimidazol-5-yl)-pyrrolidin-2-one | 2-fluoro-6-morpholin-4-yl-pyridine-3-phenylboronic acid | 544 |

… TABLE 3-continued

*Prepare the Examples in Table 3 essentially as described in Example 26 except that 4-N,N-dimethylsulfonylphenylboronic acid is replaced by the reagent as indicated in column 3.*

| Example | Structure and Chemical name | Reagent | Data m/z (M + H) |
|---|---|---|---|
| 33 | 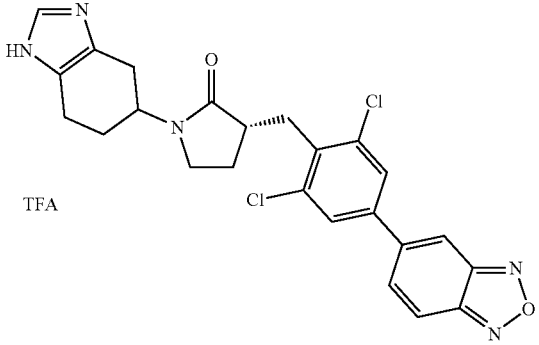<br>(R)-3-(4-Benzo[1,2,5]oxadiazol-5-yl-2,6-dichloro-benzyl)-1-(4,5,6,7-tetrahydro-1H-benzoimidazol-5-yl)-pyrrolidin-2-one | Benzo[1,2,5]oxadiazole-5-phenylboronic acid | 482 |
| 34 | 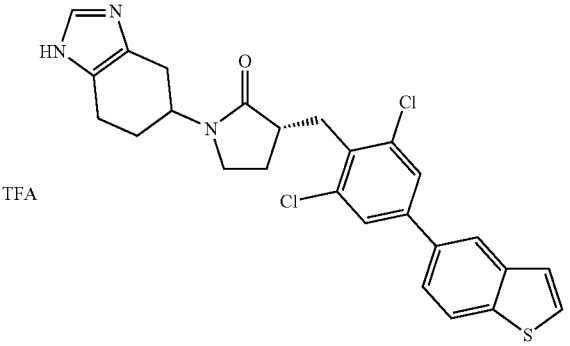<br>(R)-3-(4-Benzo[b]thiophen-5-yl-2,6-dichloro-benzyl)-1-(4,5,6,7-tetrahydro-1H-benzoimidazol-5-yl)-pyrrolidin-2-one | 2-(1-benzothiophen-5-yl)-4,4,5,5-tetramethyl-1,3,2-dioxaborolane | 496 |
| 35 | 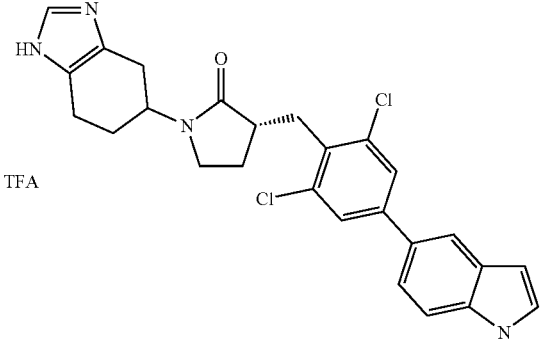<br>(R)-3-[2,6-Dichloro-4-(1H-indol-5-yl)-benzyl]-1-(4,5,6,7-tetrahydro-1H-benzoimidazol-5-yl)-pyrrolidin-2-one | 5-indolylboronic acid | 479 |

TABLE 3-continued

Prepare the Examples in Table 3 essentially as described in Example 26 except that 4-N,N-dimethylsulfonylphenylboronic acid is replaced by the reagent as indicated in column 3.

| Example | Structure and Chemical name | Reagent | Data m/z (M + H) |
|---|---|---|---|
| 36 | 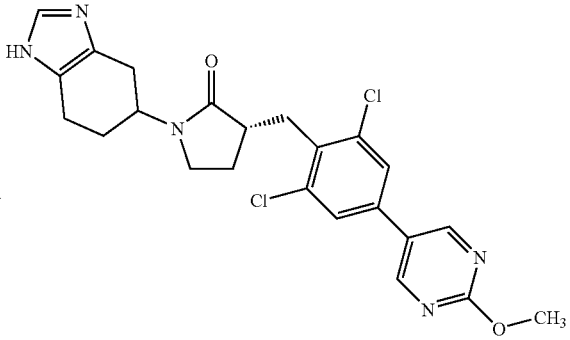<br>TFA<br>(R)-3-[2,6-Dichloro-4-(2-methoxy-pyrimidin-5-yl)-benzyl]-1-(4,5,6,7-tetrahydro-1H-benzoimidazol-5-yl)-pyrrolidin-2-one | 2-methoxy-pyrimidine-5-boronic acid | 472 |
| 37 | 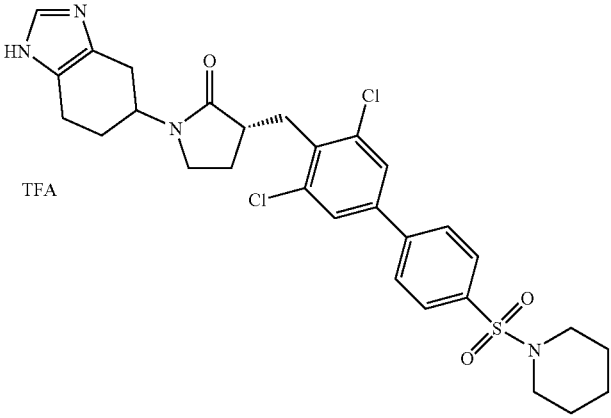<br>TFA<br>(R)-3-[3,5-Dichloro-4'-(piperidine-1-sulfonyl)-biphenyl-4-ylmethyl]-1-(4,5,6,7-tetrahydro-1H-benzoimidazol-5-yl)-pyrrolidin-2-one | 4-(piperidine-1-sulfonyl)-phenylboronic acid | 587 |
| 38 | 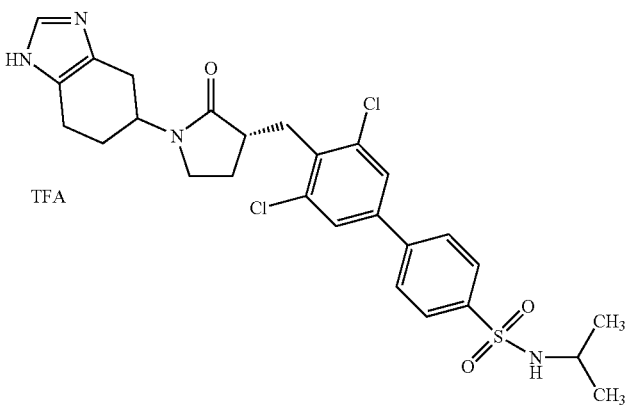<br>TFA<br>3',5'-Dichloro-4'-[(R)-2-oxo-1-(4,5,6,7-tetrahydro-1H-benzoimidazol-5-yl)-pyrrolidin-3-ylmethyl]-biphenyl-4-sulfonic acid isopropylamide | 4-isopropyl-sulfamoylphenyl-boronic acid | 561 |

TABLE 3-continued

Prepare the Examples in Table 3 essentially as described in Example 26 except that 4-N,N-dimethylsulfonylphenylboronic acid is replaced by the reagent as indicated in column 3.

| Example | Structure and Chemical name | Reagent | Data m/z (M + H) |
|---|---|---|---|
| 39 | 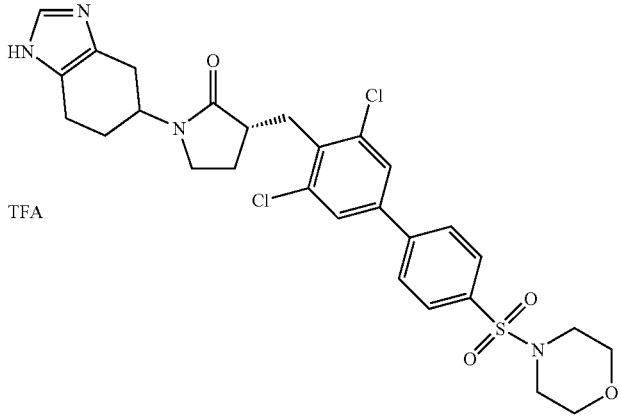 TFA<br>(R)-3-[3,5-Dichloro-4'-(morpholine-4-sulfonyl)-biphenyl-4-ylmethyl]-1-(4,5,6,7-tetrahydro-1H-benzoimidazol-5-yl)-pyrrolidin-2-one | 4-(morpholine-1-sulfonyl)-phenylboronic acid | 589 |
| 40 | 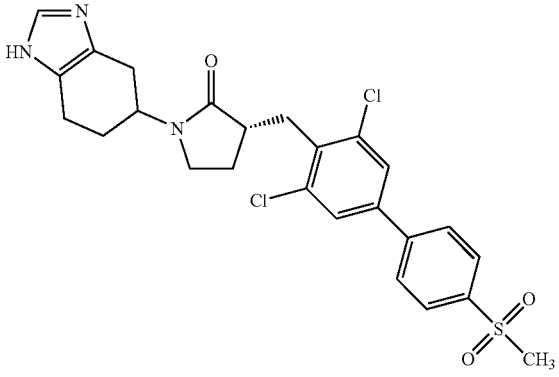<br>(R)-3-[3,5-Dichloro-4'-(methylsulfonyl)-biphenyl-4-ylmethyl]-1-(4,5,6,7-tetrahydro-1H-benzoimidazol-5-yl)-pyrrolidin-2-one | 4-(methyl-sulfonyl)-phenylboronic acid | 518 |
| 41 | 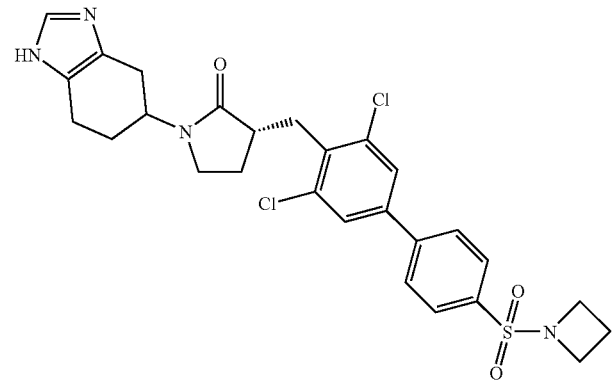<br>(R)-3-[3,5-Dichloro-4'-(azitidine-4-sulfonyl)-biphenyl-4-ylmethyl]-1-(4,5,6,7-tetrahydro-1H-benzoimidazol-5-yl)-pyrrolidin-2-one | 4-(azitidinee-1-sulfonyl)-phenylboronic acid | 563 |

EXAMPLE 42

3-[R]-[3,5-Dichloro-4'-(4-trifluoromethyl-piperidine-1-carbonyl)-biphenyl-4-ylmethyl]-1-(4,5,6,7-tetrahydro-3H-benzoimidazol-5-yl)-pyrrolidin-2-one

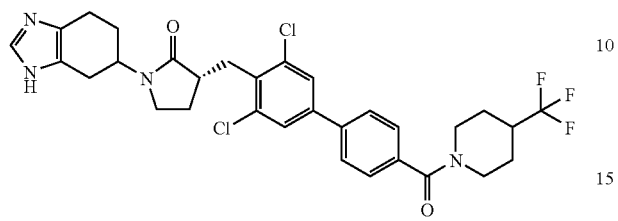

Dissolve Preparation 26 (0.10 g, 0.16 mmol) in 2 ml of dioxane. To this solution, add (4-chlorocarbonylphenyl)boronic anhydride (52 mg, 0.31 mmol), 4-trifluoromethylpiperidine hydrochloride (76 mg, 0.40 mmol) and 0.5 mL 2M sodium carbonate. Purge the mixture with nitrogen for 1 min and add tetrakis(triphenylphosphene) palladium (0) (23 mg, 0.02 mmol). Cap the reaction and heat using microwave mediated heating for 30 min at 110° C. Apply the reaction to an SCX column and wash with Methanol (two column volumes). Then wash with two column volumes of 2N $NH_3$ in Methanol to obtain semi-pure product. Purify further using HPLC or normal phase chromatography to yield 3-(3,5-Dichloro-4'-morpholin-4-yl-biphenyl-4-ylmethyl)-1-(4,5,6,7-tetrahydro-1H-benzoimidazol-5-yl)-pyrrolidin-2-one (43 mg).

MS: m/z=625 (M+1).

EXAMPLE 43

(R)-3-[3,5-Dichloro-4'-(4,4-difluoro-piperidine-1-carbonyl)-biphenyl-4-ylmethyl]-1-(4,5,6,7-tetrahydro-1H-b enzoimidazol-5-yl)-pyrrolidin-2-one

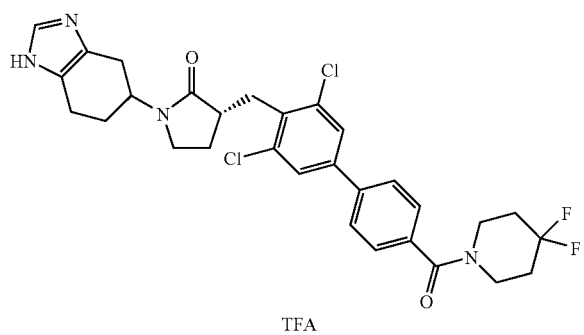

TFA

Example 43 may be prepared essentially as described in Example 42 except that 4-trifluoromethylpiperidine hydrochloride is replaced by 4,4-difluoro-piperidine.

MS: m/z (M+1)=587.

EXAMPLE 44

3-(4-Bromo-2-chlorobenzyl)-1-(4,5,6,7-tetrahydro-3H-benzo[d]imidazol-5-yl)pyrrolidin-2-one, TFA salt

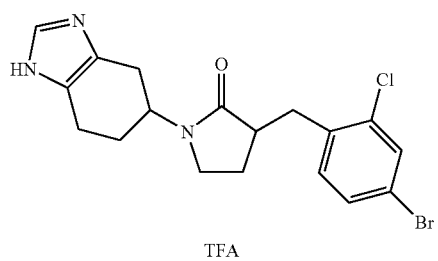

TFA

Using the procedure to synthesize Preparation 32 and using reagent ethyl 2-(4-bromo-2-chlorobenzyl)-4-oxobutanoate (0.95 g, 2.85 mmol) and 4,5,6,7-tetrahydro-3H-benzo[d]imidazol-5-amine (0.49 g, 2.85 mmol) yields 0.52 g (45%) of the title compound as a white solid. MS (APCI-pos mode) m/z (rel intensity) 408.1 (80), 410.1 (100).

In the following section enzyme and functional assays are described which are useful for evaluating the compounds of the invention.

11β-HSD Type 1 Enzyme Assay

Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 µL/well capacity) in the following fashion: 9 µL/well of substrate (2.22 mM NADP, 55.5 µM Cortisol, 10 mM Tris, 0.25% Prionex, 0.1% Triton X100), 3 µL/well of water to compound wells or 3 µL to control and standard wells, 6 µL/well recombinant human 11β-HSD type 1 enzyme, 2 µL/well of compound dilutions. For ultimate calculation of percent inhibition, a series of wells are added that represent assay minimum and maximum: one set containing substrate with 667 µM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes each plate individually from the stacker and places them in position for addition of 5 µL/well of a 250 µM carbenoxolone solution to stop the enzymatic reaction. Plates are then shaken once more for 15 seconds then placed into an Ultra 384 microplate reader (355EX/460EM) for detection of NADPH fluorescence.

Data for example compounds in the 11-βHSD1 assay are shown below:

| Example | Structure | Human 11-βHSD1 IC$_{50}$ (nM) |
|---|---|---|
| 1 | 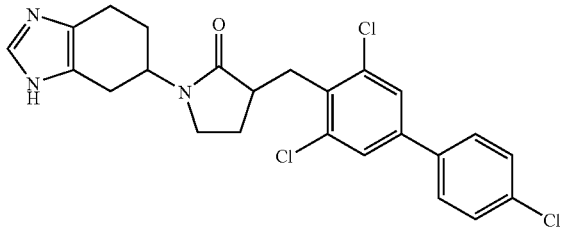 | 325 |
| 15 | 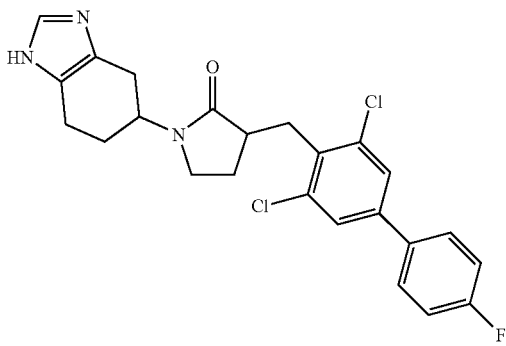 | 214 |
| 29 | 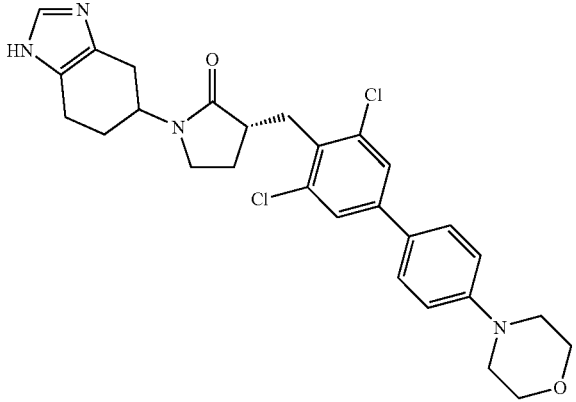 | 75.4 |
| 32 | 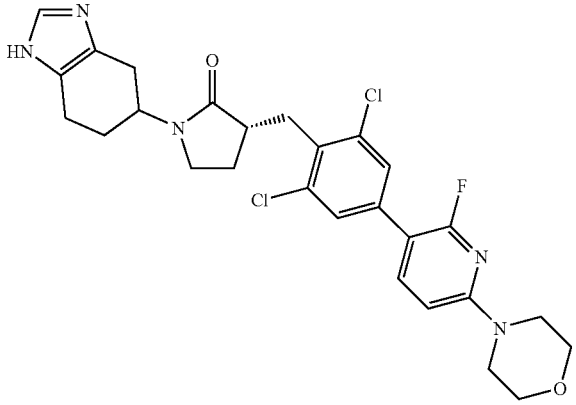 | 175 |

-continued

| Example | Structure | Human 11-βHSD1 IC$_{50}$ (nM) |
|---|---|---|
| 42 | 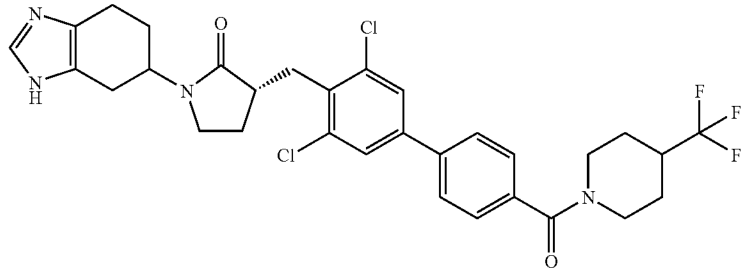 | 143 |

Compounds of the invention can also tested for selectivity against 11-βHSD2 in an assay similar to that described for 11-βHSD1, but using the 11-βHSD2 enzyme. The assay using the 11-βHSD2 enzyme can be carried out by the methods described herein and supplemented by methods known in the art.

Human Aortic Smooth Muscle Cell Assay

Primary human aortic smooth muscle cells (AoSMC) are cultured in 5% FBS growth medium to a passage number of 6, then pelleted by centrifugation and resuspended at a density of $9 \times 10^4$ cells/mL in 0.5% FBS assay medium containing 12 ng/mL hTNFα to induce expression of 11β-HSD1. Cells are seeded into 96-well tissue culture assay plates at 100 μL/well ($9 \times 10^3$ cells/well) and incubated for 48 hours at 37° C., 5% $CO_2$. Following induction, cells are incubated for 4 hours at 37° C., 5% $CO_2$ in assay medium containing test compounds then treated with 10 μL/well of 10 μM cortisone solubilized in assay medium, and incubated for 16 hours at 37° C., 5% $CO_2$. Medium from each well is transferred to a plate for subsequent analysis of cortisol using a competitive fluorescence resonance time resolved immunoassay. In solution, an allophycocyanin (APC)-cortisol conjugate and free cortisol analyte compete for binding to a mouse anti-cortisol antibody/Europium (Eu)-anti mouse IgG complex. Higher levels of free cortisol result in diminishing energy transfer from the Europium-IgG to the APC-cortisol complex resulting in less APC fluorescence. Fluorescent intensities for Europium and APC are measured using a LJL Analyst AD. Europium and APC excitation is measured using 360 nm excitation and 615 nm and 650 nm emission filters respectively. Time resolved parameters for Europuium were 1000 μs integration time with a 200 μs delay. APC parameters are set at 150 μs integration time with a 50 μs delay. Fluorescent intensities measured for APC are modified by dividing by the Eu fluorescence (APC/Eu). This ratio is then used to determine the unknown cortisol concentration by interpolation using a cortisol standard curve fitted with a 4-parameter logistic equation. These concentrations are then used to determine compound activity by plotting concentration versus % inhibition, fitting with a 4-parameter curve and reporting the IC$_{50}$.

All of the examples disclosed herein demonstrate activity in the human aortic smooth muscle cell assay with IC$_{50}$ of less than 300 nM. Data for example compounds in the human aortic smooth muscle cell assay are shown below:

| Example | Structure | IC$_{50}$ (nM) |
|---|---|---|
| 1 | 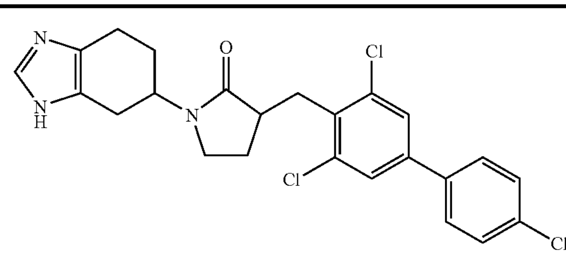 | 6.8 |

-continued
| Example | Structure | IC$_{50}$ (nM) |
|---|---|---|
| 15 | 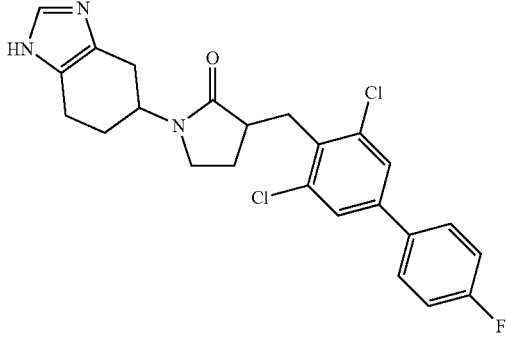 | 3.2 |
| 29 | 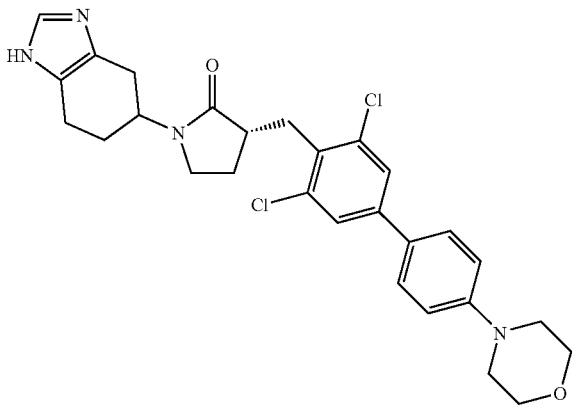 | 0.60 |
| 32 | 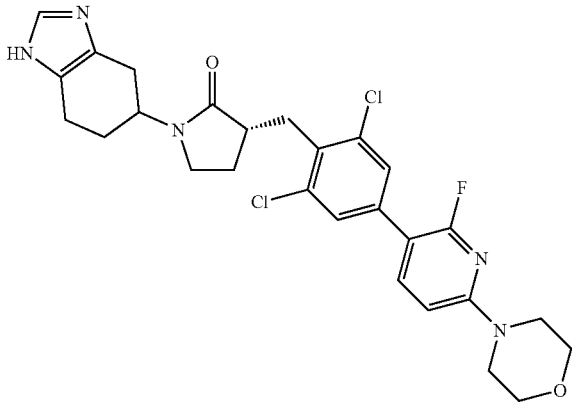 | 3.0 |
| 42 | 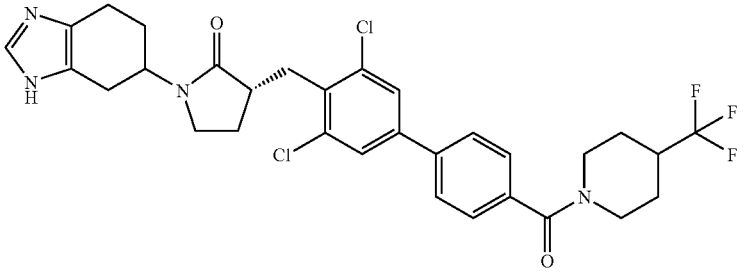 | 4.5 |

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male C57BL/6 mice are obtained from Harlan Sprague Dawley at average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 µl per animal, followed by a subcutaneous dose, 200 µl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum transferred to wells of 96-well plates (Corning Inc, Costar #4410, cluster tubes, 1.2 ml, polypropylene), and the plates are frozen at −20° C. until analysis by LC-MS/MS. For analysis, serum samples are thawed and the proteins are precipitated by the addition of acetonitrile containing d-4-cortisol internal standard. Samples are vortex mixed and centrifuged. The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer.

Data for example compounds in the acute in vivo cortisone conversion assay are shown below:

| Example | Structure | % Inhibition after 16 hours (dose of 10 (mg/kg)) |
|---|---|---|
| 29 | 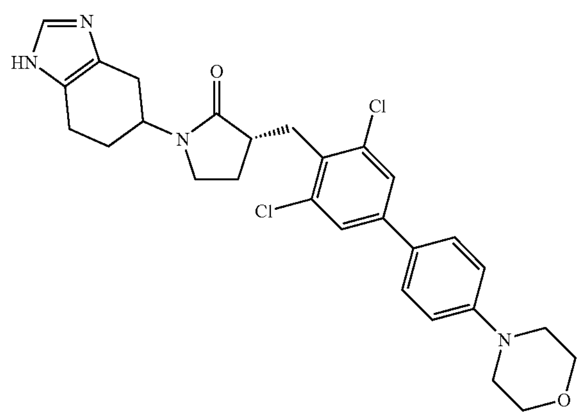 | 52 |
| 32 | 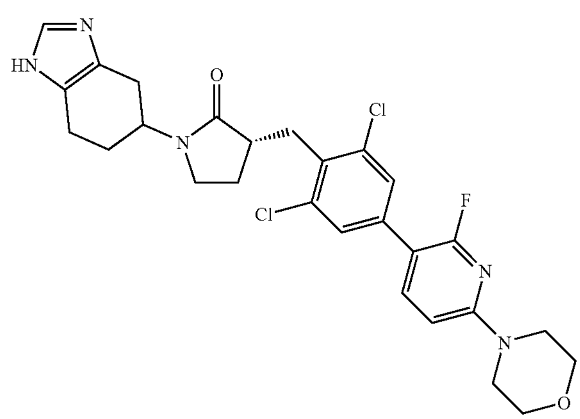 | 59.2 |

| Example | Structure | % Inhibition after 16 hours (dose of 10 (mg/kg)) |
|---|---|---|
| 42 | 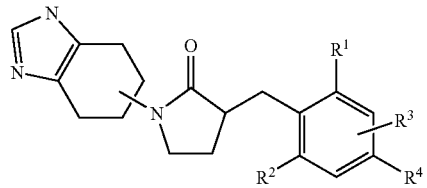 | 98.4 |

Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19th ed., Mack Publishing Co., 1995).

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from those described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intravenous, transdermal, intranasal, rectal, ocular, topical, sublingual, buccal, or other routes. Oral administration may be preferred for treatment of the disorders described herein. In those instances where oral administration is impossible or not preferred, the composition may be made available in a form suitable for parenteral administration, e.g., intravenous, intraperitoneal or intramuscular.

We claim:

1. A compound structurally represented by the formula:

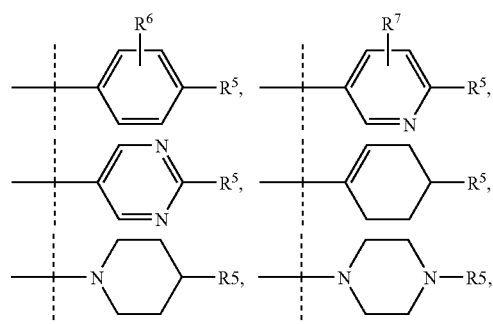

wherein:

$R^1$ is —H, -halogen, —O—$CH_3$ (optionally substituted with one to three halogens), or —$CH_3$ (optionally substituted with one to three halogens);

$R^2$ is —H, -halogen, —O—$CH_3$ (optionally substituted with one to three halogens), or —$CH_3$ (optionally substituted with one to three halogens);

$R^3$ is —H or -halogen;

$R^4$ is
—OH, -halogen, cyano, —($C_1$-$C_4$)alkyl(optionally substituted with one to three halogens), —($C_1$-$C_6$)alkoxy (optionally substituted with one to three halogens), —$SCF_3$, —C(O)O($C_1$-$C_4$)alkyl, —($C_3$-$C_8$)cycloalkyl, —O-phenyl-C(O)O—($C_1$-$C_4$)alkyl, —$CH_2$-phenyl, —$NHSO_2$—($C_1$-$C_4$)alkyl, —$NHSO_2$-phenyl($R^{21}$)($R^{21}$), —($C_1$-$C_4$)alkyl-C(O)N($R^{10}$)($R^{11}$), -continued

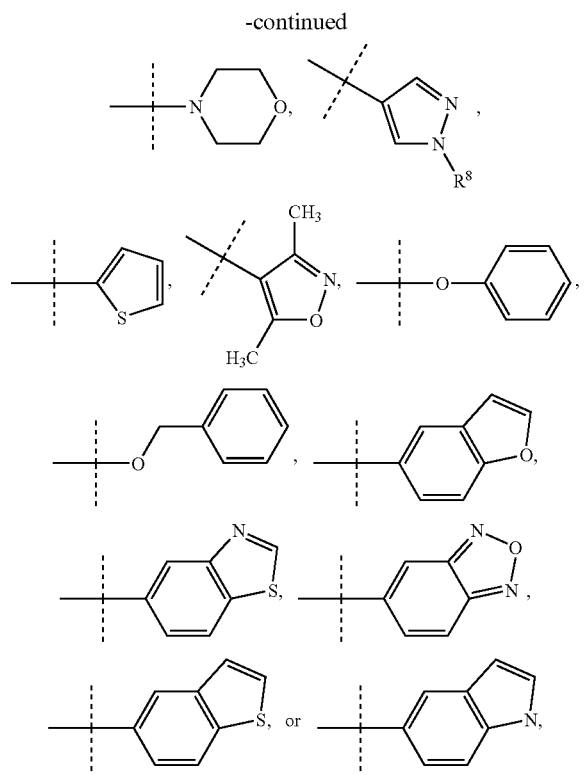

wherein the dashed line represents the point of attachment to the $R^4$ position;

$R^5$ is
- —H, -halogen, —($C_1$-$C_4$)alkyl(optionally substituted with 1 to 3 halogens),
- —C(O)OH, —C(O)O—($C_1$-$C_4$)alkyl, —C(O)—($C_1$-$C_4$)alkyl, —O—($C_1$-$C_4$)alkyl(optionally substituted with 1 to 3 halogens), —$SO_2$—($C_1$-$C_4$)alkyl, —N($R^8$)($R^8$),

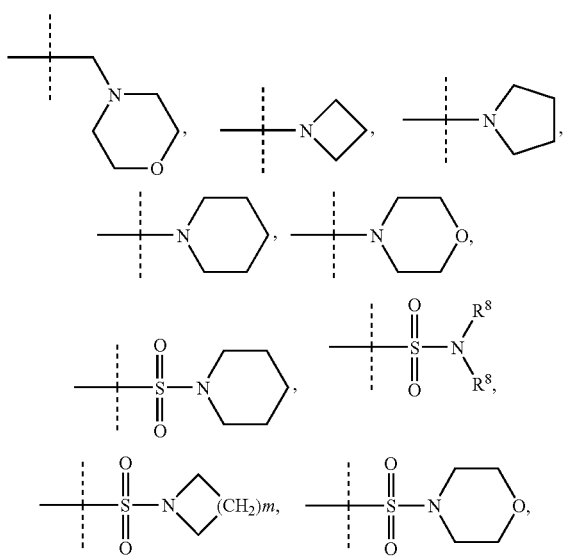

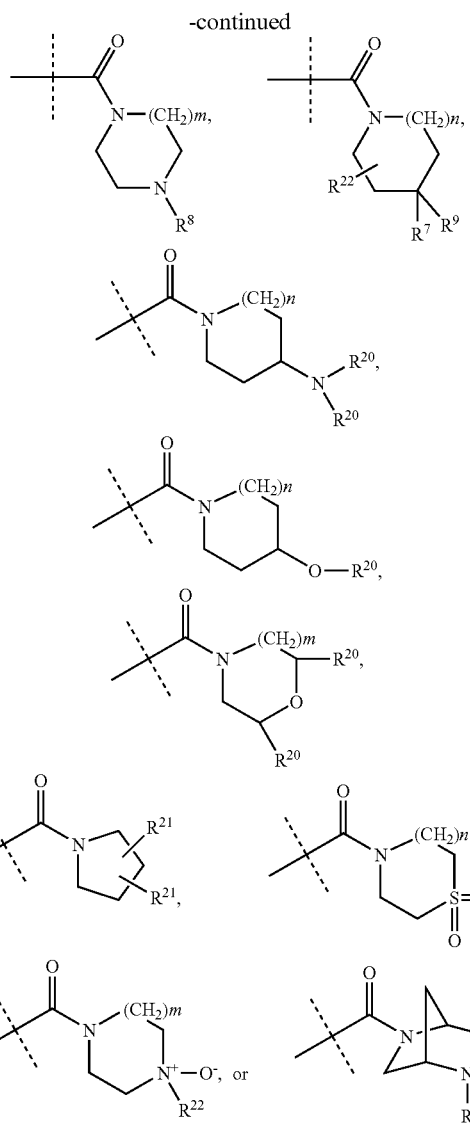

wherein the dashed line represents the point of attachment to the position indicated by $R^5$;
wherein m is 1, 2, or 3;
wherein n is 0, 1, or 2, and wherein when n is 0, then "$(CH_2)n$" is a bond;

$R^6$ is
- —H, -halogen, —CN, or —($C_1$-$C_4$)alkyl(optionally substituted with 1 to 3 halogens);

$R^7$ is
- —H, -halogen, or —($C_1$-$C_4$)alkyl(optionally substituted with 1 to 3 halogens);

$R^8$ is independently at each occurrence
- —H, —($C_1$-$C_6$)alkyl(optionally substituted with 1 to 3 halogens),
- —C(O)($C_1$-$C_6$)alkyl(optionally substituted with 1 to 3 halogens),
- —C(O)—($C_3$-$C_8$)cycloalkyl, —S($O_2$)—($C_3$-$C_8$)cycloalkyl or
- —S($O_2$)—($C_1$-$C_3$)alkyl(optionally substituted with 1 to 3 halogens);

$R^9$ is —H or -halogen;
$R^{10}$ and $R^{11}$ are each independently

—H or —(C$_1$-C$_4$)alkyl, or R$^{10}$ and R$^{11}$ taken together with the nitrogen to which they are attached form piperidinyl, piperazinyl, or pyrrolidinyl;

R$^{20}$ is independently at each occurrence —H, or —(C$_1$-C$_3$) alkyl(optionally substituted with 1 to 3 halogens);

R$^{21}$ is independently at each occurrence —H, -halogen, or —(C$_1$-C$_3$)alkyl(optionally substituted with 1 to 3 halogens);

R$^{22}$ is independently at each occurrence —H or —(C$_1$-C$_6$) alkyl(optionally substituted with 1 to 3 halogens); and R$^{23}$ is independently at each occurrence —H, —(C$_1$-C$_4$) alkyl, or —C(O)O—(C$_1$-C$_4$)alkyl;

or a pharmaceutically acceptable salt thereof.

2. A compound of claim 1 structurally represented by the formula:

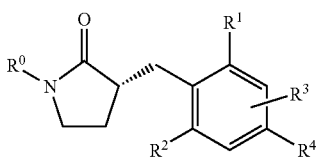

wherein:

R$^0$ is

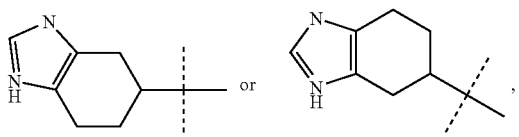

or a pharmaceutically acceptable salt thereof.

3. A compound of claim 2 wherein R$^1$ and R$^2$ are chlorine, or a pharmaceutically acceptable salt thereof.

4. A compound of claim 3 wherein R$^3$ is hydrogen, or a pharmaceutically acceptable salt thereof.

5. A compound of claim 4 wherein R$^0$ is

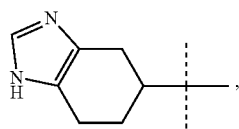

or a pharmaceutically acceptable salt thereof.

6. A compound of claim 4 wherein R$^0$ is

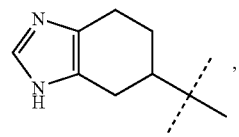

or a pharmaceutically acceptable salt thereof.

7. A compound of claim 4 wherein R$^4$ is

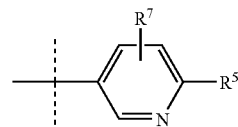

and R$^7$ is hydrogen, or a pharmaceutically acceptable salt thereof.

8. A compound of claim 4 wherein R$^4$ is

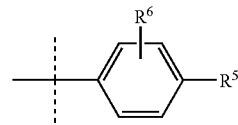

and R$^6$ is hydrogen, or a pharmaceutically acceptable salt thereof.

9. A compound of claim 8 wherein R$^5$ is

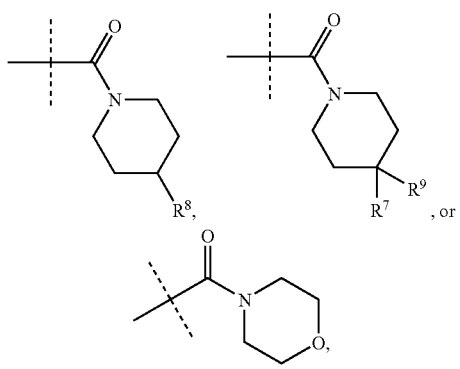

and R$^8$ is —(C$_1$-C$_3$)alkyl(optionally substituted with 1 to 3 halogens), or a pharmaceutically acceptable salt thereof.

10. A compound of claim 8 wherein R$^5$ is chlorine or fluorine, or a pharmaceutically acceptable salt thereof.

11. A compound of claim 8 wherein R$^5$ is fluorine, or a pharmaceutically acceptable salt thereof.

12. A compound that is (R)-3-(3,5-Dichloro-4'-morpholin-4-yl-biphenyl-4-ylmethyl)-1-(4,5,6,7-tetrahydro-1H-benzoimidazol-5-yl)-pyrrolidin-2-one or a pharmaceutically acceptable salt thereof.

13. A compound that is 3-(3,5-Dichloro-4'-fluoro-biphenyl-4-ylmethyl)-1-(4,5,6,7-tetrahydro-1H-benzoimidazol-5-yl)-pyrrolidin-2-one, or a pharmaceutically acceptable salt thereof.

14. A compound that is 3-[R]-[3,5-Dichloro-4'-(4-trifluoromethyl-piperidine-1-carbonyl)-biphenyl-4-ylmethyl]-1-(4,5,6,7-tetrahydro-3H-benzoimidazol-5-yl)-pyrrolidin-2-one, or a pharmaceutically acceptable salt thereof.

15. A pharmaceutical composition which comprises a compound of claim 1, or a pharmaceutically acceptable salt thereof, and a pharmaceutically acceptable carrier.

16. A method for alleviation of symptoms of metabolic syndrome in a patient in need thereof which comprises administering to said patient an effective amount of a compound of claim 1, or a pharmaceutically acceptable salt thereof.

17. A method for alleviation of symptoms of type 2 diabetes in a patient in need thereof which comprises administering to said patient an effective amount of a compound of claim 1, or a pharmaceutically acceptable salt thereof.

18. A method for alleviation of symptoms of atherosclerosis in a patient in need thereof which comprises administering to said patient an effective amount of a compound of claim 1, or a pharmaceutically acceptable salt thereof.

19. A compound that is

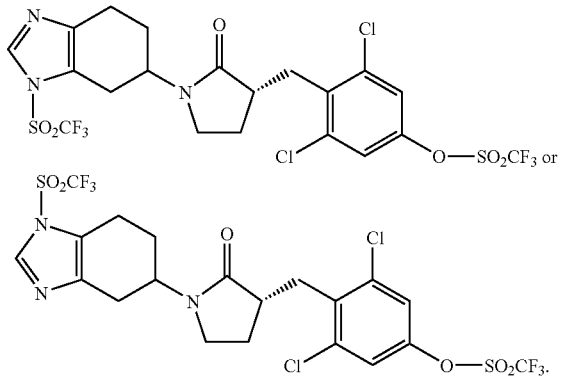

20. A compound of claim 1 selected from the group consisting of:

1-(4,5,6,7-Tetrahydro-3H-benzoimidazol-5-yl)-3-(3,5,4'-trichloro-biphenyl-4-ylmethyl)-pyrrolidin-2-one;

3-(3,5-Dichloro-biphenyl-4-ylmethyl)-1-(4,5,6,7-tetrahydro-1H-benzoimidazol-5-yl)-pyrrolidin-2-one;

3',5'-Dichloro-4'-[2-oxo-1-(4,5,6,7-tetrahydro-1H-benzoimidazol-5-yl)-pyrrolidin-3-ylmethyl]-biphenyl-4-carboxylic acid methyl ester;

3-(4-Benzofuran-5-yl-2,6-dichloro-benzyl)-1-(4,5,6,7-tetrahydro-1H-benzoimidazol-5-yl)-pyrrolidin-2-one;

3-(3,5-Dichloro-4'-morpholin-4-ylmethyl-biphenyl-4-ylmethyl)-1-(4,5,6,7-tetrahydro-1H-benzoimidazol-5-yl)-pyrrolidin-2-one;

3-[2,6-Dichloro-4-(3,5-dimethyl-isoxazol-4-yl)-benzyl]-1-(4,5,6,7-tetrahydro-1H-benzoimidazol-5-yl)-pyrrolidin-2-one;

3-(2,6-Dichloro-4-pyridin-3-yl-benzyl)-1-(4,5,6,7-tetrahydro-1H-benzoimidazol-5-yl)-pyrrolidin-2-one;

1-(4,5,6,7-Tetrahydro-1H-benzoimidazol-5-yl)-3-(3,5,3'-trichloro-4'-trifluoromethyl-biphenyl-4-ylmethyl)-pyrrolidin-2-one;

3-(3,5,2',4'-Tetrachloro-biphenyl-4-ylmethyl)-1-(4,5,6,7-tetrahydro-1H-benzoimidazol-5-yl)-pyrrolidin-2-one;

3-(3,5-Dichloro-3'-methyl-biphenyl-4-ylmethyl)-1-(4,5,6,7-tetrahydro-1H-benzoimidazol-5-yl)-pyrrolidin-2-one;

3-(3,5-Dichloro-4'-methyl-biphenyl-4-ylmethyl)-1-(4,5,6,7-tetrahydro-1H-benzoimidazol-5-yl)-pyrrolidin-2-one;

3-(3,5-Dichloro-3'-trifluoromethyl-biphenyl-4-ylmethyl)-1-(4,5,6,7-tetrahydro-1H-benzoimidazol-5-yl)-pyrrolidin-2-one;

3-(4'-tert-Butyl-3,5-dichloro-biphenyl-4-ylmethyl)-1-(4,5,6,7-tetrahydro-1H-benzoimidazol-5-yl)-pyrrolidin-2-one;

3-(3,5-Dichloro-4'-isopropoxy-biphenyl-4-ylmethyl)-1-(4,5,6,7-tetrahydro-1H-benzoimidazol-5-yl)-pyrrolidin-2-one;

3-(3,5-Dichloro-4'-fluoro-biphenyl-4-ylmethyl)-1-(4,5,6,7-tetrahydro-1H-benzoimidazol-5-yl)-pyrrolidin-2-one;

3-[2,6-Dichloro-4-(1-methyl-1H-pyrazol-4-yl)-benzyl]-1-(4,5,6,7-tetrahydro-1H-benzoimidazol-5-yl)-pyrrolidin-2-one;

3-(3,5-Dichloro-4'-trifluoromethyl-biphenyl-4-ylmethyl)-1-(4,5,6,7-tetrahydro-1H-benzoimidazol-5-yl)-pyrrolidin-2-one;

3-[3,5-Dichloro-4'-(4-methyl-piperazine-1-carbonyl)-biphenyl-4-ylmethyl]-1-(4,5,6,7-tetrahydro-1H-benzoimidazol-5-yl)-pyrrolidin-2-one;

3-[3,5-Dichloro-4'-(morpholine-4-carbonyl)-biphenyl-4-ylmethyl]-1-(4,5,6,7-tetrahydro-1H-benzoimidazol-5-yl)-pyrrolidin-2-one;

3-[3,5-Dichloro-4'-(4-ethyl-piperazine-1-carbonyl)-biphenyl-4-ylmethyl]-1-(4,5,6,7-tetrahydro-1H-benzoimidazol-5-yl)-pyrrolidin-2-one;

3-[3,5-Dichloro-4'-(4-trifluoromethyl-piperidine-1-carbonyl)-biphenyl-4-ylmethyl]-1-(4,5,6,7-tetrahydro-1H-benzoimidazol-5-yl)-pyrrolidin-2-one;

3-[R]-[4-(4-fluorophenyl-2,6-dichloro-benzyl)-1-(4,5,6,7-tetrahydro-3H-benzimidazole-3-yl)-pyrrolidin-2-one;

(R)-3-[3,5-Dichloro-4'-(morpholine-4-carbonyl)-biphenyl-4-ylmethyl]-1-(4,5,6,7-tetrahydro-1H-benzoimidazol-5-yl)-pyrrolidin-2-one;

1-(4,5,6,7-Tetrahydro-3H-benzoimidazol-5-yl)-3-[R]-[2,6-dichloro-4(4-N,N-dimethylsulfonylphenyl)-phenyl-pyrrolidin-2-one;

(R)-3-(3,5-Dichloro-4'-piperidin-1-yl-biphenyl-4-ylmethyl)-1-(4,5,6,7-tetrahydro-1H-benzoimidazol-5-yl)-pyrrolidin-2-one;

(R)-3-(2,6-Dichloro-4-cyclohex-1-enyl-benzyl)-1-(4,5,6,7-tetrahydro-1H-benzoimidazol-5-yl)-pyrrolidin-2-one;

(R)-3-(3,5-Dichloro-4'-morpholin-4-yl-biphenyl-4-ylmethyl)-1-(4,5,6,7-tetrahydro-1H-benzoimidazol-5-yl)-pyrrolidin-2-one;

(R)-3-(3,5-Dichloro-4'-dimethylamino-biphenyl-4-ylmethyl)-1-(4,5,6,7-tetrahydro-1H-benzoimidazol-5-yl)-pyrrolidin-2-one;

(R)-3-[2,6-Dichloro-4-(2-pyrrolidin-1-yl-pyrimidin-5-yl)-benzyl]-1-(4,5,6,7-tetrahydro-1H-benzoimidazol-5-yl)-pyrrolidin-2-one;

(R)-3-[2,6-Dichloro-4-(2-fluoro-6-morpholin-4-yl-pyridin-3-yl)-benzyl]-1-(4,5,6,7-tetrahydro-1H-benzoimidazol-5-yl)-pyrrolidin-2-one;

(R)-3-(4-Benzo[1,2,5]oxadiazol-5-yl-2,6-dichloro-benzyl)-1-(4,5,6,7-tetrahydro-1H-benzoimidazol-5-yl)-pyrrolidin-2-one;

(R)-3-(4-Benzo[b]thiophen-5-yl-2,6-dichloro-benzyl)-1-(4,5,6,7-tetrahydro-1H-benzoimidazol-5-yl)-pyrrolidin-2-one;

(R)-3-[2,6-Dichloro-4-(1H-indol-5-yl)-benzyl]-1-(4,5,6,7-tetrahydro-1H-benzoimidazol-5-yl)-pyrrolidin-2-one;

(R)-3-[2,6-Dichloro-4-(2-methoxy-pyrimidin-5-yl)-benzyl]-1-(4,5,6,7-tetrahydro-1H-benzoimidazol-5-yl)-pyrrolidin-2-one;

(R)-3-[3,5-Dichloro-4'-(piperidine-1-sulfonyl)-biphenyl-4-ylmethyl]-1-(4,5,6,7-tetrahydro-1H-benzoimidazol-5-yl)-pyrrolidin-2-one;

3',5'-Dichloro-4'-[(R)-2-oxo-1-(4,5,6,7-tetrahydro-1H-benzoimidazol-5-yl)-pyrrolidin-3-ylmethyl]-biphenyl-4-sulfonic acid isopropylamide;

(R)-3-[3,5-Dichloro-4'-(morpholine-4-sulfonyl)-biphenyl-4-ylmethyl]-1-(4,5,6,7-tetrahydro-1H-benzoimidazol-5-yl)-pyrrolidin-2-one;

(R)-3-[3,5-Dichloro-4'-(methylsulfonyl)-biphenyl-4-ylmethyl]-1-(4,5,6,7-tetrahydro-1H-benzoimidazol-5-yl)-pyrrolidin-2-one;

(R)-3-[3,5-Dichloro-4'-(azitidine-4-sulfonyl)-biphenyl-4-ylmethyl]-1-(4,5,6,7-tetrahydro-1H-benzoimidazol-5-yl)-pyrrolidin-2-one;

3-[R]-[3,5-Dichloro-4'-(4-trifluoromethyl-piperidine-1-carbonyl)-biphenyl-4-ylmethyl]-1-(4,5,6,7-tetrahydro-3H-benzoimidazol-5-yl)-pyrrolidin-2-one;

(R)-3-[3,5-Dichloro-4'-(4,4-difluoro-piperidine-1-carbonyl)-biphenyl-4-ylmethyl]-1-(4,5,6,7-tetrahydro-1H-benzoimidazol-5-yl)-pyrrolidin-2-one; and 3-(4-Bromo-2-chlorobenzyl)-1-(4,5,6,7-tetrahydro-3H-benzo[d]imidazol-5-yl)pyrrolidin-2-one;

or a pharmaceutically acceptable salt thereof.

* * * * *